US011499002B2

(12) United States Patent
Savonnet et al.

(10) Patent No.: US 11,499,002 B2
(45) Date of Patent: *Nov. 15, 2022

(54) POLYEPOXIDIZED BIPHENYL COMPOUNDS, PREPARATION AND USES

(71) Applicants: ARIANEGROUP SAS, Paris (FR); CENTRE NATIONAL DE LA RECHERCHE SCIENTIFIQUE, Paris (FR)

(72) Inventors: Etienne Savonnet, Paris (FR); Brigitte Defoort, Saint-Medard-en-Jalles (FR); Henri Cramail, Saint-terre (FR); Stéphane Grelier, Parentis-en-born (FR); Etienne Grau, Bordeaux (FR)

(73) Assignees: ARIANEGROUP SAS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 99 days.

This patent is subject to a terminal disclaimer.

(21) Appl. No.: 16/762,012

(22) PCT Filed: Nov. 7, 2018

(86) PCT No.: PCT/FR2018/052746
§ 371 (c)(1),
(2) Date: May 6, 2020

(87) PCT Pub. No.: WO2019/092359
PCT Pub. Date: May 16, 2019

(65) Prior Publication Data
US 2021/0403636 A1    Dec. 30, 2021

(30) Foreign Application Priority Data

Nov. 7, 2017  (FR) ...................... 1760451

(51) Int. Cl.
*C08G 59/38* (2006.01)
*C07D 301/28* (2006.01)
(Continued)

(52) U.S. Cl.
CPC ........... *C08G 59/38* (2013.01); *C07D 301/28* (2013.01); *C07D 303/28* (2013.01); *C08G 59/245* (2013.01); *C08G 59/3218* (2013.01)

(58) Field of Classification Search
CPC .. C08G 59/38; C08G 59/245; C08G 59/3218; C07D 301/28; C07D 303/28
(Continued)

(56) References Cited

U.S. PATENT DOCUMENTS

2013/0196114 A1* 8/2013 Urano ....................... G03F 7/20
528/27
2014/0069583 A1* 3/2014 Kincaid ................. C09J 163/00
156/330

FOREIGN PATENT DOCUMENTS

EP    3 002 333 A1    4/2016
EP    3 165 549 A1    5/2017
JP    2017-165694 A    9/2017

OTHER PUBLICATIONS

Niwa et al., JP 2017-165694 A machine translation in English, Sep. 21, 2017 (Year: 2017).*

(Continued)

*Primary Examiner* — David T Karst
(74) *Attorney, Agent, or Firm* — Pillsbury Winthrop Shaw Pittman LLP

(57) ABSTRACT

A multi-epoxidized biphenyl compound has the formula (I) below (Continued)

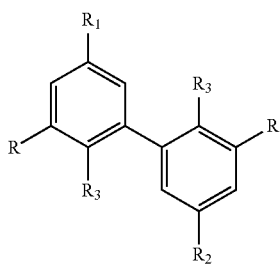

wherein R, $R_1$, $R_2$ and $R_3$ are as defined in the description, as well as mixtures of at least two of the compounds. These multi-epoxidized biphenyl compounds are fully suitable as main constituents of thermosetting epoxy resins, i.e. as polyepoxides precursors. They are beneficial substitutes for bisphenol A diglycidyl ether.

31 Claims, 24 Drawing Sheets

(51) Int. Cl.
*C07D 303/28* (2006.01)
*C08G 59/24* (2006.01)
*C08G 59/32* (2006.01)

(58) Field of Classification Search
USPC .......................................................... 525/524
See application file for complete search history.

(56) References Cited

OTHER PUBLICATIONS

Fache, M., et al., "Vanillin, a promising biobased building-block for monomer synthesis," Royal Society of Chemistry, Green Chemistry 2014, 16 (4), pp. 1987-1998.
François, C., et al., "Diglycidylether of iso-eugenol: a suitable lignin-derived synthon for epoxy thermoset applications," Royal Society of Chemistry, RSC Advances 2016, 6 (73), pp. 68732-68738.
Qin, J., et al., "Use of eugenol and rosin as feedstocks for biobased epoxy resins and study of curing and performance properties," Polym. Int. 2014, 63 (4), pp. 760-765.
International Search Report as issued in International Patent Application No. PCT/FR2018/052746, dated Jan. 18, 2019.
Duann, Y.-F., et al. "Thermal stability of some naphthalene- and phenyl-based epoxy resins," Polymer Degradation and Stability, vol. 84, No. 2, May 2004, XP004510148, pp. 305-310.
Fetouaki, S., et al., "Synthèse d'une nouvelle résine époxyde a base du 2,2'-dihydroxydiphényle," European Polymer Journal, vol. 38, No. 4, Apr. 2002, XP004340248, pp. 787-793.

* cited by examiner

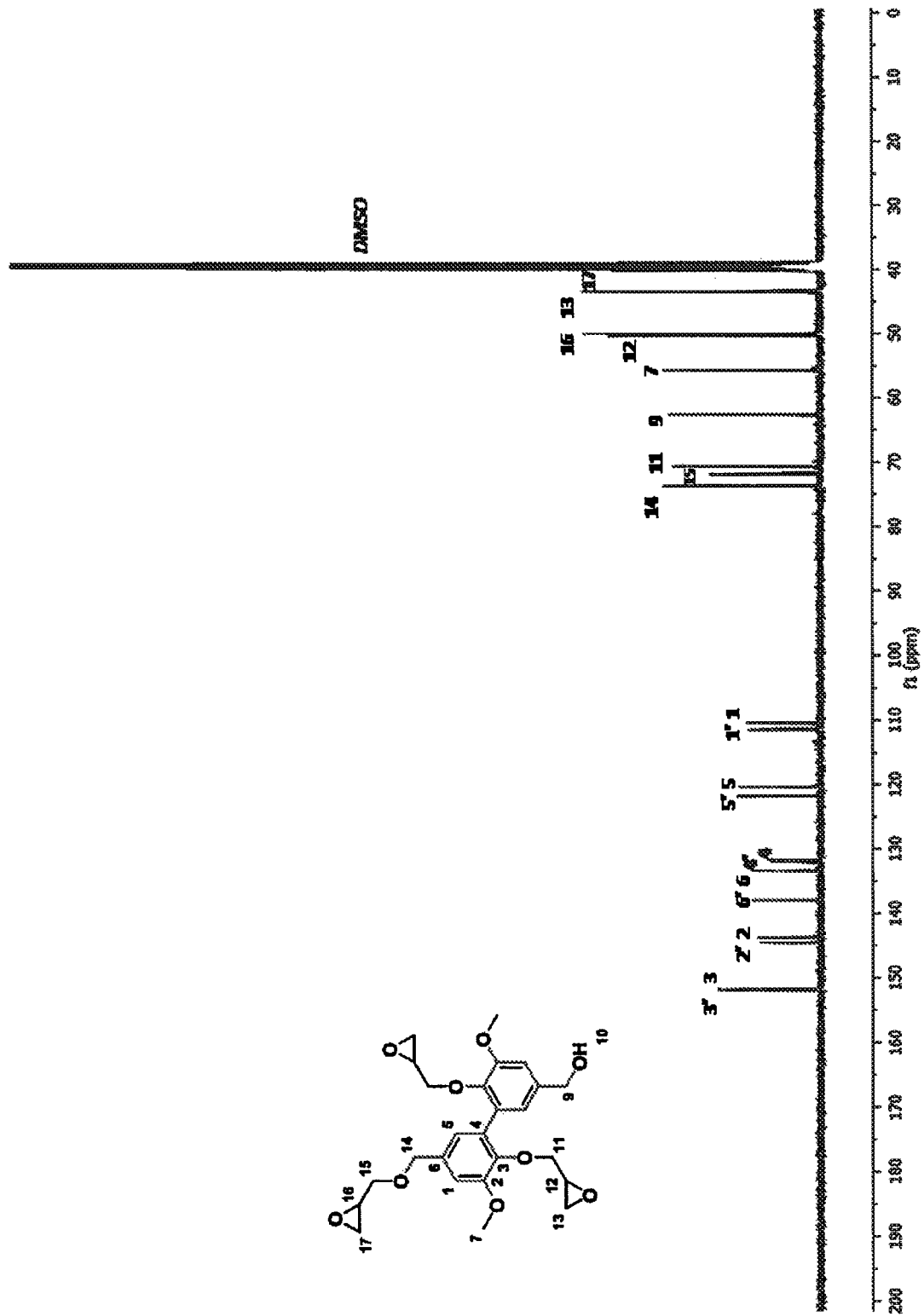

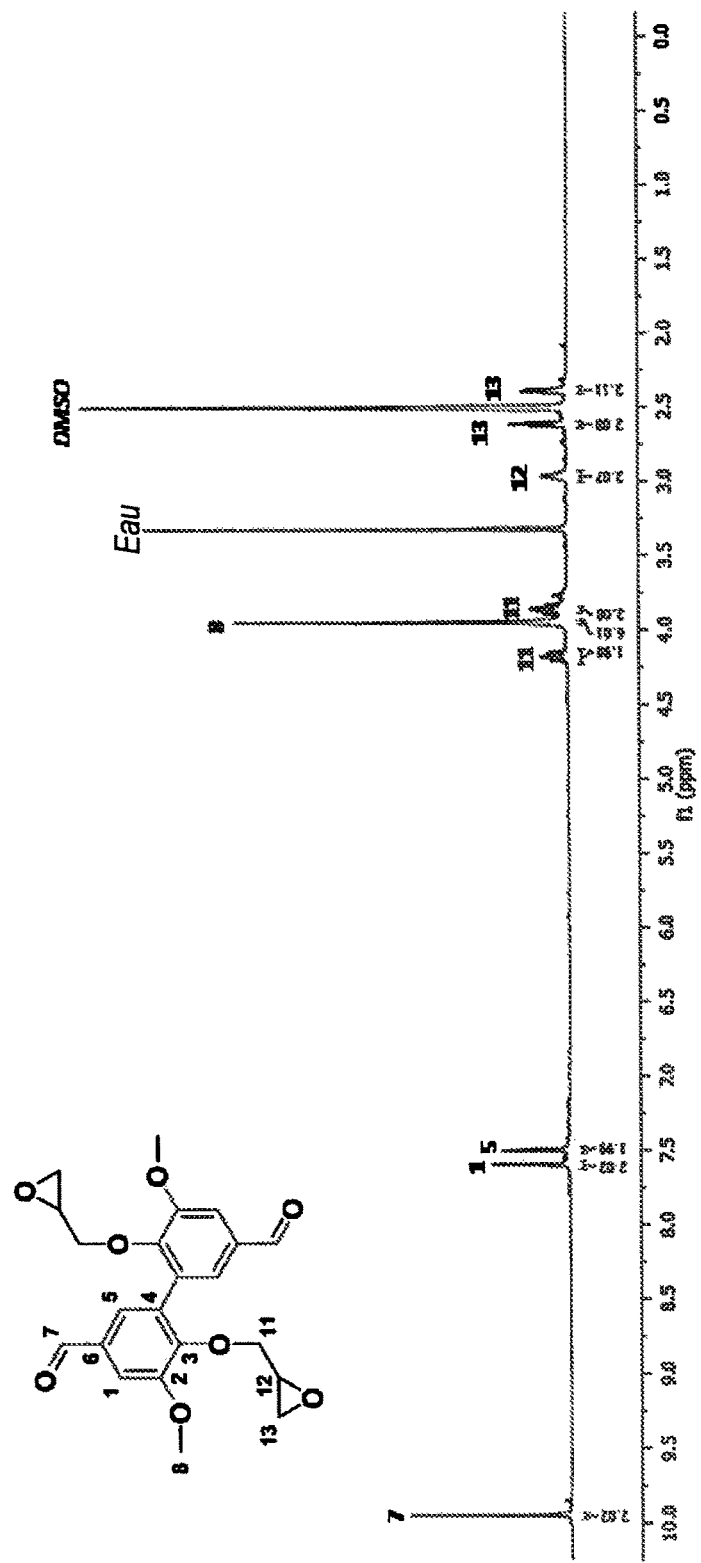

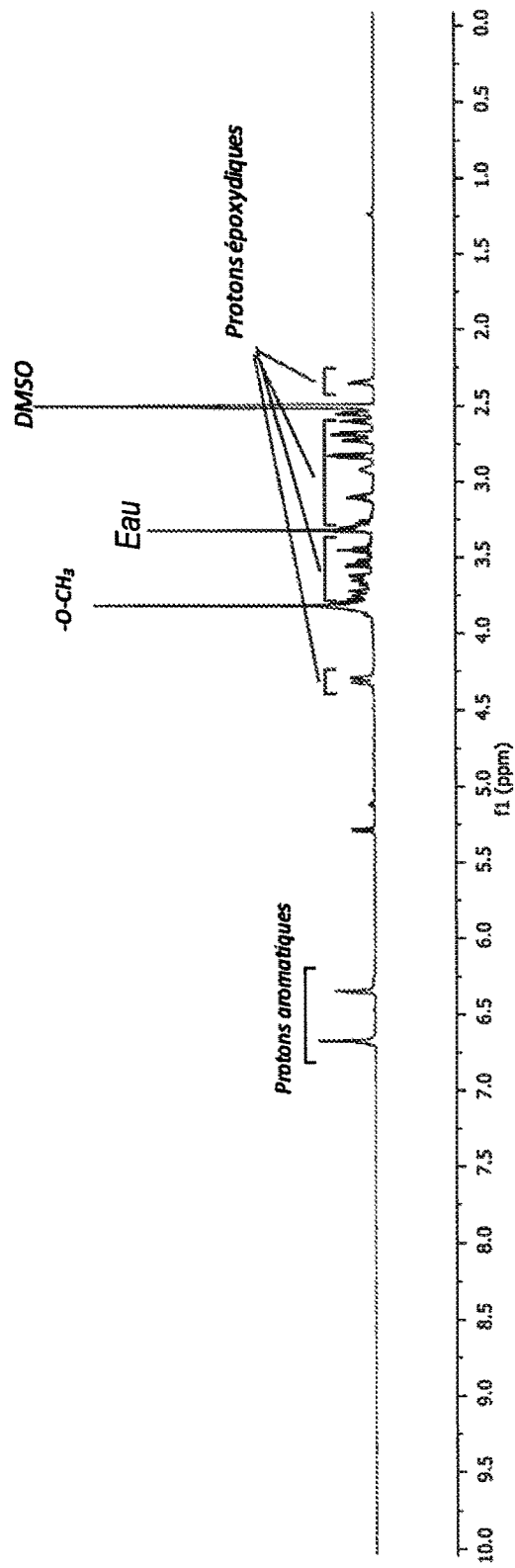

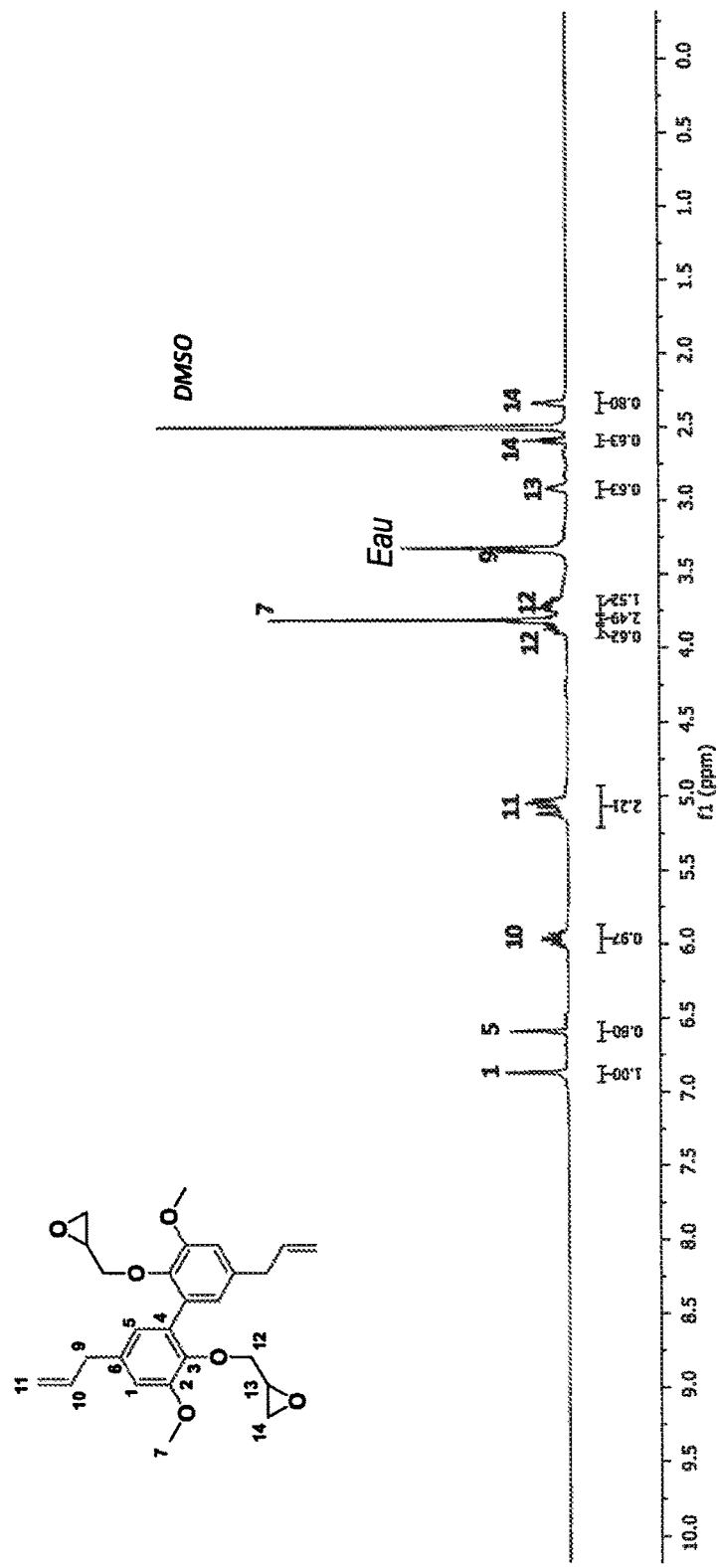

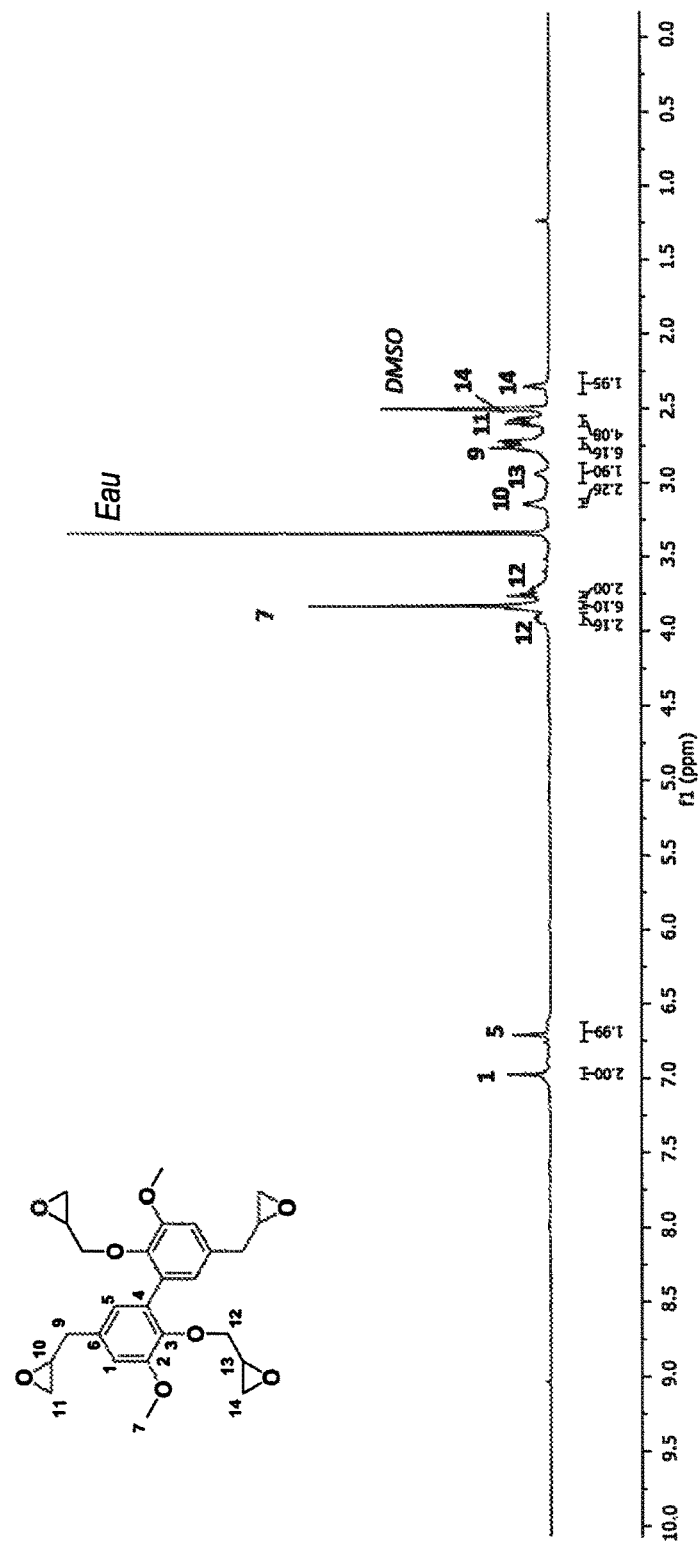

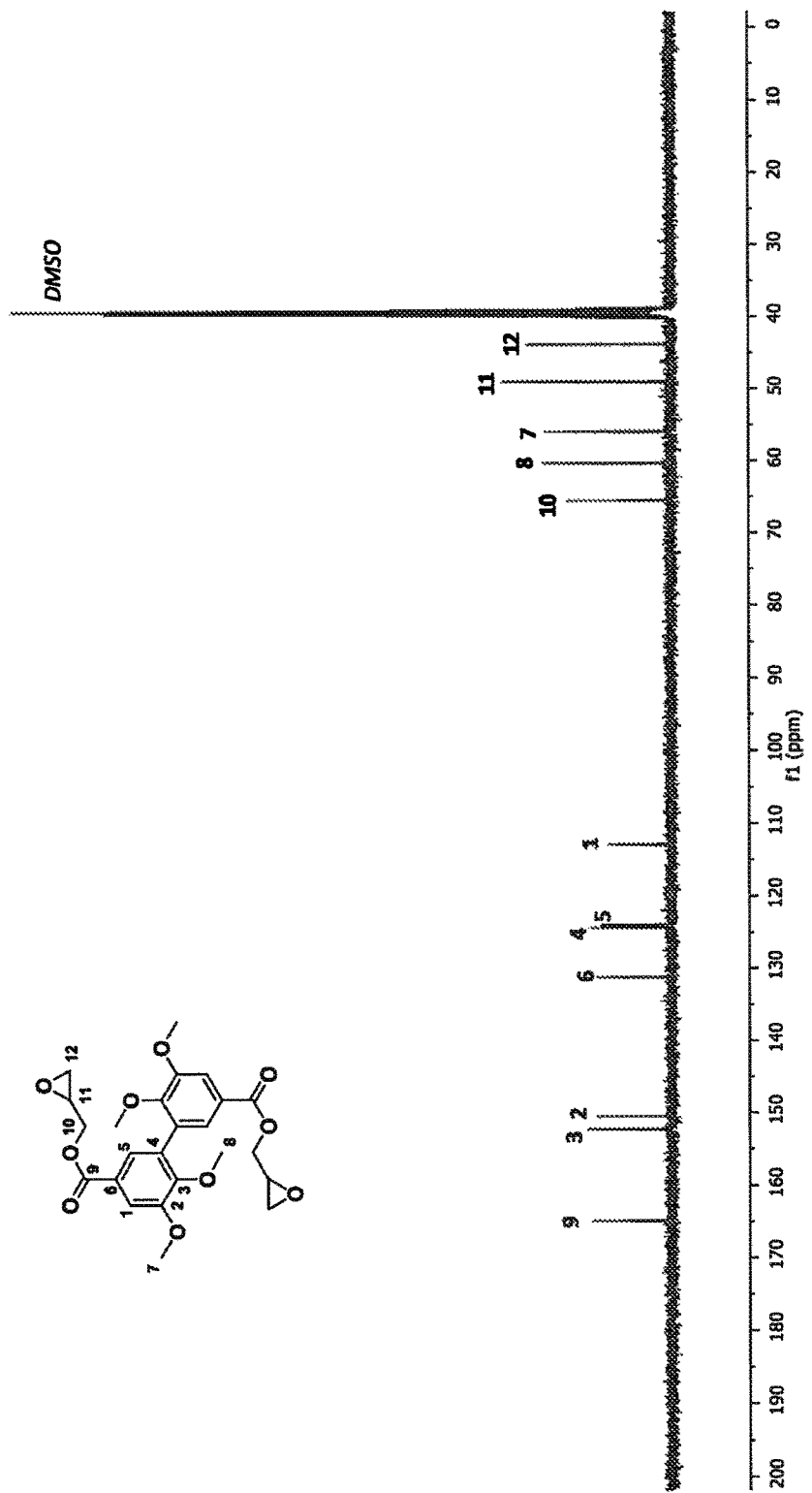

POLYEPOXIDIZED BIPHENYL COMPOUNDS, PREPARATION AND USES

CROSS-REFERENCE TO RELATED APPLICATIONS

This application is the U.S. National Stage of PCT/FR2018/052746, filed Nov. 7, 2018, which in turn claims priority to French patent application number 1760451 filed Nov. 7, 2017. The content of these applications are incorporated herein by reference in their entireties.

The main subject matter of the present invention is multi-epoxidized biphenyl compounds (i.e. whose chemical formula contains at least two epoxy functions). These compounds constitute epoxy resin type thermosetting monomers or prepolymers. They are of particular interest in that they are perfectly suitable as precursors for obtaining polyepoxides (thermoset epoxy resins) with high mechanical and temperature-resistant properties and in that, for many of them, they can be obtained, in addition to conventional synthesis methods (known in the petrochemical field), from biomass (from lignin) (i.e. biosourced products). The polyepoxides, another subject matter of the present invention, obtained from multi-epoxidized biphenyl compounds, the main subject matter of the present invention, constitute in particular high-performance glues (see below). However, their use is not limited to this bonding application.

To date, epoxy resins, which can be polymerized under the action of a hardener (so-called cross-linking polymerization), represent the majority of structural adhesives and more than 75% of them are obtained from bisphenol-A diglycidyl ether, or DGEBA, (monomer or prepolymer), which has the following chemical formula:

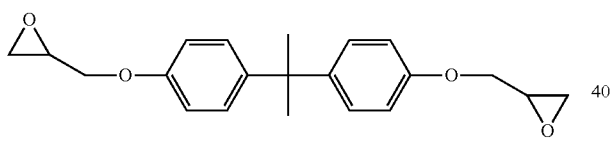

The latter is itself obtained from bisphenol A (BPA), which has the following chemical formula:

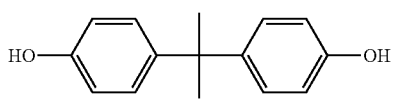

and is known to be toxic, in particular as an endocrine disruptor. This does not fail to pose problems and will not fail to pose increasingly serious problems in view of the increasingly restrictive regulations that are required. Moreover, the skilled person is well aware that said BPA is obtained from fossil resources.

Thus, for several years, with reference to public health and environmental considerations, there has been a search for new precursors (new monomers or prepolymers) of polyepoxides, substitutes for said DGEBA, which are non-toxic and advantageously of natural origin (advantageously biosourced).

Vanillin, a compound with the following chemical formula, has been investigated:

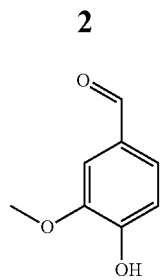

Vanillin is a priori a very interesting candidate as it is one of the few non-toxic aromatic compounds available industrially from biomass.

The use of vanillin and its derivatives, as basic building blocks, of natural origin, of renewable polymers and in particular of epoxy resins, has thus been studied with great interest. Recently, cured vanillin-based epoxy resins with Tg between 80° C. and 176° C. have been synthesized.

On this use of vanillin, see in particular Fache, M.; Darroman, E.; Besse, V.; Auvergne, R.; Caillol, S.; Boutevin, B. in Green Chem. 2014, 16 (4), 1987.

However, monomers with epoxy groups obtained from vanillin or its derivatives do not allow the production of polyepoxides with high mechanical and temperature resistant properties.

Similarly, eugenols (eugenol and isoeugenol) were also investigated. On this subject, see in particular François, C.; Pourchet, S.; Boni, G.; Fontaine, S.; Gaillard, Y.; Placet, V.; Galkin, M. V.; Orebom, A.; Samec, J.; Plasseraud, L. in RSC Adv. 2016, 6 (73), 68732-68738, and Qin, J.; Liu, H.; Zhang, P.; Wolcott, M.; Zhang, in J. Polym. Int. 2014, 63 (4), 760-765.

The polyepoxides obtained from these monomers were not fully satisfactory. The chemical formulas of said eugenol and isoeugenol are recalled below for all practical purposes:

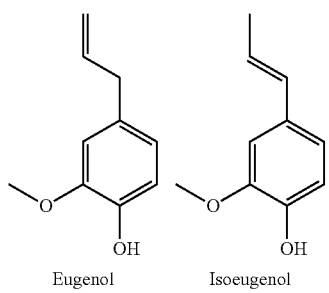

Eugenol   Isoeugenol

In such a context, it is to the inventors' credit to propose novel polyepoxide monomers or prepolymers. These are multi-epoxidized biphenyl compounds having the formula (I) below:

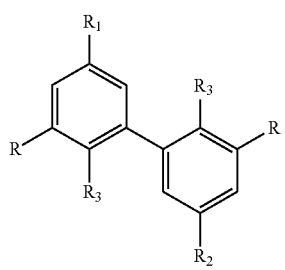

wherein:

R=—O-Alk, where Alk is a linear or branched alkyl group having from 1 to 6 carbon atoms, R being advantageously a methoxy group (—O—$CH_3$);

$R_3$=—O—Z, where Z is a linear or branched alkyl group having from 2, advantageously 3, to 8 carbon atoms and containing an epoxy function, or —O-Alk', where Alk' is a linear or branched alkyl group having from 1 to 6 carbon atoms; and + when $R_3$=—O—Z, then either $R_1$ and $R_2$, which may be the same or different, are independently selected from —$CH_2$—OH and —$CH_2$—O—Z;

or $R_1$=$R_2$=—CHO;

or $R_1$ and $R_2$, which may be the same or different, are independently selected from —OH and —O—Z;

or $R_1$ and $R_2$, which may be the same or different, are independently selected from —COOH and —COO—Z, or $R_1$ and $R_2$, which may be the same or different, are independently selected from —$CH_2$—CH=$CH_2$ and —$CH_2$— epoxy, or $R_1$ and $R_2$, which may be the same or different, are independently selected from —CH=CH—$CH_3$ and;

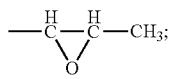

and

+ when $R_3$=—O-Alk', then $R_1$=$R_2$ and is selected from

—$CH_2$—O—Z,

—O—Z,

—COO—Z, with Z as defined above with reference to $R_3$=—O—Z (i.e. Z is a linear or branched alkyl group containing from 2, advantageously from 3, to 8 carbon atoms and containing an epoxy function), —$CH_2$-epoxy, and

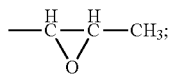

as well as mixtures of at least two such compounds (of said formula (I)).

It has already been understood that the compounds of formula (I)—multi-epoxidized (or poly-epoxidized) biphenyl compounds (with R=alkoxy)—are multi(2, 3 or 4)epoxidized (poly(2,3,4)epoxidized) insofar as at least two of the groups $R_1$, $R_2$ and the two groups $R_3$ of said formula (I) contain an epoxy function (epoxidized $R_3$ (=—O—Z) with $R_1$ or(and) $R_2$ possibly also epoxidized or $R_3$ not epoxidized (=—O-Alk') and then epoxidized $R_1$=$R_2$), and that they are divided into two main families according to the value of $R_3$.

As regards the alkoxy group, R=—O-Alk, as defined above, it advantageously consists of a group —O-Alk$_{lower}$, said lower alkyl group having only 1 to 4 carbon atoms, or very advantageously only 1 or 2 carbon atoms. It is further understood that the value of R is a priori fixed by the nature of the starting products used. Thus, from synthetic ethyl vanillin, compounds of formula (I) in which R=—O—$C_2H_5$ are obtained, from vanillin, eugenol and isoeugenol (synthetic or, rather advantageously, of natural origin), compounds of formula (I) in which R=—O—$CH_3$ are obtained. Said compounds of formula (I) in which R=—O—$CH_3$ are particularly preferred. Thus, the rest of the present description and the examples are extensively developed, in a non-limiting way, with reference to this preferred value.

With regard to the value of $R_3$, therefore, for the two main families mentioned above:

$R_3$=—O—Z, then the two groups $R_3$ each provide an epoxy function (the same) and the compound can be di-, tri- or tetra-epoxidized in view of the nature of the groups $R_1$ and $R_2$ (it is understood that for a compound of formula (I) in which $R_3$=—O—Z, $R_1$ or(and) $R_2$, if it(they) contain(s) Z, necessarily contain(s) the same Z (see the above definition of the groups $R_1$, $R_2$ and $R_3$, certainly confirmed by the following part of the description relating to the process aspect of the invention); or $R_3$=—O-Alk', an alkoxy group, then the groups $R_1$=$R_2$ each provide the same epoxy function and the compound is a di-epoxidized compound. If $R_1$=$R_2$ includes Z, it is obviously to the definition of Z (given with reference to $R_3$=—O—Z) that reference should be made (see the above definition of the groups $R_1$, $R_2$ and $R_3$, certainly confirmed by the following part of the description relating to the process aspect of the invention).

Each of these two main families is itself made up, according to the same logic, of sub-families.

The construction of said families and sub-families obviously derives, on the one hand, from the nature of the starting products (advantageously derived from biomass), more precisely from the functions present in the chemical formula of said starting products and in that of the intermediate products obtained from said starting products, functions which are capable of being epoxidized (alcohol, hydroxy, acid, —CH=$CH_2$ or —CH=CH— functions) and, on the other hand, from the reactions implemented for the epoxidation of said functions.

It is proposed to specify each of these families and sub-families below.

1$^{st}$ family: $R_3$=—O—Z, with Z a linear or branched alkyl group containing from 2, advantageously from 3, to 8 carbon atoms, and containing an epoxy function (said epoxy function containing 2 of said 2 to 8 (total) carbon atoms). It should be noted here that the expression "branched alkyl group" includes "a conventional branched alkyl group and an alkyl group including a cycloalkyl (with one of the carbon atoms of the alkyl chain also belonging to said cycloalkyl")".

It can be stated, in a non-limiting way, that, according to advantageous, independent variants:

Z is linear,

Z contains said epoxy function at the chain end;

said advantageous variants, taken in combination, constituting a very advantageous variant (Z, ($C_2$-$C_8$)alkyl, linear, containing said epoxy function at the chain end, i.e. $R_3$=—O—[$CH_2$-]$_n$-epoxy with n, an integer from 0, advantageously from 1, to 6).

As a non-limiting way, some values of Z can be specified here:

Z=—[$CH_2$]$_n$-epoxy, with n an integer from 0 to 6, advantageously from 1 to 6 and in particular n=4, very advantageously n=1, Z=—$CH_2$—CH($CH_3$)—$CH_2$—$CH_2$-epoxy,

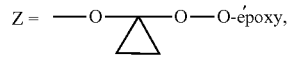

and

Z=CH$_2$—C(CH$_3$)$_2$—CH$_2$—CH$_2$-epoxy.

According to a preferred variant, Z=—[CH$_2$—]$_n$-epoxy with 1≤n≤4 and, according to a particularly preferred variant, Z=—CH$_2$-epoxy and thus R$_3$=—O—CH$_2$— epoxy.

In this first family, as indicated above, biphenyl compounds can be di-, tri- or tetra-epoxidized.

a) In the context of its first subject matter, the present invention therefore relates to the biphenyl compounds of formula (I) wherein: R$_3$=—O—Z (see above) and R$_1$ and R$_2$, which may be the same or different, are chosen independently from —CH$_2$—OH and —CH$_2$—O—Z, as well as to mixtures of at least two of said compounds. These compounds are compounds derived from divanillyl alcohol. The present invention particularly relates to said compounds of formula (I) with R$_3$=—O—[CH$_2$—]$_n$-epoxy (with n, an integer from 0, advantageously from 1, to 6) and, R$_1$ and R$_2$, which may be the same or different, are chosen independently from —CH$_2$—OH and —CH$_2$—O—[CH$_2$—]$_n$-epoxy, as well as to mixtures of at least two of said compounds. It relates to in particular said compounds with R$_3$=—O—CH$_2$-epoxy and R$_1$ and R$_2$, which may be the same or different, are chosen independently from —CH$_2$—OH and —CH$_2$—O—CH$_2$-epoxy, as well as to mixtures of at least two of said compounds, namely:

diglycidyl ether of divanillyl alcohol (DiGEDVA), triglycidyl ether of divanillyl alcohol (TriGEDVA), tetraglycidyl ether of divanillyl alcohol (TetraGEDVA),

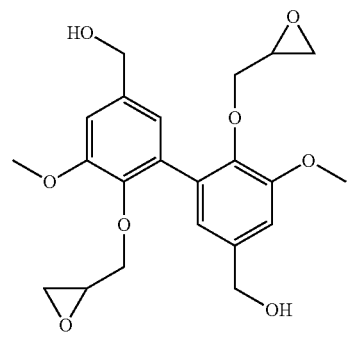

DiGEDVA

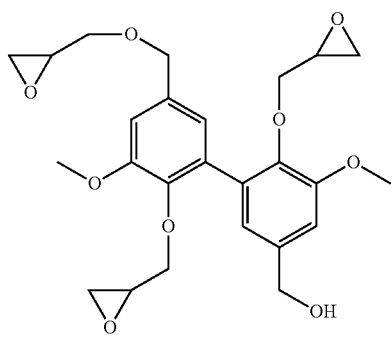

TriGEDVA

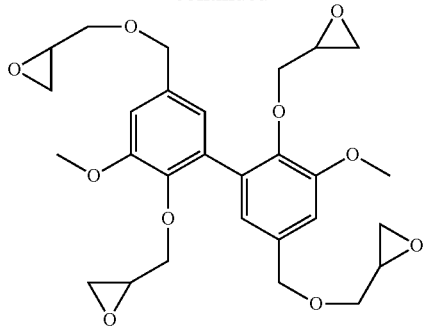

TetraGEDVA and mixtures of at least two of said glycidyl ethers of divanillyl alcohol.

b) In the context of its first subject matter, the present invention also relates to biphenyl compounds of formula (I) in which R$_3$=—O—Z (see above) and R$_1$ and R$_2$ are identical, equal to —CHO. These compounds are derivatives of divanillin. They have retained the aldehyde functions of divanillin but the hydroxy functions of the latter have been epoxidized (and have become —O—Z). The present invention thus particularly relates to said compounds of formula (I) with R$_3$=—O—[CH$_2$—]$_n$-epoxy (with n, an integer from 0, advantageously from 1, to 6) and R$_1$=R$_2$=—CHO. It relates to in particular the compound of formula (I) in which R$_3$=—O—CH$_2$-epoxy and R$_1$=R$_2$=—CHO, namely diglycidyl ether of divanillin (DiGEDV), the formula (I) of which is reproduced below:

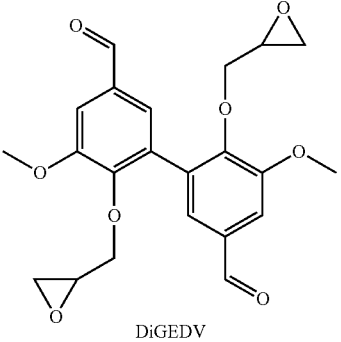

DiGEDV c) In the context of its first subject matter, the present invention also relates to the compounds of formula (I) in which R$_3$=—O—Z (see above) and R$_1$ and R$_2$, which may be the same or different, are chosen independently from —OH and —O—Z, as well as to mixtures of at least two of said compounds. These compounds are compounds derived from dimethoxyhydroquinone. The present invention particularly relates to said compounds of formula (I) with R$_3$=—O—[CH$_2$-]$_n$-epoxy (with n, an integer from 0, advantageously from 1, to 6) and, R$_1$ and R$_2$, which may be the same or different, are chosen independently from —OH and —O—[CH$_2$-]$_n$-epoxy, as well as to mixtures of at least two of said compounds. It particularly relates to said compounds with R$_3$=—O—CH$_2$-epoxy and R$_1$ and R$_2$, which may be the same or different, are chosen independently from —OH and —O—CH$_2$-epoxy, as well as to mixtures of at least two of said compounds, namely:

diglycidyl ether of dimethoxyhydroquinone (DiGEDMHQ),
triglycidyl ether of dimethoxyhydroquinone (TriGEDMHQ),
tetraglycidyl ether of dimethoxyhydroquinone (TetraGEDMHQ),

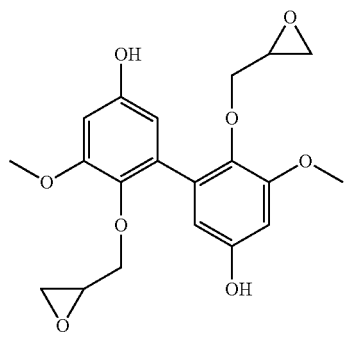

DiGEDMHQ

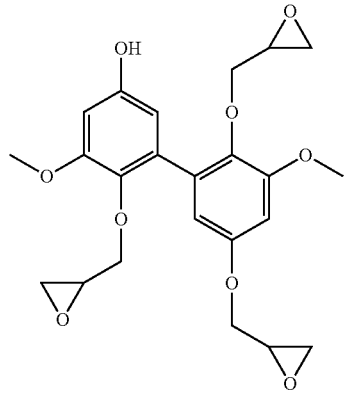

TriGEDMHQ

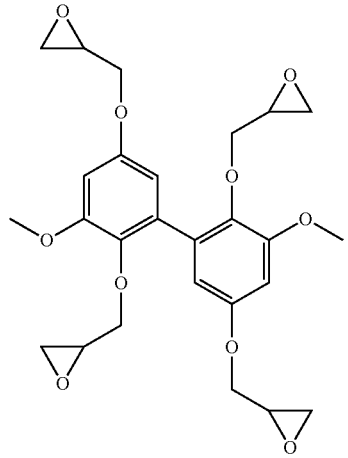

TetraGEDMHQ and
mixtures of at least two of said glycidyl ethers of dimethoxyhydroquinone.
Tetraglycidyl ether of dimethoxyhydroquinone (TetraGEDMHQ) is particularly preferred.

d) In the context of its first subject matter, the present invention also relates to biphenyl compounds of formula (I) in which $R_3$=—O—Z (see above) and $R_1$ and $R_2$, which may be the same or different, are chosen from —COOH and —COO—Z, as well as to mixtures of at least two of said compounds. These compounds are derivatives of an alkyl divanillate (ester), in fact divanillic acid. The present invention particularly relates to said compounds of formula (I) in which $R_3$=—O—[CH$_2$-]$_n$-epoxy (with n, an integer from 0, advantageously from 1, to 6) and $R_1$ and $R_2$, which may be the same or different, are chosen from —COOH and —COO—[CH$_2$-]$_n$-epoxy, as well as to mixtures of at least two of said compounds. It relates in particular to said compounds with $R_3$=—O—CH$_2$-epoxy and $R_1$ and $R_2$, which may be the same or different, are chosen independently from —COOH and —COO—CH$_2$-epoxy, as well as to mixtures of at least two of said compounds, namely:
diglycidyl ether of divanillic acid (DiGEDVAc),
triglycidyl ether of divanillic acid (TriGEDVAc),
tetraglycidyl ether of divanillic acid (TetraGEDVAc),

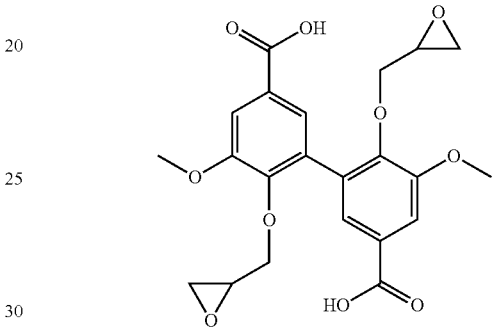

DiGEDVAc

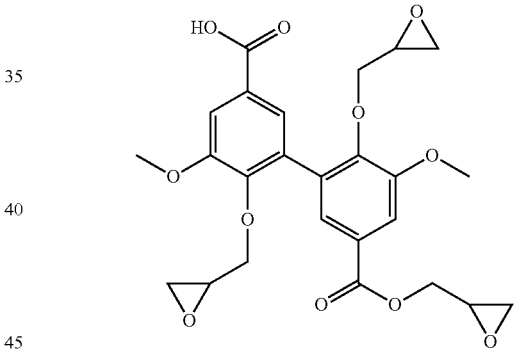

TriGEDVAc

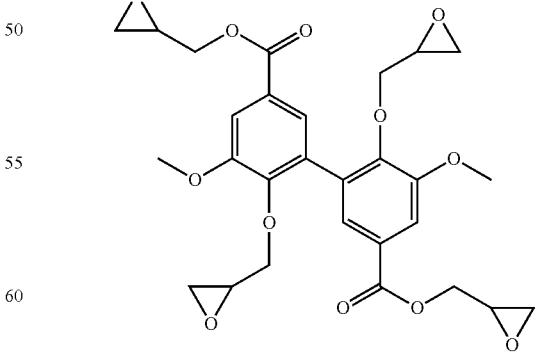

TetraGEDVAc and mixtures of at least two of said ethers of divanillic acid.

e) In the context of its first subject matter, the present invention also relates to biphenyl compounds of formula (I) in which $R_3$=—O—Z (see above) and $R_1$ and $R_2$, which may be the same or different, are selected from —CH$_2$—CH=CH$_2$ and —CH$_2$-epoxy, as well as to mixtures of at least two of said compounds. These compounds are derivatives of dieugenol. The present invention particularly relates to said compounds of formula (I) in which $R_3$=—O—[CH$_2$-]$_n$-epoxy (with n, an integer from 0, advantageously from 1, to 6) and $R_1$ and $R_2$, which may be the same or different, are chosen from —CH$_2$—CH=CH$_2$ and —CH$_2$-epoxy, as well as to mixtures of at least two of said compounds. It relates to in particular said compounds with $R_3$=—O—CH$_2$-epoxy and $R_1$ and $R_2$, which may be the same or different, are chosen independently from —CH$_2$—CH=CH$_2$ and —CH$_2$-epoxy, as well as to mixtures of at least two of said compounds, namely:

diglycidyl ether of dieugenol (DiGEDEG),
triglycidyl ether of dieugenol (TriGEDEG),
tetraglycidyl ether of dieugenol (TetraGEDEG),

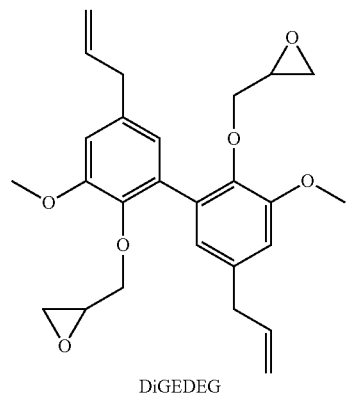

DiGEDEG

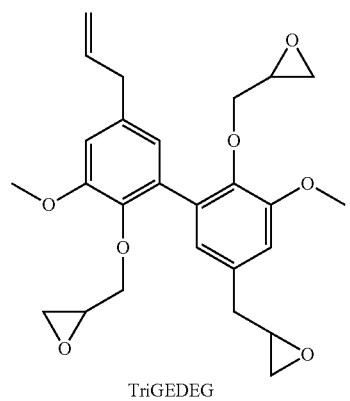

TriGEDEG

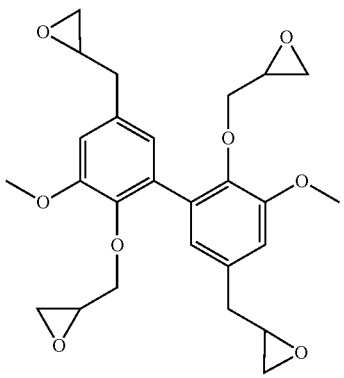

TetraGEDEG and mixtures of at least two of said dieugenol ethers.

f) In the context of its first subject matter, the present invention also relates to biphenyl compounds of formula (I) in which $R_3$=—O—Z (see above) and $R_1$ and $R_2$, which may be the same or different, are selected independently from —CH=CH—CH$_3$ and

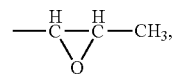

as well as to mixtures of at least two of said compounds. These compounds are derivatives of diisoeugenol. The present invention particularly relates to said compounds of formula (I) in which $R_3$=—O—[CH$_2$—]$_n$-epoxy (with n, an integer from 0, advantageously from 1, to 6) and $R_1$ and $R_2$, which may be the same or different, are chosen from —CH=CH—CH$_3$ and

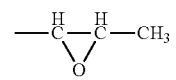

as well as to mixtures of at least two of said compounds. It particularly relates to said compounds with $R_3$=—O—CH$_2$-epoxy and, $R_1$ and $R_2$, which may be the same or different, are independently selected from —CH=CH—CH$_3$ and

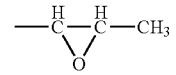

as well as to mixtures of at least two of said compounds, namely:

diglycidyl ether of diisoeugenol (DiGEDisoEG),
triglycidyl ether of diisoeugenol (TriGEDisoEG),
tetraglycidyl ether of diisoeugenol (TetraGEDisoEG),

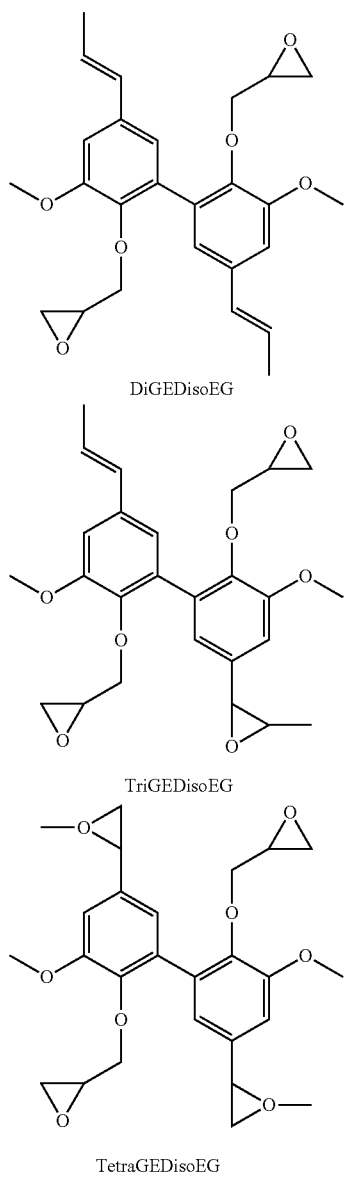

DiGEDisoEG

TriGEDisoEG

TetraGEDisoEG and mixtures of at least two of said dieugenol ethers.

Incidentally, it should be noted that said TriGEDisoEG and TetraGEDisoEG do not all have their epoxy functions at the chain end. The skilled person already understands that the epoxy functions which are not at the chain end are those corresponding to the double bonds of diisoeugenol.

2$^{nd}$ family $R_3$=—O-Alk', where Alk' is a linear or branched alkyl group having 1 to 6 carbon atoms. Alk' is independent of Alk but in the same way, it advantageously consists of a group Alk'$_{lower}$, said lower alkyl group having only 1 to 4 carbon atoms. Very advantageously, said alkyl group (Alk') has only one (1) carbon atom. Therefore, very advantageously, $R_3$=—OCH$_3$ (a methoxy group).

The groups $R_3$ of the compounds of formula (I) (multi-epoxidized biphenyl compounds) of the second family being thus not epoxidized (but alkylated), their groups $R_1$ and $R_2$ should therefore be epoxidized. The compounds of the second family are, as indicated above, di-epoxidized via said groups $R_1$ and $R_2$ ($R_1$=$R_2$).

Said groups $R_1$ and $R_2$, in view of the raw materials and the recommended non-complex syntheses (see below), are as specified above:

$R_1$=$R_2$=—CH$_2$—O—Z, or —O—Z, or —COO—Z, with, for these three values, Z as defined above with reference to $R_3$=—O—Z, i.e. Z is a linear or branched alkyl group containing from 2, advantageously from 3, to 8 carbon atoms, and containing an epoxy or —CH$_2$-epoxy, or

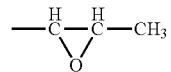

function.

As indicated above: the expression "branched alkyl group" includes "a conventional branched alkyl group and an alkyl group including a cycloalkyl (with one of the carbon atoms of the alkyl chain also belonging to said cycloalkyl")" and, according to advantageous, independent variants:

Z is linear;

Z contains said epoxy function at the chain end;

said advantageous variants, taken in combination, constituting a very advantageous variant (Z, (C$_2$-C$_8$)alkyl, linear, containing said epoxy function at the chain end, i.e. $R_3$=—O—[CH$_2$—]n-epoxy with n, an integer from 0, advantageously from 1, to 6).

Similarly, and in a non-limiting way, some values of Z can be recalled:

Z=—[CH$_2$]$_n$-epoxy, with n an integer from 0 to 6, advantageously from 1 to 6 and in particular n=4, very advantageously n=1;

Z=—CH$_2$—CH(CH$_3$)—CH$_2$—CH$_2$-epoxy,

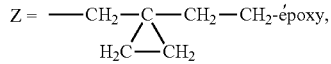

and

Z=CH$_2$—C(CH$_3$)$_2$—CH$_2$—CH$_2$-epoxy.

Similarly, according to a preferred variant, Z=—[CH$_2$-]$_n$-epoxy with 1 n 4 and according to a particularly preferred variant, Z=—CH$_2$-epoxy (and thus corresponding values of $R_1$=$R_2$=—CH$_2$—O—Z, or —O—Z, or —COO—Z).

Thus:

g) in the context of its first subject matter, the present invention therefore also relates to biphenyl compounds of formula (I) wherein: $R_3$=—O-Alk' (advantageously —O—CH$_3$ (see above)) and $R_1$=$R_2$=—CH$_2$—O—Z, with Z as defined above. These compounds are compounds derived from alkylated divanillyl alcohol. The present invention particularly relates to said compounds of formula (I) with $R_3$=—O-Alk' (advantageously —O—CH$_3$ (see above)) and $R_1$=$R_2$=—CH$_2$—O—[CH$_2$-]$_n$-epoxy (with n, an integer from 0, advantageously from 1, to 6). It relates in particular to said compounds with $R_3$=—O-Alk' (advantageously —O—CH$_3$ (see above)) and $R_1$=$R_2$=—CH$_2$—O—CH$_2$-epoxy, and in particular to the diglycidyl ether of methylated divanillyl alcohol (DiGEmDVA) of formula:

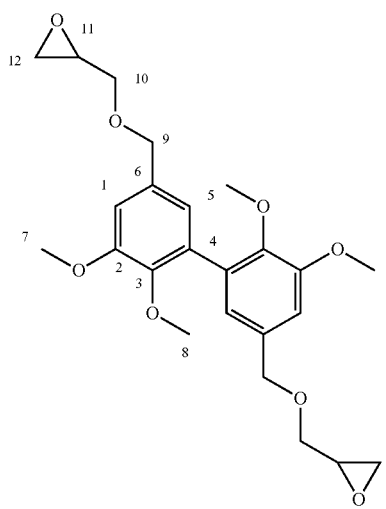

DiGEmDVA h) in the context of its first subject matter, the present invention therefore also relates to biphenyl compounds of formula (I) wherein: $R_3$=—O-Alk' (advantageously —OCH$_3$ (see above)) and $R_1=R_2$=—O—Z, with Z as defined above. These compounds are compounds derived from alkylated dimethoxyhydroquinone. The present invention particularly relates to said compounds of formula (I) with $R_3$=—O-Alk' (advantageously —O—CH$_3$ (see above)) and $R_1=R_2$=—O—[CH$_2$-]$_n$-epoxy (with n, an integer from 0, advantageously from 1, to 6). It particularly relates to said compounds with $R_3$=—O-Alk' (advantageously —O—CH$_3$ (see above)) and $R_1=R_2$=—O—CH$_2$-epoxy, and in particular to the diglycidyl ether of methyl dimethoxyhydroquinone (DiGEmDMHQ) of formula:

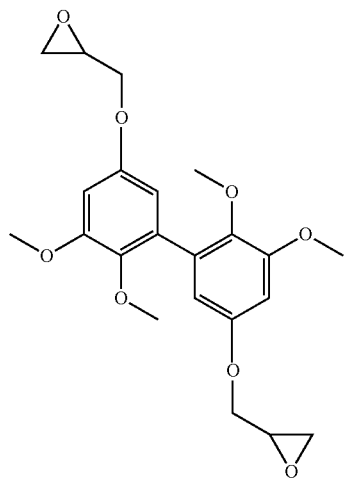

DiGEmDMHQ i) in the context of its first subject matter, the present invention therefore also relates to biphenyl compounds of formula (I) wherein: $R_3$=—O-Alk' (advantageously O—CH$_3$ (see above)) and $R_1=R_2$=—COO—Z, with Z as defined above. These compounds are compounds derived from an alkylated alkyl (ester) divanillate, or from alkylated divanillic acid. The present invention particularly relates to said compounds of formula (I) with $R_3$=—O-Alk' (advantageously —O—CH$_3$ (see above)) and $R_1=R_2$=—COO—[CH$_2$-]$_n$-epoxy (with n, an integer from 0, advantageously from 1, to 6). It particularly relates to said compounds with $R_3$=—O-Alk' (advantageously —O—CH$_3$ (see above)) and $R_1=R_2$=—COO—CH$_2$-epoxy, and in particular to the diglycidyl ether of methylated divanillic acid (DiGEmDVAc) of formula:

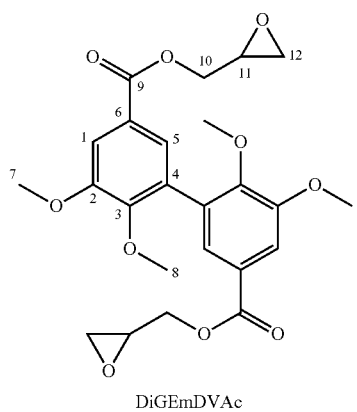

DiGEmDVAc j) in the context of its first subject matter, the present invention therefore also relates to biphenyl compounds of formula (I) wherein: $R_3$=—O-Alk' (advantageously —O—CH$_3$ (see above)) and $R_1=R_2$=—CH$_2$-epoxy. These compounds are compounds derived from alkylated eugenol. The present invention in particular relates to diglycidyl ether of methylated dieugenol (DiGEmDEG) of formula:

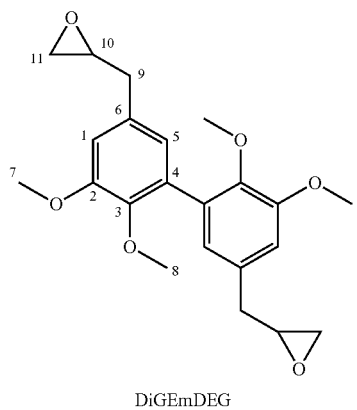

DiGEmDEG k) in the context of its first subject matter, the present invention therefore also relates to biphenyl compounds of formula (I) wherein: $R_3$=—O-Alk' (advantageously OCH$_3$ (see above)) and $R_1=R_2$=

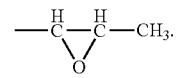

These compounds are compounds derived from alkylated isoeugenol. The present invention relates in particular to diglycidyl ether of methylated diisoeugenol (DiGEmDisoEG) of formula:

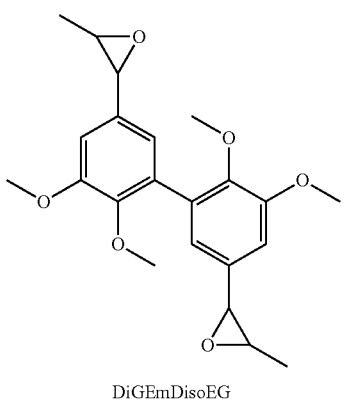

DiGEmDisoEG

The skilled person already understands the great interest of the biphenyl compounds of the invention, as precursors of polyepoxides (as monomers or prepolymers to be polymerized (cross-linked) under the action of a hardener), due to the presence of 2, 3 or 4 epoxy groups (capable of reacting with said hardener) in their formula. Furthermore, the presence of the two aromatic rings has proved of particular interest with reference to the mechanical properties and the temperature resistance of said polyepoxides and the presence of the carbon-carbon bond between said two aromatic rings has proved surprisingly opportune with reference to the rate of residual coke after thermal degradation of said polyepoxides.

It must also be stressed that said compounds can be obtained by non-complex processes and, possibly, for many of these compounds, from natural products such as vanillin, eugenol and isoeugenol (see below).

The preparation of the compounds of formula (I) constitutes another subject matter of the invention.

The preparation process in question advantageously comprises:
a) providing a dimer selected from divanillin, divanillyl alcohol, dimethoxyhydroquinone, divanillic acid, dieugenol, diisoeugenol, said dimers having at least two phenolic —OH functions and two —O—$CH_3$ functions, and analogs of said dimers having said at least two phenolic —OH functions and two —O—($C_2$-$C_6$)alkyl functions,
b) optionally, the alkylation of the phenolic —OH functions of a dimer chosen from divanillin, divanillyl alcohol, divanillic acid, dieugenol, diisoeugenol and their analogs in order to obtain said alkylated divanillin, said alkylated divanillyl alcohol, said alkylated divanillic acid, said alkylated dieugenol, said alkylated diisoeugenol and their alkylated analogs; the alkylation of the divanillin or an analog thereof being followed by oxidation to yield the alkylated di($C_1$-$C_6$)alkoxyhydroquinone; and
c1) in the absence of such alkylation, the epoxidation of the two phenolic —OH functions of divanillin or one of its analogs or the epoxidation of the two, or even three, or even four functions present on the biphenyl nucleus which can be epoxidized, of said divanillyl alcohol, said dimethoxyhydroquinone, said divanillic acid, said dieugenol, said diisoeugenol or one of their analogs; or
c2) following such alkylation, the epoxidation of the two non-alkylated functions, still present on the biphenyl nucleus, of the alkylated divanillyl alcohol, alkylated di($C_1$-$C_6$)alkoxyhydroquinone, alkylated divanillic acid, alkylated dieugenol, alkylated diisoeugenol or one of their analogs.

Said process is illustrated, schematically and in a non-limiting way, in the context of the preparation of compounds of formula (I) in which R=—O—$CH_3$, in FIGS. 1A and 1B. It is understood that the same reaction scheme is suitable for the preparation of compounds of formula (I) in which R=—O—($C_2$-$C_6$)Alk (said R appearing in the formula of the starting material). In said FIGS. 1A and 1B, as well as in the remainder of the present description, poly(2)epoxidized, poly(3)epoxidized and poly(4)epoxidized are obviously equivalent to, respectively, di-epoxidized, tri-epoxidized and tetra-epoxidized, and poly(2,3,4)epoxidized which indicates the possible obtaining of the di-, tri-, tetra-epoxidized compounds while poly(3,4)epoxidized indicates the possible obtaining of the tri- and tetra-epoxidized compounds.

Obviously, when the process generates mixtures of at least two compounds of the invention (see below), it may include a separation step (conventional, and in particular by column chromatography) of said at least two compounds. It may already be stated here that, for the applications in question, both compounds of formula (I) per se and mixtures of compounds of formula (I) are suitable (such mixtures may prove particularly suitable with reference to certain properties of the resins obtained therefrom).

It is intended, regarding the reagents and reactions involved, to provide, in a non-limiting way, the following information.

It is recalled that vanillin (V), eugenol (EG) and isoeugenol (isoEG) are natural products and that therefore, many of the compounds of the invention, obtained from such natural products, are biosourced products. These products—vanillin, eugenol and diisoeugenol—as well as products with relatively similar formulas (vanillin esters (VE), vanillin analogs with a $C_2$-$C_6$ alkoxy group instead of a methoxy group, etc.) can also be obtained by conventional synthesis. Such products, with relatively similar formulas, are marketed, for example methyl vanillate, ethyl vanillin, etc. Such products are certainly also suitable for the implementation of the process as currently described.

The dimerization of such products does not pose any difficulties. Oxidative coupling is involved. The use of laccase from *Trametes versicolor* in such a context has been widely described. For example, Examples 1, 4 and 7 of application EP 3 002 333 illustrate respectively the preparation of divanillin (DV), methyl divanillate (DVE) and DVE (divanillin ester) in FIG. 1A) and of dieugenol (DEG). Diisoeugenol (DisoEG) can of course be obtained under the same conditions as dieugenol (DEG).

The dimers thus obtained (DV, DVE, DEG and DisoEG) can be alkylated (in particular methylated) for the preparation of the compounds of the invention of formula (I) in which $R_3$=—O-Alk' (in particular $R_3$=—O—$CH_3$). The type of alkylation in question (more precisely etherification in question: —OH becomes $R_3$=—O-Alk') does not pose any difficulty to the skilled person. The bisphenol is brought into contact with a base, such as potassium carbonate, in a solvent (such as dimethylformamide (DMF)) and a iodoalkyl (I-Alk', such as iodomethane) is added slowly. The reaction, at high temperature (for example 80° C.), takes several hours. At the end of the reaction, the reaction medium is advantageously filtered and the alkylated compound is recovered by precipitation in cold water. In the context of the process of the invention, this alkylation can thus be carried out:
on divanillin (DV) to obtain alkylated divanillin (DV') (advantageously methylated divanillin) from which alkylated dimethoxyhydroquinone (DMHQ'), alkylated in its precursor functions of $R_3$ (and not in its precursor functions of $R_1$ and/or $R_2$), can then be prepared by oxidation, said oxidation being described below for the conversion of divanillin (DV) into dimethoxyhydroquinone (DMHQ);

optionally, on a divanillin ester (DVE), in particular methyl divanillate, to obtain said alkylated divanillin ester (DVE'), which alkylated divanillin ester (DVE') can be saponified instead of divanillic acid (DVAc) (see below); (see FIG. 1A)

on dieugenol (DEG) to obtain alkylated dieugenol (DEG'), and on diisoeugenol (DisoEG) to obtain alkylated diisoeugenol (DisoEG') (see FIG. 1B).

The dimers selected from divanillin (DV), alkylated divanillin (DV'), divanillin esters (DVE) and alkylated divanillin esters (DVE') can be converted into other dimers whose formula contains alcohol, hydroxy and acid type functions, functions which can be epoxidized subsequently. Such dimers with such epoxidizable functions, in addition to their (epoxidizable) phenolic —OH functions, are of particular interest in that they are potential precursors of compounds of formula (I) with three or four epoxy functions.

Concerning divanillin (DV) (see FIG. 1A):

its aldehyde functions can be reduced by the conventional use of a sodium borohydride reducer. Such a reaction is illustrated in Example 8 of application EP 3 002 333. It leads to divanillyl alcohol (DVA), which can be alkylated according to the alkylation reaction described above. Said divanillyl alcohol (DVA) contains four epoxidizable functions (its two phenolic —OH functions and its two alcohol functions —$CH_2OH$), said alkylated divanillyl alcohol (DVA') contains two epoxidizable functions (its two alcohol functions —$CH_2OH$);

it can be oxidized according to the Dakin oxidation reaction to yield dimethoxyhydroquinone (DMHQ): sodium percarbonate is slowly added to an aqueous soda solution containing said divanillin (DV). The reacted medium is then acidified. The dimethoxyhydroquinone (DMHQ) formed is recovered by extraction with a solvent (such as ethyl acetate). Said dimethoxyhydroquinone (DMHQ) contains four epoxidizable phenolic —OH functions. The selective alkylation of two of said functions is difficult to manage; this is why the prior alkylation of divanillin (DV) was recommended above. It is understood that the Dakin oxidation reaction carried out on the alkylated divanillin (DV') leads to the alkylated dimethoxyhydroquinone (DMHQ') ($R_3$-alkylated) which has two phenolic —OH epoxidizable functions (and two alkylated —OH functions);

it can also be oxidized to divanillic acid (DVAc). Said acid (DVAc) is obtained from divanillin (DV) by oxidation in a basic medium and in the presence of a homogeneous oxidation catalyst, such as $AgNO_3$. Said divanillic acid (DVAc) contains four epoxidizable functions (its two phenolic —OH functions and its two acid functions —COOH). It can be alkylated, under the conditions indicated above, to produce alkylated divanillic acid (DVAc') which, in turn, contains only two epoxidizable functions (its acid functions —COOH).

Divanillin esters (DVE) and their possible alkylation to obtain such alkylated divanillin esters (DVE') have been discussed above. From said esters (DVE) and alkylated esters (DVE'), divanillic acid (DVAc) and alkylated divanillic acid (DVAc'), respectively, can also be obtained. A saponification reaction as illustrated in Example 13 of patent application EP 3 002 333 (in the presence of KOH and methanol)) is involved (see FIG. 1A). More generally, saponification is carried out in an alcoholic medium in the presence of a strong base.

Incidentally, it should be noted that purification steps can be carried out after obtaining the dimers and/or alkylated dimers.

Next comes the epoxidation of the resulting dimers —DV, DVA, DVA', DMHQ, DMHQ', DVAc, DVAc' (FIG. 1A), DEG, DEG', DisoEG, DisoEG' (FIG. 1B).

In general, epoxidation (of an epoxidizable function, in the present context of alcohol, hydroxy, acid, double bond) is recommended according to one or other of the following methods:

by reaction with epichlorohydrin or equivalent (this reaction has been named Ep.1 in the annexed FIGS. 1A and 1B), i.e. by reaction with a compound of formula Cl—Z, with Z having the definition given for the compounds of formula (I), namely a linear or branched alkyl group containing from 2, advantageously from 3, to 8 carbon atoms and containing an epoxy function. It is recalled here that, in a non-limiting way, according to advantageous, independent variants:

Z is linear,

Z contains said epoxy function at the chain end;

said advantageous variants, taken in combination, constituting a very advantageous variant (Z, ($C_2$-$C_8$)alkyl, linear, containing said epoxy function at the chain end, i.e. Z=—[$CH_2$-]$_n$-epoxy with n, an integer from 0, advantageously from 1, to 6).

The Z values already indicated are also recalled:

Z=—[$CH_2$]$_n$-epoxy, where n is an integer from 0 to 6, advantageously from 1 to 6 and in particular n=4, advantageously n=1, Z=—$CH_2$—CH($CH_3$)—$CH_2$—$CH_2$-epoxy,

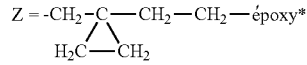

and

Z=—$CH_2$—C($CH_3$)$_2$—$CH_2$—$CH_2$-epoxy.

Thus, among the "epichlorohydrins" of formula Cl—Z, suitable for the desired epoxidations, those corresponding to the formulas hereafter: Cl—[$CH_2$]$_n$-epoxy, with n an integer from 0 (2-chloro oxirane) to 6, advantageously from 1 (epichlorohydrin) to 6, according to a preferred variant 1≤n≤4, and in particular n=4*, according to a particularly preferred variant n=1 (epichlorohydrin), Cl—$CH_2$—CH($CH_3$)—$CH_2$—$CH_2$-epoxy*,

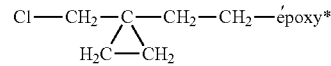

and

Cl—$CH_2$—C($CH_3$)$_2$—$CH_2$—$CH_2$-epoxy* are widely advocated.

Those marked with an asterisk are commercially available from Enamine BB. The use of epichlorohydrin (Cl—$CH_2$-epoxy) is particularly recommended. Said epichlorohydrin is marketed in particular by Solvay. It is essentially synthesized from propylene. The epoxidation reaction in question (with the Cl—Z reagent) takes place in two stages. First, under the action of heat, in the presence of a phase transfer catalyst (such as, for example, tetrabutylammonium bromide (TEBAC)), the nucleophilic substitution of —OH by the Cl—Z compound is facilitated (by assisting the phenolate ion in the organic phase). Generally, no solvent is required since the Cl—Z compound acts as a solvent. The reaction medium is then cooled and soda is added. The inventors have shown (see below, including the examples) that this epoxidation reaction can be controlled and lead, more or less selectively, to mixtures of di-, tri- and/or tetra-epoxidized compounds. The influential parameters are essentially the amount of sodium hydroxide and the duration of the second part of the reaction in the presence of sodium hydroxide;

by the succession of two reactions, a first allylation reaction (conventional allylation with an allyl halide of the allyl bromide type: X-allyl (as illustrated in Example 19 of EP 3 002 333) (known as the Williamson reaction) or "green" allylation with allyl methyl carbonate as described in Chem. Common, 2017, 53, 5175-5178 (known as Tsuji-Trost allylation); the allyl group, precursor of the group Z (of formula (I)), comprising from 2, advantageously from 3, to 8 carbon atoms) and a second epoxidation reaction proper (epoxidation of the double bond introduced by said allyl halide or said allyl methyl carbonate: epoxidation using an oxidant, such as meta-chloroperoxybenzoic acid or oxone). This succession of the two reactions has been called "allylation+Ep.2" in the appended FIGS. 1A and 1B. It is understood that the allyl group allows the conversion of alcohol, hydroxy and acid functions into, respectively, —$CH_2$—O-allyl, —O-allyl and —COO-allyl functions and that said allylated functions are all susceptible to be epoxidized (the double bonds, present at the chain end or not, being then converted into epoxy groups). It is understood that the epoxidized allyl group corresponds to group Z of formula (I). The epoxidation of the allyl functions provided can in fact also be controlled, by managing the amount of oxidant and the duration of the epoxidation reaction (in the presence of said oxidant), so that it can be partial (in which case it does not concern all the double bonds provided) or total (in which case it concerns all the double bonds provided). It is thus possible to obtain mixtures of at least two partially epoxidized allyl compounds, at least one partially epoxidized allyl compound and the fully epoxidized allyl compound (compound of isolatable formula (I)). After a total epoxidation which is easy to carry out (with sufficient amount of oxidant and sufficient duration of the epoxidation reaction (of the double bonds provided)), it is possible to obtain directly said totally epoxidized allyl compound (of formula (I));

by oxidative epoxidation (second reaction (epoxidation reaction proper) indicated above and referred to as Ep.2 in FIG. 1B) of double bonds present in the formula of the molecule in question. Here, of course, thought is given to the —$CH_2$—CH=$CH_2$ functions of dieugenol (DEG), poly(2) epoxidized dieugenol (DEG) and alkylated dieugenol (DEG') and to the —CH=CH—$CH_3$ functions of diisoeugenol (DisoEG), poly(2)epoxidized diisoeugenol (DisoEG) and alkylated diisoeugenol (DisoEG') (see below). Such epoxidations, as indicated above, may be total or partial. Advantageously, they are total.

With regard to this epoxidation step (which, in order to epoxidize several types of functions of the same dimer, may take place in several epoxidation "phases" (for example, epoxidation of —OH functions followed by epoxidation of at least one double bond)) as generally described above, the following clarifications can be made, for all practical purposes, with reference to each dimer in question.

Divanillyl alcohol (DVA) and alkylated divanillyl alcohol (DVA') are opportunely, in the context of the invention, epoxidized according to the first or second of the epoxidation methods presented above. There are respectively, for DVA, two epoxidizable phenolic —OH functions as well as two epoxidizable —$CH_2$—OH functions and, for DVA', two epoxidizable —$CH_2$—OH functions. The inventors have shown that it is possible, from divanillyl alcohol (DVA) to obtain, according to the first of said methods, mixtures of two or three multi-epoxidized DVAs selected from di-epoxidized DVA ($R_3$=—O—Z (—OH epoxidized by Cl—Z)) and $R_1$=$R_2$=—$CH_2$—OH (non-epoxidized), tri-epoxidized DVA ($R_3$=—O—Z (—OH epoxidized by Cl—Z) and $R_1$ or $R_2$=—$CH_2$—O—Z (—$CH_2$—OH epoxidized by Cl—Z) and tetra-epoxidized DVA ($R_3$=—O—Z (—OH epoxidized by Cl—Z) and $R_1$=$R_2$=—$CH_2$—O—Z (—$CH_2$—OH epoxidized by Cl—Z)); and this with control of the composition of said mixtures, as indicated above, by influencing the amount of sodium hydroxide added and the duration of the reaction with said sodium hydroxide. This is illustrated by Example 1 below, in which Cl—Z is epichlorohydrin. However, the general definition of Z is recalled, as well as the preferred definitions, given in a non-limiting way, for example Z=—[$CH_2$]$_n$-epoxy. It is understood here how the compounds of the invention of subfamily a, presented above, can be obtained. It is specified, for all practical purposes, that, if necessary, this or that multi-epoxidized DVA can be isolated (in particular by column chromatography) from a mixture containing it. As indicated above, to obtain the poly(4)epoxidized DVA, it is also quite possible to carry out successively the two allylation steps (Williamson or Tsuji-Trost reaction) and (total) oxidative epoxidation. Partial epoxidation leads to partially epoxidized allylated intermediate products. Starting from alkylated divanillyl alcohol (DVA'), for the epoxidation of its two alcohol functions (—$CH_2$—OH), one can also proceed, as indicated above, according to either of the first and second epoxidation methods specified above (reaction with epichlorohydrin (illustrated in Example 6 below) or equivalent (Cl—Z), or allylation (conventional or green, which introduces an allyl group)+(proper, (total) oxidative epoxidation). It is understood here how the compounds of the invention of sub-family g, presented above, can be obtained.

Divanillin (DV) has its two phenolic —OH functions which can be epoxidized. For this epoxidation, it is also possible to proceed according to either of the first and second epoxidation methods specified above (reaction with epichlorohydrin (illustrated in Example 2 below) or equivalent (Cl—Z), or allylation (conventional or green, which introduces an allyl group)+epoxidation (proper, oxidative (total)). It is understood here how the compounds of the invention of sub-family b, presented above, can be obtained.

Dimethoxyhydroquinone (DMHQ) and alkylated dimethoxyhydroquinone (DMHQ') are opportunely, in the context of the invention, epoxidized according to the first (reaction with epichlorohydrin (illustrated in Example 3 below) or equivalent (Cl—Z)) or the second (allylation (conventional or green, which introduces an allyl group)+epoxidation (proper, oxidative) of the epoxidation methods presented above. There are respectively, for DMHQ, four epoxidizable phenolic —OH functions and, for DMHQ', two epoxidizable phenolic —OH functions. The inventors also showed that epoxidation with epichlorohydrin or equivalent could give mixtures of variable composition in poly(2,3,4) epoxidized DMHQ compounds, depending on the amount of sodium hydroxide added and the duration of the reaction with said sodium hydroxide. In the present case, it is more difficult to control the composition of said mixtures. It is, however, always possible to selectively extract (in particular by chromatography) from these mixtures poly(2,3,4)epoxidized DMHQs. It is understood here how the compounds of the invention of subfamily c, presented above, can be obtained. As indicated above, in order to obtain the poly(4) epoxidized DMHQ, it is also quite possible to carry out successively the two allylation steps (Williamson or Tsuji-Trost reaction) and (total) oxidative epoxidation. Partial epoxidation leads to partially epoxidized allylated intermediate products. Starting from alkylated dimethoxyhydroquinone (DMHQ'), for the epoxidation of its two non-alkylated phenolic —OH functions, it is also possible to proceed, as indicated above, according to either of the first and second epoxidation methods specified above (reaction with epichlorohydrin or equivalent (Cl—Z), or allylation (conventional or green, which introduces an allyl group)+((total) oxidative epoxidation). It is understood here how the compounds of the invention of sub-family h, presented above, can be obtained.

Divanillic acid (DVAc) and alkylated divanillic acid (DVAc') are opportunely, in the context of the invention, epoxidized according to the first (reaction with epichlorohydrin (illustrated in Example 4 below) or equivalent (Cl—Z)) or the second (allylation (conventional or green, which introduces an allyl group)+epoxidation (proper, oxidizing) of the epoxidation methods presented above. There are respectively, for DVAc, two epoxidizable phenolic —OH functions and two epoxidizable —COOH functions and, for DVAc', two epoxidizable —COOH functions. The inventors also showed that epoxidation with epichlorohydrin or equivalent could give mixtures of variable composition in poly(2,3,4)epoxidized DVAc compounds, depending on the amount of sodium hydroxide added and the duration of the reaction with said sodium hydroxide. From a ternary or binary mixture containing them, the poly(2)epoxidized, poly(3)epoxidized and poly(4)epoxidized compounds can be isolated (in particular by column chromatography). It is understood here how the compounds of the invention of subfamily d, presented above, can be obtained. As indicated above, in order to obtain the poly(4)epoxidized DVAc, it is quite possible to carry out successively the two allylation steps (Williamson or Tsuji-Trost reaction) and (total) oxidative epoxidation. Partial epoxidation leads to partially epoxidized allylated intermediate products. Starting from alkylated divanillic acid (DVAc'), for the epoxidation of its two non-alkylated phenolic —OH functions, it is also possible to proceed, as indicated above, according to either of the first and second epoxidation methods specified above (reaction with epichlorohydrin or equivalent (Cl—Z), or allylation (conventional or green, which introduces an allyl group)+epoxidation (proper, oxidative (total) epoxidation). It is understood here how the compounds of the invention of sub-family i, presented above, can be obtained.

Concerning dieugenol (DEG) (respectively alkylated dieugenol (DEG')) and diisoeugenol (DisoEG) (respectively alkylated diisoeugenol (DisoEG')), their epoxidation can be seen to follow the same reaction scheme (see FIG. 1B). The following are some comments on the epoxidation of dieugenol (DEG) and alkylated dieugenol (DEG'). They are obviously directly applicable to the epoxidation of diisoeugenol (DisoEG) and alkylated diisoeugenol (DisoEG').

Dieugenol (DEG) has four epoxidizable functions: two phenolic —OH functions and two double bonds. It can be poly(2)epoxidized according to the first of the epoxidation methods presented above (reaction with epichlorohydrin (illustrated in Example 5 below) or equivalent (Cl—Z)): its two phenolic —OH functions are then epoxidized. It can also be poly(3) or poly(4) epoxidized in two variants. According to a first variant, the resulting poly(2)epoxidized can itself be epoxidized according to the third epoxidation method above: this is the oxidative epoxidation of at least one of its double bonds. The implementation of this oxidative epoxidation can indeed be controlled to epoxidize a single double bond (partial epoxidation) or (advantageously) both double bonds (total epoxidation) (see also Example 5 below). Incidentally, it should be noted that the order of the two successive epoxidation reactions described above may be reversed. According to a second variant, it is possible to implement the second of the epoxidation methods presented above (allylation (conventional or green, which introduces an allyl group)+epoxidation (proper, oxidative (partial or advantageously total)) directly on the dieugenol. At the end of the allylation step, the dimer has four double bonds: the two original ones from dieugenol (DEG) and the two introduced by allylation. It is conceivable that the four functions which possess a double bond can be identical, of the —CH$_2$—CH$_2$=CH$_2$ type (especially if the allylation is implemented with Br—CH$_2$—CH$_2$=CH$_2$) but that this is by no means an obligation. The oxidative epoxidation carried out on the dimer having its four double bonds then generates poly(3,4)epoxidized DEG (poly(3)epoxidized DEG (partial epoxidation) and/or poly(4)epoxidized DEG (total epoxidation)). It is understood here how the compounds of the invention of subfamilies e (and f), presented above, can be obtained. If the phenolic —OH functions of the dieugenol (DEG) have been previously alkylated, the alkylated dieugenol (DEG') has only its two double bonds as epoxidizable functions. These are epoxidized according to the third epoxidation method above: (total) oxidative epoxidation. The poly(2)epoxidized alkylated dieugenol (poly(2)epoxidized DisoEG') is then obtained. It is understood here how the compounds of the invention of subfamilies j (and k), presented above, can be obtained. Incidentally, it should be noted that the epoxidation of the double bonds of diisoeugenol (DisoEG), whether alkylated or not, certainly leads to compounds of the invention in which at least some of the epoxy functions are not at the chain end.

In consideration of the above description of the process, and especially the second of the epoxidation methods presented above (allylation (conventional or green, which introduces an allyl group)+epoxidation (proper, (partial) oxidative)), intermediate products have been disclosed:

intermediate allylated products of allylated DVA type (poly(4)allylated DVA), allylated alkylated DVA (poly(2)allylated DVA'), allylated DV (poly(2)allylated DV), allylated DMHQ (poly(4)allylated DMHQ), allylated alkylated DMHQ (poly(2)allylated DMHQ'), allylated DVAc (poly(4)allylated DVAc), allylated alkylated DVAc (poly(2)allylated DVAc'), allylated DEG (poly(2)allylated DEG=a tetra-allylated biphenyl compound), allylated DisoEG (poly(2)allylated DisoEG=another tetra-allylated biphenyl compound). For all intents and purposes, it should be remembered that the allyl group, the precursor of group Z (in formula (I)), has from 2, advantageously from 3, to 8 carbon atoms. Said allyl group advantageously consists of the group —[CH$_2$]$_m$—CH=CH$_2$ (with m an integer from 0, advantageously from 1, to 6), very advantageously of the group —CH$_2$—CH=CH$_2$; and some of said partially epoxidized allylated intermediates, i.e., in which not all of the allyl functions have been epoxidized, for example said poly(4)allylated DVA (or DMHQ or DVAc) in which only one, two or three of the allyl functions have been epoxidized, said poly(2) allylated DV (or DVA' or DMHQ' or DVAc') in which only one of the allyl functions has been epoxidized, said poly(2)allylated DEG or poly(2)allylated DisoEG in which only one of the allyl functions has been epoxidized.

Said allylated intermediate products and partially epoxidized allylated intermediate products form an integral part of the present invention.

According to another of its subject matters, the present invention relates to thermosetting epoxy resins containing at least one of the multi-epoxidized biphenyl compounds of formula (I) as described above and/or at least one of the multi-epoxidized biphenyl compounds of formula (I) prepared according to the process described above. In addition to said at least one epoxidized biphenyl compound, said resins may contain additives and/or diluent(s). It is recalled that said compounds—isolated or in a mixture—are particularly suitable as substitutes for DGEBA (see the introduction to the present text as well as the examples below). Said resins are thermosetting due to the presence of the epoxy functions of the compounds of formula (I) (advantageously located at the chain end, very advantageously located at the end of linear chains, preferably located at the end of short linear chains (see above 1≤n≤4 and particularly preferably n=1), each of said compounds of formula (I) containing at least two epoxy functions. These epoxy functions are, in a manner known per se, cross-linkable under the action of heat and in the presence of a curing agent (cross-linking polymerizing agent or (bifunctional) cross-linking agent). The skilled person knows such agents, which are widely used with epoxy resins of the prior art (in particular those based on DGEBA). We quote here, in a non-limiting way, diaminodiphenyl sulfone (DDS), isophorone diamine (IPDA), dicyandiamide, 4,4-methylene-bis(2-isopropyl-6-methylaniline) (in particular marketed by Loza Ltd, under the trade name Lonzacure® M-MIPA), and 4,4'-methylene-bis(2,6-diisopropylamineaniline) (marketed by Loza Ltd. under the trade name Lonzacure® M-DIPA).

According to another of its subject matters, the present invention relates to the thermoset epoxy resins obtained (=the polyepoxides obtained) by heat treatment, in the presence of at least one thermosetting agent, of a thermosetting epoxy resin of the invention. It is understood that the compounds of the invention have been designed as precursors of said thermoset epoxy resins, as precursors of said polyepoxides. The latter object of the present invention can be analyzed as a use of the multi-epoxidized biphenyl compounds, the first subject matter of said invention, said compounds therefore being perfectly suitable (see the properties of the polyepoxides given in the examples) as precursor monomers of such polyepoxides. Said compounds, associated with at least one hardener, are perfectly suitable as epoxy materials (advantageous substitutes for DGEBA) for applications in the fields of adhesives and composites.

The invention is now illustrated by the following examples and the appended figures.

FIGS. 3A to 13A are $^1$H NMR spectra of compounds (or mixtures of compounds) of the invention prepared in the following examples; FIGS. 3B to 13B are $^{13}$C NMR spectra of compounds of the invention prepared in the following examples (however, there is no FIG. 7B).

Figure 1A:
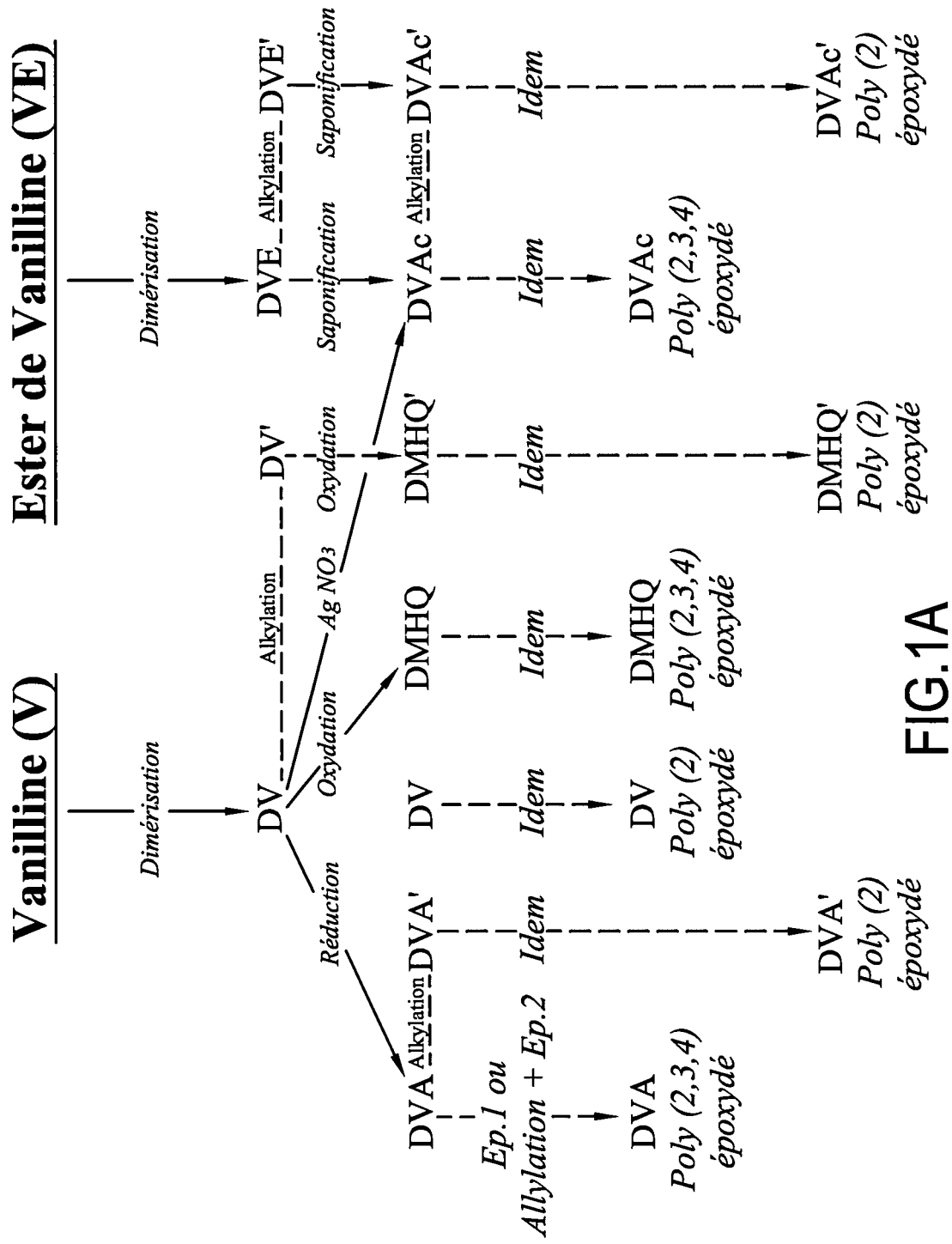
FIGS. 1A and 1B are diagrams illustrating the process of the invention as described above.
Figure 1B:
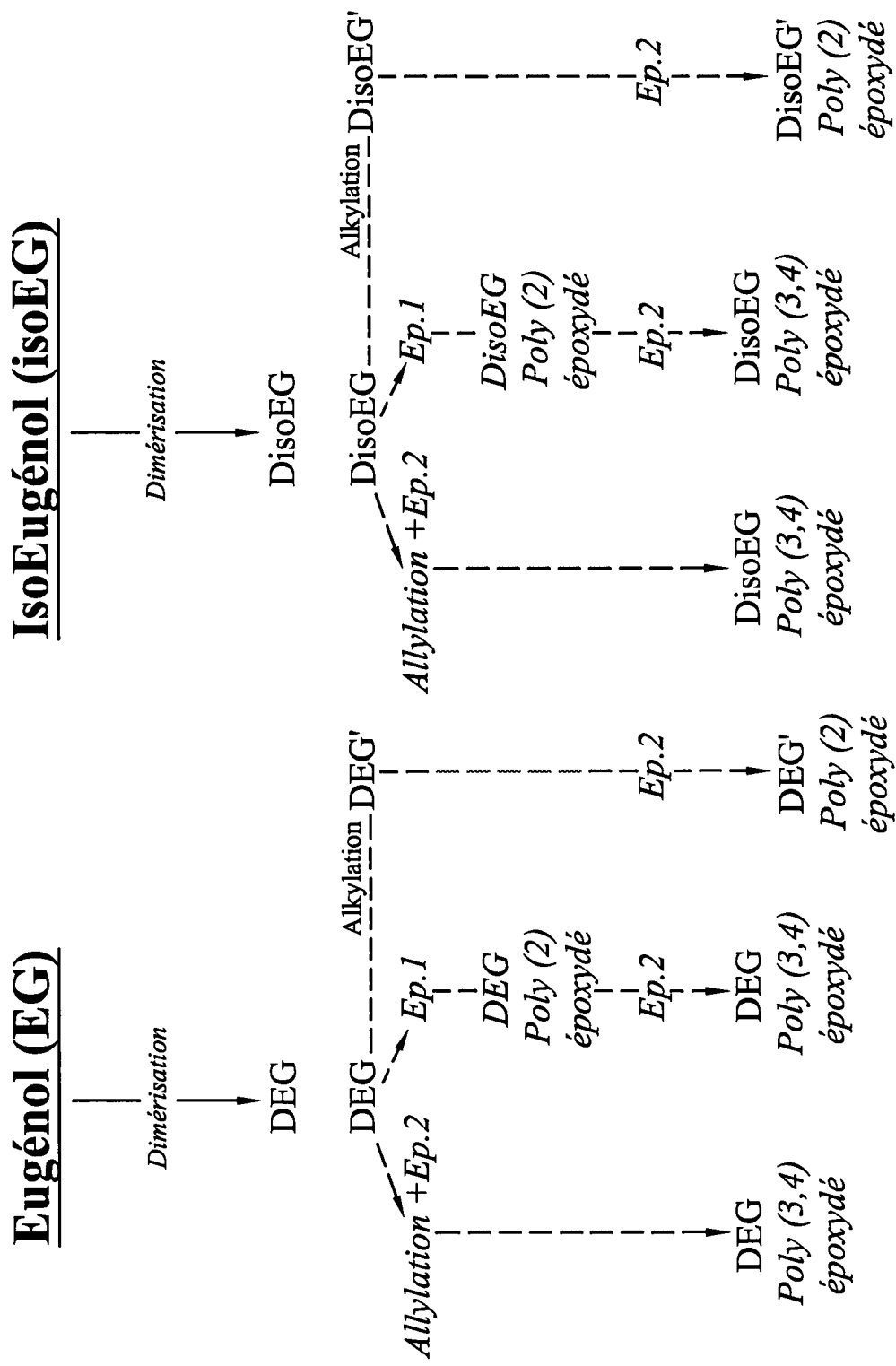

I. COMPOUNDS OF FORMULA (I), IN WHICH $R_3$=O—$CH_2$-EPOXY, DERIVATIVES OF VANILLIN, METHYL VANILLATE OR EUGENOL (ISOLATED AND/OR AS A MIXTURE)

Example 1

A1. Synthesis of Compounds of Formula (I) from Divanillyl Alcohol (DVA)

The different steps of the reaction scheme below have been successively implemented.

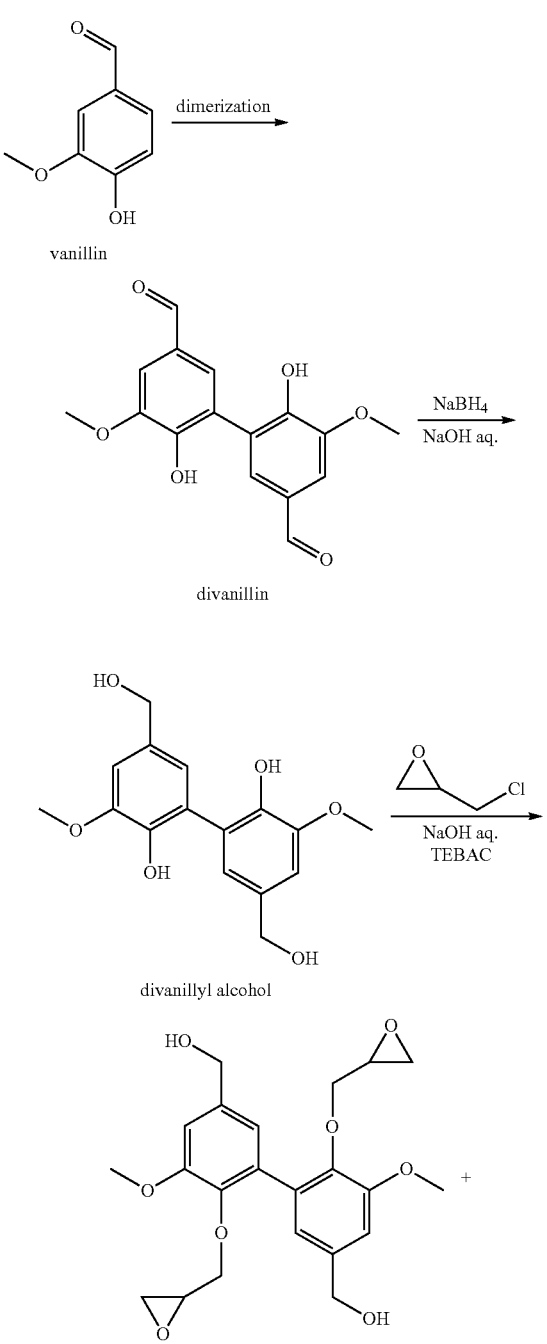

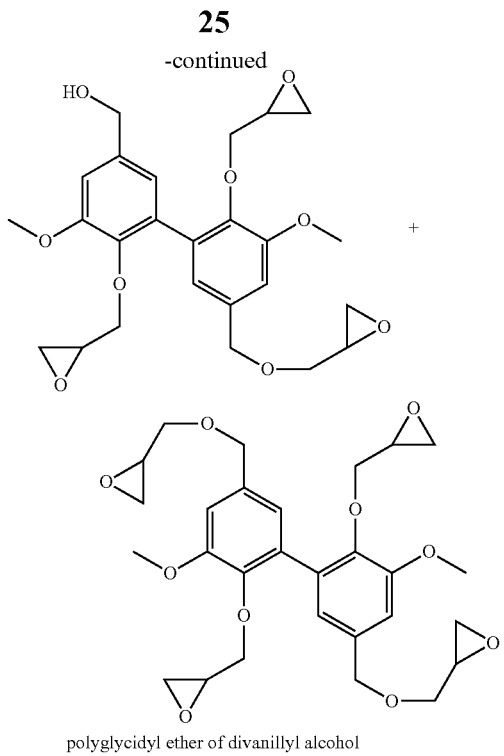

polyglycidyl ether of divanillyl alcohol

Synthesis of Divanillin (DV)

The preparation of divanillin was carried out according to the procedure described in Example 1 of patent application EP 3 002 333. Specifically, the following procedure was followed.

Vanillin (20 g) (the one used, marketed by the company Acros, was not biosourced. For all intents and purposes, it is indicated that the biosourced vanillin marketed by Borregaard could have been used) was solubilized in acetone (160 mL) and acetate buffer (1.5 L, prepared from 2.63 g acetic acid and 8.4 g sodium acetate). Laccase from *Trametes versicolor* (170 mg) was added to the resulting mixture. In order to be recycled in active form, said laccase requires oxygen. The reaction medium was therefore left under stirring with constant air bubbling for 24 hours. The divanillin was then recovered by filtration of the buffer solution through a Büchner filter. The filtrate was recovered and reused for further dimerization reactions.

Purification of Synthesized Divanillin (DV)

Traces of vanillin were likely to be present in the recovered divanillin. To remove them, said divanillin was solubilized in an aqueous solution of NaOH (200 mL at 0.5 M; a few drops of 5 M solution were conveniently added to facilitate solubilization). A large volume of ethanol (600 mL) was then added to the solution as well as an aqueous solution of hydrochloric acid (115 mL at 2 M) until pH=3 was reached for the mixture. Both divanillin and vanillin are soluble at basic pH in ethanol. Divanillin, on the other hand, is not soluble in ethanol at acidic pH, unlike vanillin. The addition of acid therefore allows the two products to be separated by precipitation of divanillin.

The resulting product was filtered and dried in an oven to remove all traces of solvent. The synthesis and purification operations were repeated. The yield was approximately 95% each time.

Obtaining divanillin (DV) was confirmed by NMR spectroscopy:

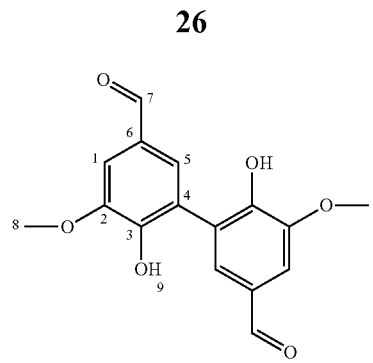

$^1$H NMR (400 MHz, DMSO-d6, δ (ppm): δ 9.69 (s, H$_7$), 7.57 (d, H$_1$), 7.16 (d, H$_5$), 3.76 (s, H$_8$).

$^{13}$C NMR (400 MHz, DMSO-d6, δ (ppm)): δ 191.62 (s, C$_7$), 150.88 (s, C$_3$), 148.61 (s, C$_2$), 128.64 (s, C$_6$), 128.21 (s, C$_4$), 125.02 (s, C$_5$), 109.6 (s, C$_1$), 56.25 (C$_8$).

Synthesis of Divanillyl Alcohol (DVA)

The preparation of divanillyl alcohol was carried out according to the protocol described in Example 8 of patent application EP 3 002 333. Specifically, the process was as follows.

Purified divanillin (20 g) was reduced with sodium borohydride (NaBH$_4$) to form divanillyl alcohol. It was solubilized in 0.5 M sodium hydroxide solution (180 mL; a few drops of 5 M solution were conveniently added to facilitate solubilization). Then NaBH$_4$ (3 g) was added and the mixture was kept under stirring until completely dissolved. After one hour of stirring, the reaction was stopped by adding, dropwise, an aqueous solution of hydrochloric acid (160 mL at 2 M) until pH=3 was reached. The divanillyl alcohol then precipitated. It was recovered by filtration. The recovered product was dried in an oven. Synthesis was repeated. The yield was approximately 80% each time.

Obtaining divanillyl alcohol (DVA) was confirmed by NMR spectroscopy:

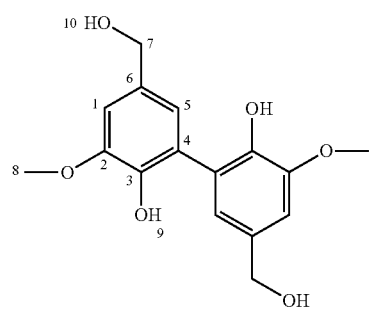

$^1$H NMR (400 MHz, DMSO-d6, δ (ppm)): δ 8.22 (s, H$_9$), 6.88 (d, H$_1$), 6.67 (d, H$_5$), 5.01 (t, H$_{10}$), 4.41 (d, H$_7$), 3.82 (s, H$_8$).

$^{13}$C NMR (400 MHz, DMSO-d6, δ (ppm)): δ 147.94 (s, C$_3$), 142.77 (s, C$_2$), 133.08 (s, C$_6$), 125.92 (s, C$_4$), 121.83 (s, C$_5$), 109.50 (s, C$_1$), 63.38 (s, C$_7$), 56.25 (s, C$_8$).

Synthesis of Compounds of Formula (I) (Multi-Epoxidized Prepolymers)

The last step consisted of epoxidizing divanillyl alcohol (DVA) with epichlorohydrin and resulted in mixtures of different polyglycidyl ethers of divanillyl alcohol. It was used under different conditions to obtain different mixtures.

The multi-epoxidized compounds that could be obtained and whose presence was confirmed (quantitatively and qualitatively) were those with the formula shown in the above reaction scheme, namely:

diglycidyl ether of divanillyl alcohol (DiGEDVA),
triglycidyl ether of divanillyl alcohol (TriGEDVA), and
tetraglycidyl ether of divanillyl alcohol (TetraGEDVA).

a) The experimental conditions used to obtain a mixture of 25% TriGEDVA and 75% TetraGEDVA (% by mass) are described below.

DVA (20 g) was first mixed with epichlorohydrin (100 mL) and tetrabutylammonium bromide (TEBAC) (2 g). TEBAC is a phase transfer agent that allows phenol to react with epichlorohydrin, introduced in excess to form a di-epoxide. The reaction mixture was left to stir at 80° C. for 1.5 hours and then cooled to room temperature.

Subsequently, an aqueous solution of sodium hydroxide (NaOH) (160 mL at 10 M: 10 NaOH eq./OH) was added. The addition of the base closed the open epoxides but also deprotonated the benzyl alcohols which, in turn, were epoxidized by nucleophilic substitution with epichlorohydrin. The solution was then mechanically stirred for 20 h in a cold-water bath.

At the end of the reaction, dichloromethane (DCM) (300 mL) was added to the reaction medium to precipitate the salts (NaCl). The liquid phases were separated from the reaction medium and the salts rinsed with 100 mL DCM. The liquid phases were collected and the aqueous phase was extracted with 2×50 mL DCM. The individual organic phases were collected and washed with 100 mL water. The organic phase was concentrated using a rotary evaporator and the epichlorohydrin was finally evaporated under vacuum. The yield was quantitative. The proportion of di-, tri-, and tetra-epoxidized compounds was quantified by HPLC (high performance liquid chromatography). The apparatus used was a SpectraSYSTEM®, mounted on a Phenomenex 5μ C18 100A column. The detector used was a SpectraSYSTEM® UV2000 system from Thermo Separation Products. The analyses were performed with an eluent composed of acetonitrile and water in a 50/50 isocratic proportion.

Figure 2:
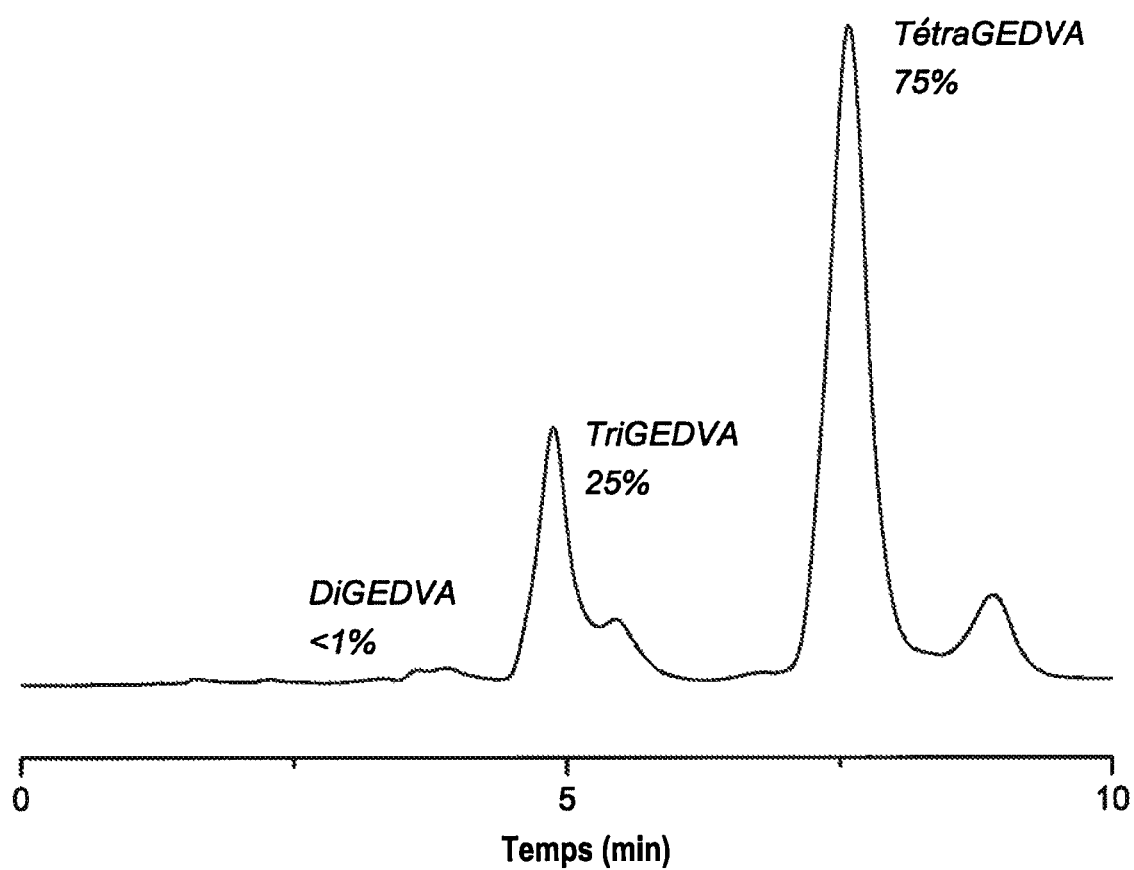
FIG. 2 shows the result of chromatography conducted on a mixture of multi-GEDVAs (see Example 1).

FIG. 2 attached shows the chromatograph obtained.

b) The procedure described in a) above was reproduced (in all respects) but with the addition of an aqueous solution of NaOH (50 mL at 5 M) and with mechanical stirring for only 1 h. A mixture of 80% DiGEDVA, 15% TriGEDVA and 5% TetraGEDVA (% by mass) was then obtained.

c) The procedure described in a) above was repeated (in all respects) but with the addition of an aqueous solution of NaOH (50 mL at 5 M) and with mechanical stirring for only 8 h. A mixture of 35% DiGEDVA, 50% TriGEDVA and 15% TetraGEDVA (% by mass) was then obtained.

In order to obtain, separately, these different compounds of formula (I) (di-, tri- and tetra-epoxidized), a purification step by flash or instantaneous chromatography, on a Grace Reveleris® apparatus, equipped with a silica cartridge and a UV detector, was carried out on the mixtures, using a dichloromethane/methanol solvent gradient from 99/1 to 90/10 (by volume) for 30 minutes.

The identity of said compounds of formula (I) was confirmed by NMR spectroscopy:

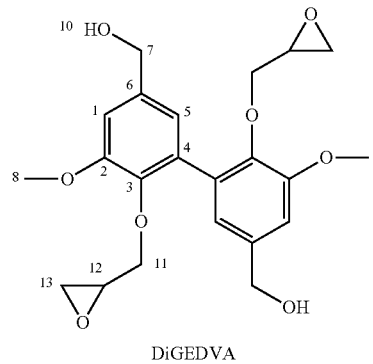

DiGEDVA $^1$H NMR (400 MHz, DMSO-d6, δ (ppm)): δ 7.0 (d, $H_1$), 6.71 (d, $H_5$), 5.16 (t, $H_{10}$), 4.47 (d, $H_7$), 3.88 (m, $H_{11}$), 3.83 (s, $H_8$), 3.74 (m, $H_{11b}$), 2.95 (m, $H_{12}$), 2.6 (t, $H_{13}$), 2.36 (t, $H_{13b}$).

$^{13}$C NMR (400 MHz, DMSO-d6, δ (ppm)): δ 152.33 (s, $C_3$), 144.47 (s, $C_2$), 138.26 (s, $C_6$), 132.59 (s, $C_4$), 120.86 (s, $C_5$), 110.79 (s, $C_1$), 74.22 (s, $C_{11}$), 63.14 (s, $C_7$), 56.18 (s, $C_8$), 50.53 (s, $C_{12}$), 43.97 (s, $C_{13}$).

Figure 3A:
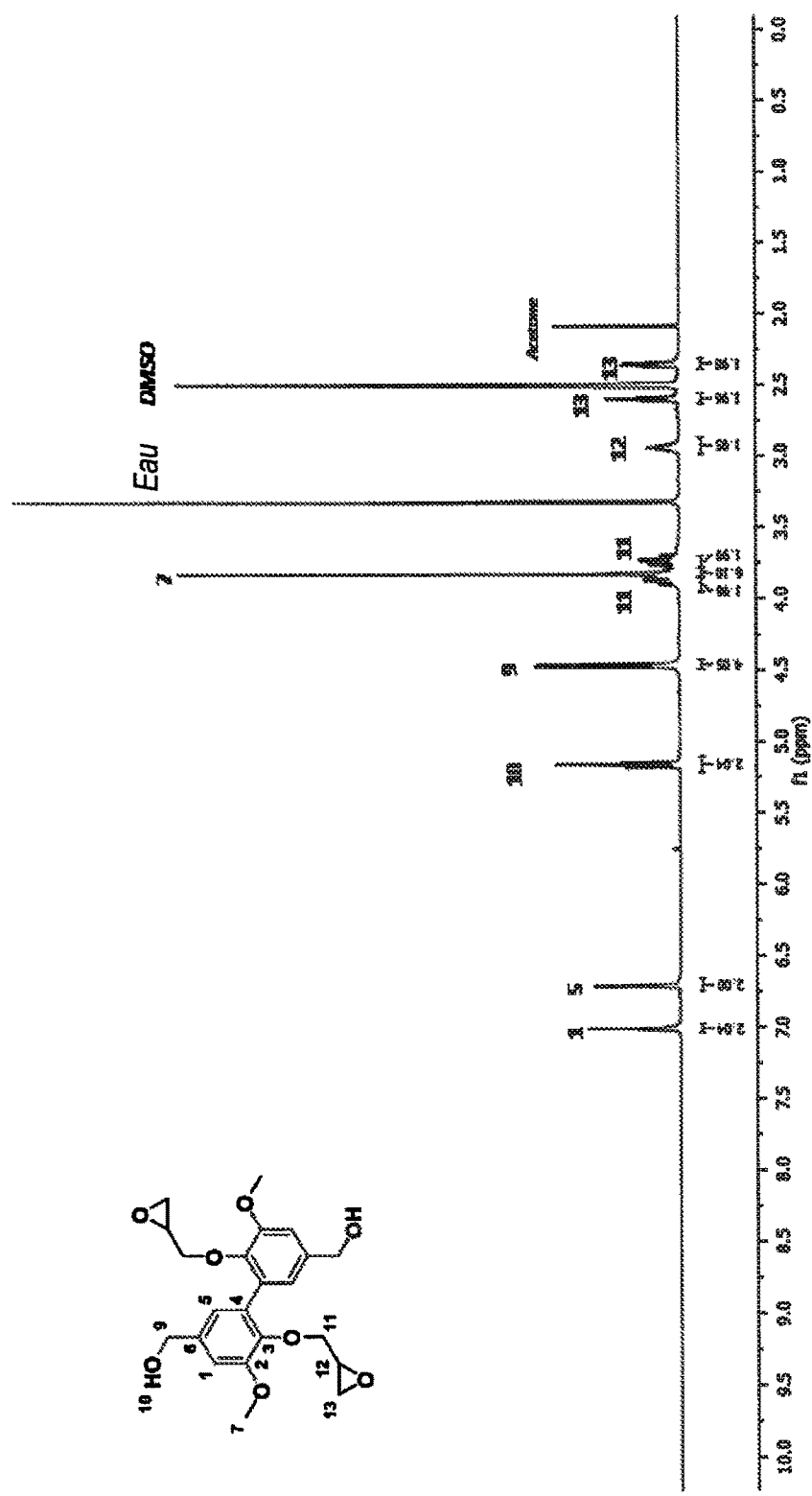
Figure 3B:
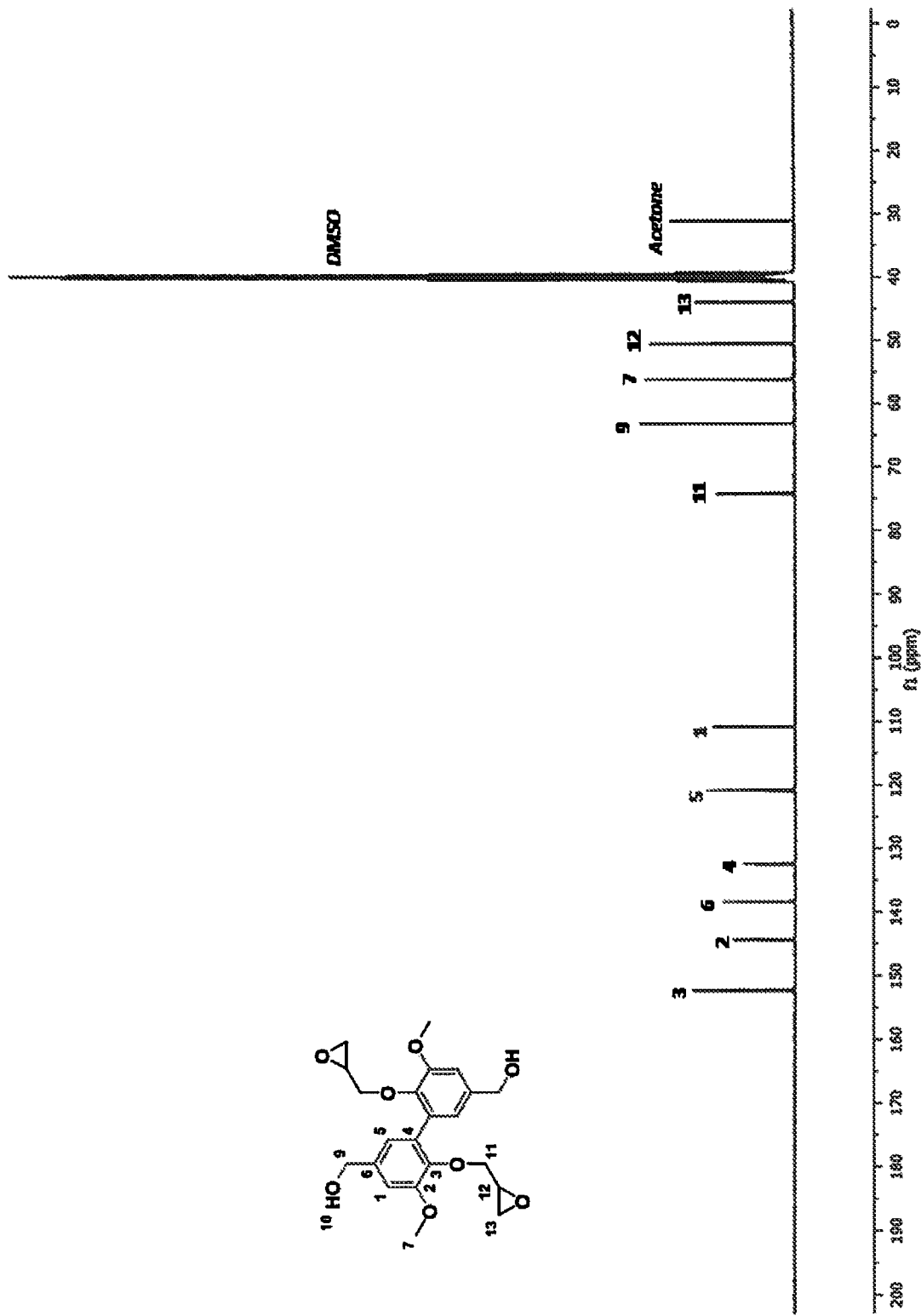

The spectra are shown in FIGS. 3A and 3B respectively.

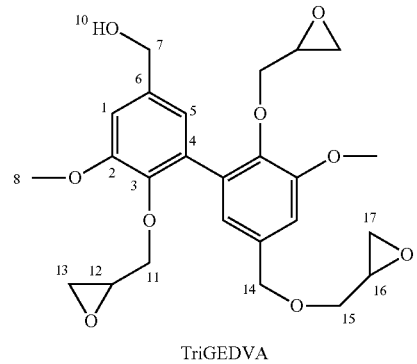 [SMILES: COc1cc(CO)cc(-c2cc(COCC3CO3)cc(OC)c2OCC2CO2)c1OCC1CO1]

TriGEDVA $^1$H NMR (400 MHz, DMSO-d6, δ (ppm)): δ 7.01 (d, $H_1$), 6.75 (d, $H_5$), 5.18 (t, $H_{10}$), 4.47 (d, $H_7$ $H_{14}$), 3.92 (m, $H_{11}$), 3.84 (s, $H_8$), 3.76 (m, $H_{11b}$), 3.69 (m, $H_{15}$), 3.29 (m, $H_{15b}$), 3.14 (m, $H_{16}$), 2.97 (m, $H_{12}$), 2.72 (m, $H_{17}$), 2.6 (m, $H_{13}$), 2.5 (m, $H_{17b}$), 2.36 (m, $H_{13b}$).

$^{13}$C NMR (400 MHz, DMSO-d6, δ (ppm)): δ 152.02 (s, $C_{3'}$), δ 151.89 (s, $C_3$), 144.38 (s, $C_{2'}$), 143.68 (s, $C_2$), 138.12 (s, $C_{6'}$), 133.39 (s, $C_6$), 132.06 (s, $C_{4'}$), 131.76 (s, $C_4$), 121.78 (s, $C_{5'}$), 120.26 (s, $C_5$), 111.55 (s, $C_{1'}$), 110.46 (s, $C_1$), 73.85 (s, $C_{14}$), 71.81 (s, $C_{15}$), 70.79 (s, $C_{11}$), 62.67 (s, $C_7$), 55.90 (s, $C_8$), 50.42 (s, $C_{12}$), 50.16 (s, $C_{16}$), 43.42 (s, $C_{13}C_{17}$).

Figure 4A:
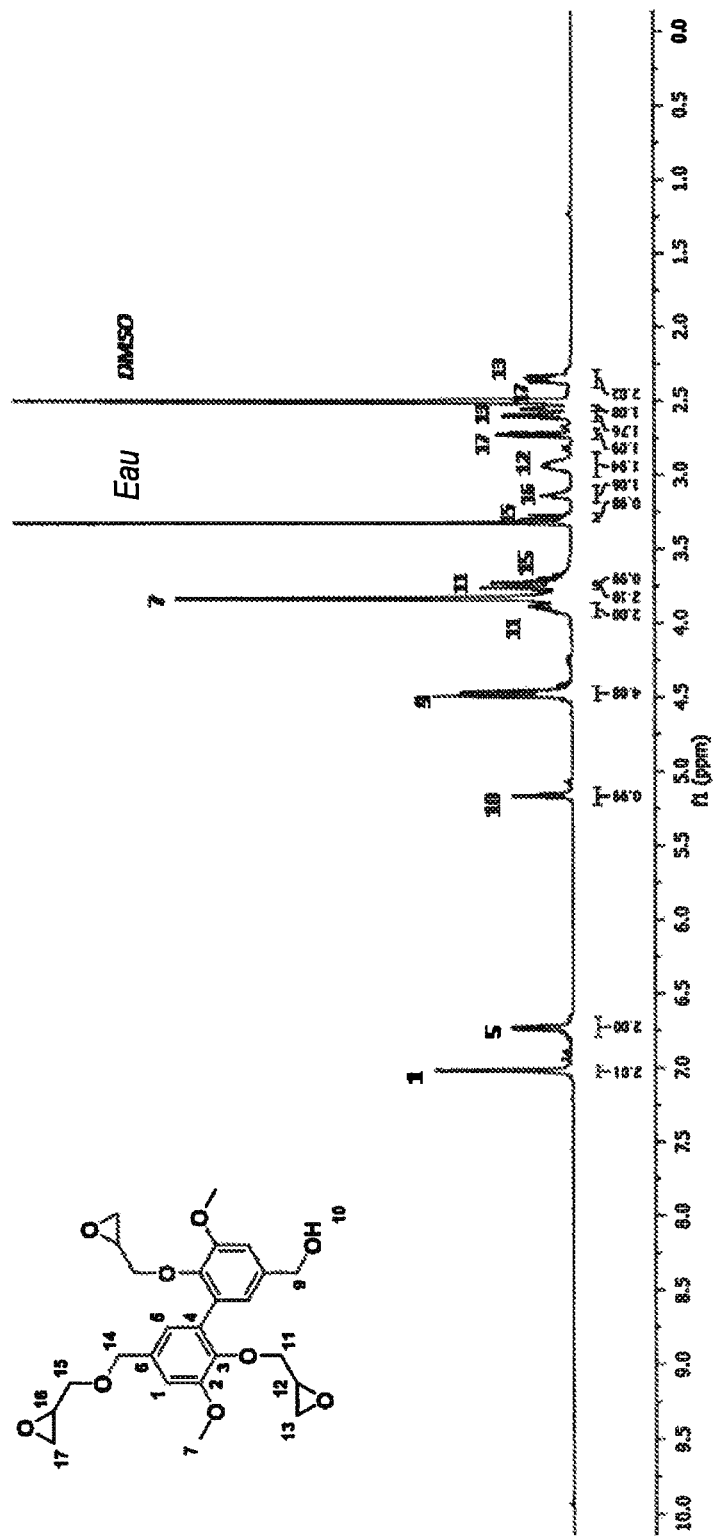

The spectra are shown in FIGS. 4A and 4B respectively.

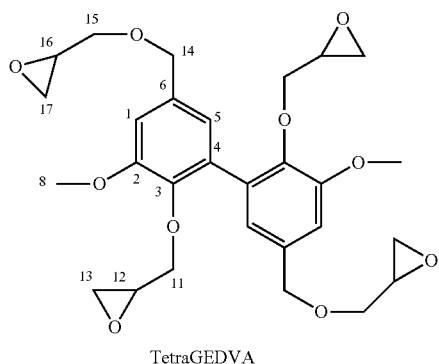 [SMILES: COc1cc(COCC2CO2)cc(-c2cc(COCC3CO3)cc(OC)c2OCC2CO2)c1OCC1CO1]

TetraGEDVA $^1$H NMR (400 MHz, DMSO-d6, δ (ppm)): δ 7.02 (d, $H_1$), 6.76 (d, $H_5$), 4.50 (s, $H_{14}$), 3.92 (m, $H_{11}$), 3.86 (s, $H_8$), 3.76 (m, $H_{11b}$), 3.70 (m, $H_{15}$), 3.28 (m, $H_{15b}$), 3.14 (m, $H_{16}$), 2.97 (m, $H_{12}$), 2.73 (m, $H_{17}$), 2.60 (m, $H_{13}$), 2.55 (m, $H_{17b}$), 2.35 (m, $H_{13b}$).

$^{13}$C NMR (400 MHz, DMSO-d6, δ (ppm)): δ 152.10 (s, $C_3$), 144.51 (s, $C_2$), 133.51 (s, $C_6$), 131.81 (s, $C_4$), 121.83 (s, $C_5$), 111.52 (s, $C_1$), 73.77 (s, $C_{14}$), 71.90 (s, $C_{15}$), 63.14 (s, $C_{11}$), 55.79 (s, $C_8$), 50.30 (s, $C_{12}$), 50.03 (s, $C_{16}$), 43.44 (s, $C_{13}$ $C_{17}$).

Figure 5A:
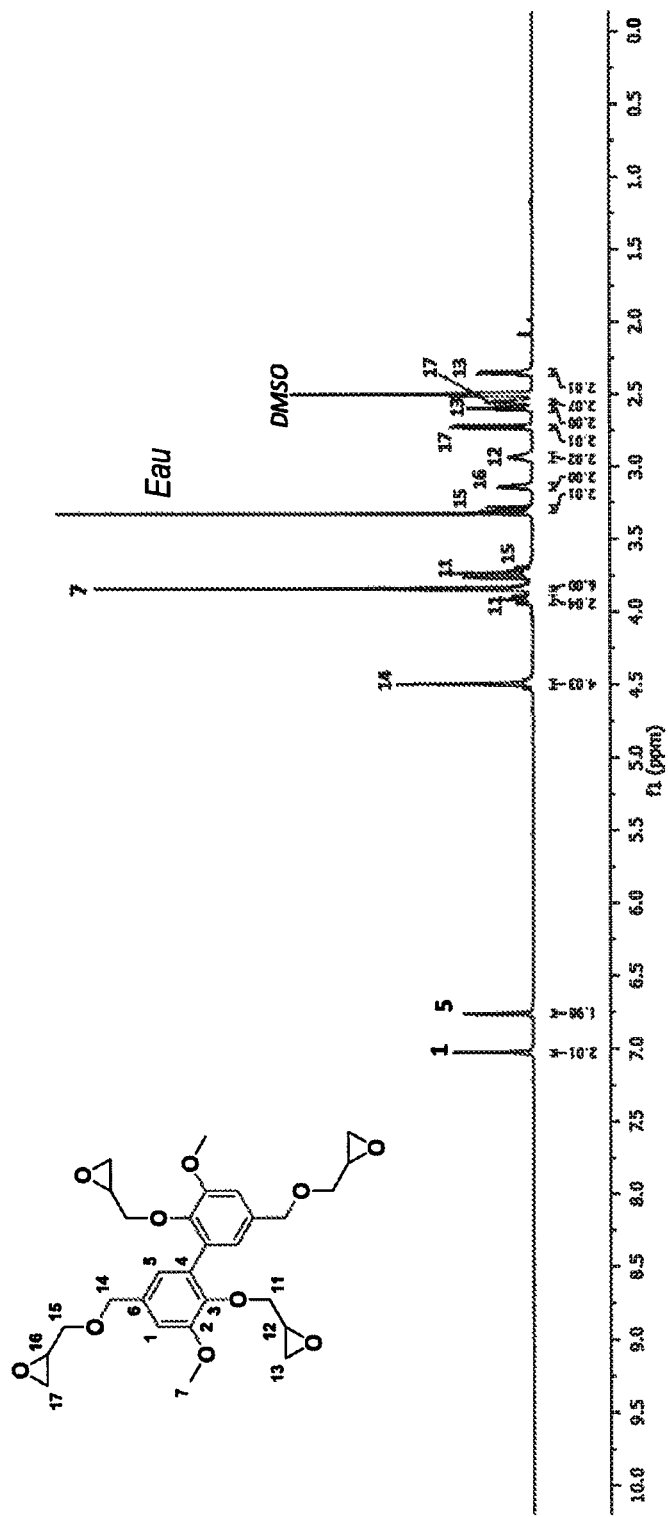
Figure 5B:
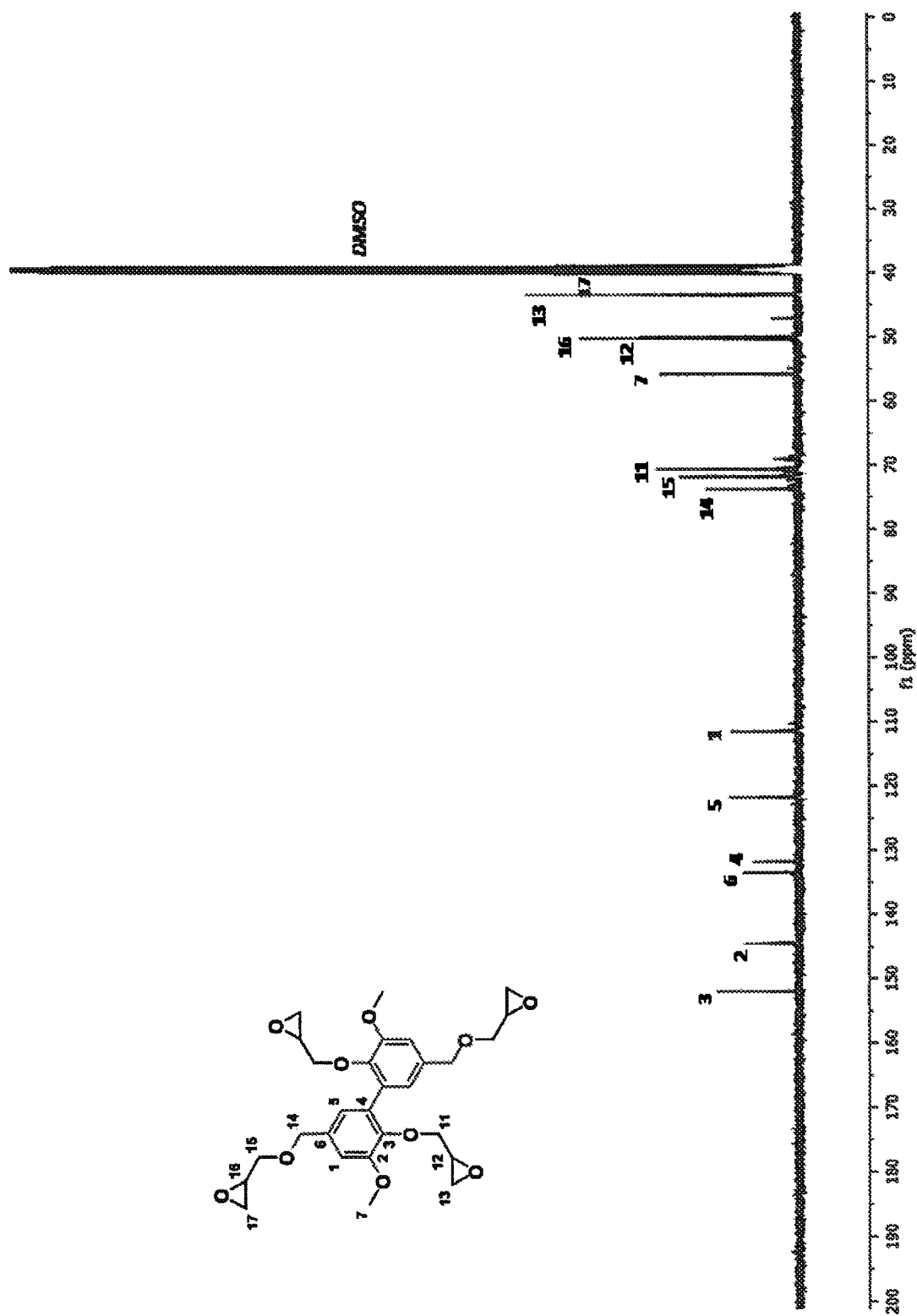

The spectra are shown in FIGS. 5A and 5B respectively.

B1. Polyepoxides Obtained from Said Compounds of Formula (I) (Isolated and/or as a Mixture) (Multi-Epoxidized Prepolymers)

For the polymerization (cross-linking polymerization) of the compounds of the invention obtained in this example (DiGEDVA, TriGEDVA and TetraGEDVA, separately and in a mixture: TriGEDVA (25%)+TetraGEDVA (75% (see above)), diaminodiphenyl sulfone (DDS) was used as hardener. This has the formula:

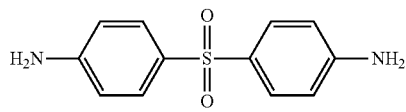 [SMILES: Nc1ccc(S(=O)(=O)c2ccc(N)cc2)cc1]

This hardener was used in a stoichiometric ratio: epoxy/amine=2/1 and the reaction was carried out at 180° C. for 2 hours.

The same reaction was carried out with bisphenol A diglycidyl ether (DGEBA; prepolymer of the prior art obtained from bisphenol A (BPA)).

The polyepoxides obtained have been evaluated in particular by their alpha transition temperature (it can be assimilated to a glass transition temperature. It was determined by dynamic mechanical analysis (DMA)), by their residual coke rate after degradation at 900° C. (Char900; determined by thermogravimetric analysis (TGA)) and by their Young's modulus. The results are shown in Table 1 below.

TABLE 1

| Polyepoxide precursor prepolymers | Tα (° C.) | Char900 (%) | Young's modulus (GPa) |
| --- | --- | --- | --- |
| DGEBA | 203 | 18 | 1.5 |
| DiGEDVA | 206 | 51 | 1.5 |

TABLE 1-continued

| Polyepoxide precursor prepolymers | Tα (° C.) | Char900 (%) | Young's modulus (GPa) |
| --- | --- | --- | --- |
| TriGEDVA | 254 | 49 | 1.4 |
| TetraGEDVA | 312 | 48 | 1.8 |
| TriGEDVA (25%) + TetraGEDVA (75%) | 280 | 50 | 1.4 |

The figures in said Table 1 confirm the interest of the compounds of the invention.

The higher aromaticity of the polyepoxides of the invention strengthens their structure and leads to networks with Tα values of 206 to 312° C. and Young's moduli of 1.4 to 1.8 GPa.

The residual mass at 900° C. is about 50% for the polyepoxides of the invention and only 18% for the polyepoxide of the prior art. This is very interesting in so far as a high residual mass value indicates good flame retardant properties of the materials. Flame tests were carried out on various samples to verify this claim. Epoxies obtained from DGEBA, on direct contact with the flame, burn and the combustion increases and spreads rapidly throughout the sample. Conversely, for the epoxies of the invention, combustion stops rapidly due to the formation of a protective layer of coke on the surface of the materials.

Example 2

A2. Synthesis of a Compound of Formula (I) from Divanillin (DV)

The different steps of the reaction scheme below have been successively implemented.

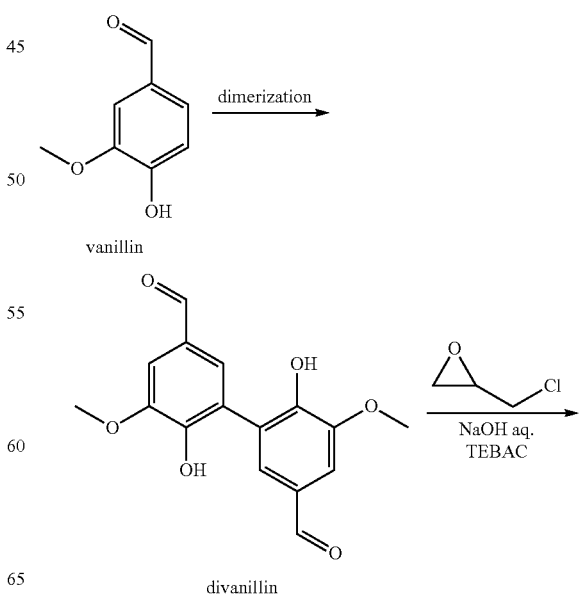

-continued

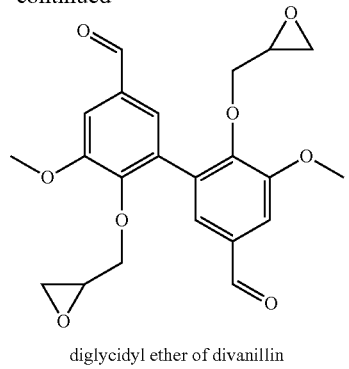

diglycidyl ether of divanillin

Synthesis of Divanillin (DV)

This was done as explained above (according to the protocol in Example 1 of patent application EP 3 002 333).

Synthesis of a Compound of Formula (I) (Multi-Epoxidized Prepolymer): Diglycidyl Ether of Divanillin (DiGEDV)

The aldehyde functions of divanillin were preserved. The OH functions were epoxidized with epichlorohydrin. The procedure was as follows.

3 g of divanillin (10 mmol) was dissolved in 15 mL of epichlorohydrin. 0.3 g of tetrabutylammonium bromide (TEBAC) (0.95 mmol) was added and the resulting mixture was stirred at 80° C. for 12 h. 8 mL of (5 M) NaOH solution (40 mmol) were then added and the mixture was stirred at room temperature for 1.5 h. The product was finally extracted with dichloromethane and washed with water. Dichloromethane and epichlorohydrin were removed from the organic phase using a rotary evaporator. The yield was 90%. Purification was conveniently carried out by flash chromatography using a dichloromethane/methanol solvent gradient (from 99/1 to 90/10 (by volume) for 30 minutes).

The identity of the compound of formula (I) obtained was confirmed by NMR spectroscopy:

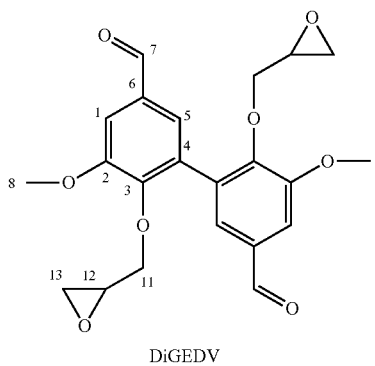

DiGEDV $^1$H NMR (400 MHz, DMSO-d6, δ (ppm)): δ 9.94 (s, H$_7$), 7.60 (d, H$_1$), 7.48 (s, H$_5$), 3.93 (s, H$_8$), 7.0 (s, H$_5$), 6.71 (s, H$_1$), 5.16 (t, H$_{10}$), 4.47 (d, H$_7$), 4.18 (m, H$_{11}$), 3.95 (s, H$_8$), 3.85 (m, H$_{11b}$), 2.98 (m, H$_{12}$), 2.61 (t, H$_{13}$), 2.40 (t, H$_{13b}$).

$^{13}$C NMR (400 MHz, DMSO-d6, δ (ppm)): δ 191.79 (s, C$_7$), δ 152.48 (s, C$_3$), 150.67 (s, C$_2$), 131.84 (s, C$_6$), 131.29 (s, C$_4$), 126.40 (s, C$_5$), 111.48 (s, C$_1$), 74.24 (s, C$_{11}$), 63.14 (s, C$_7$), 55.89 (s, C$_8$), 50.12 (s, C$_{12}$), 43.44 (s, C$_{13}$).

Figure 6B:
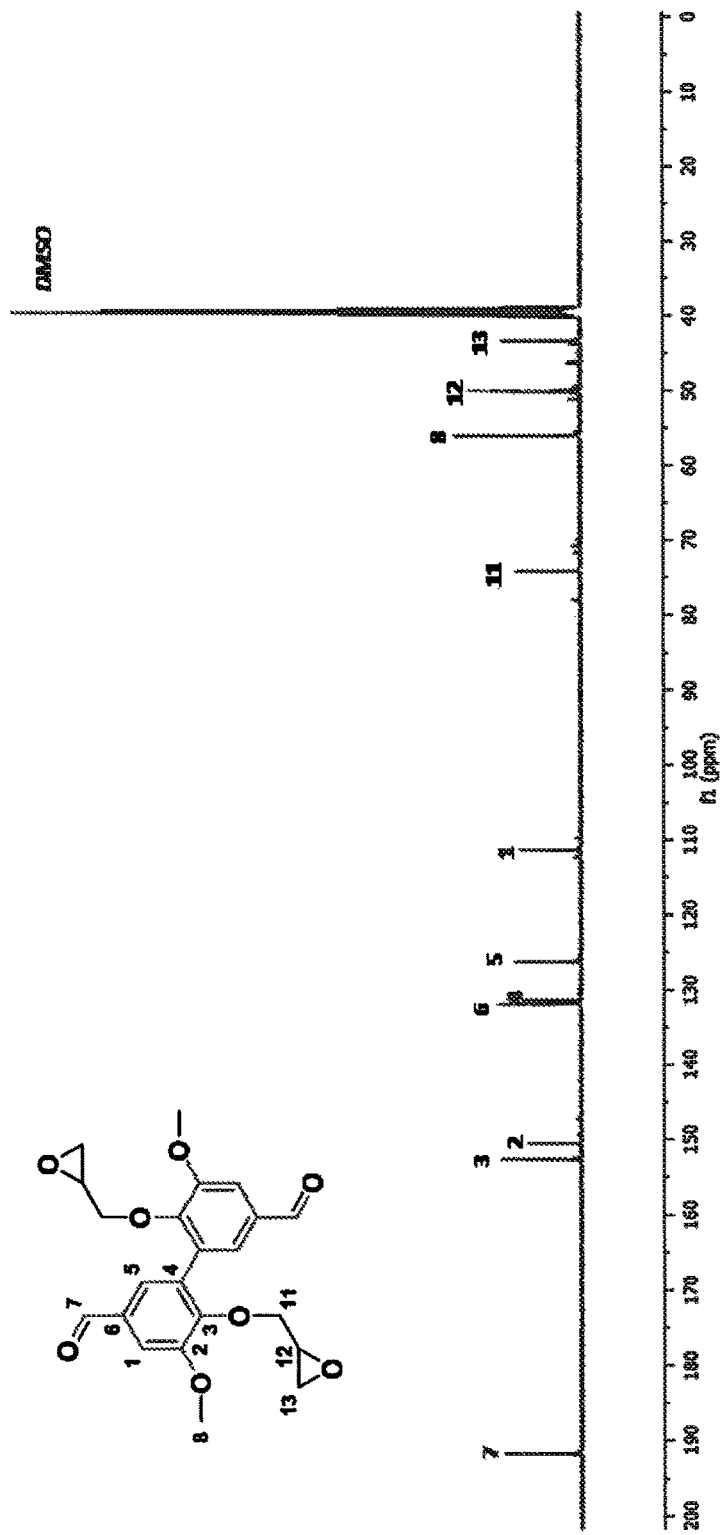

The spectra are shown in FIGS. 6A and 6B respectively.

B2. Polyepoxide Obtained from Said Compound of Formula (I) (Multi-Epoxidized Prepolymer)

For the polymerization of the compound of the invention obtained in this example (diglycidyl ether of divanillin: DiGEDIV), diaminodiphenyl sulfone (DDS), whose chemical formula has been recalled above, was also used as hardener.

This hardener was used in a stoichiometric ratio: epoxy/amine=2/1 and the reaction was carried out at 180° C. for 2 h.

As above, the glass transition temperature (determined by dynamic mechanical analysis (DMA)) and the residual coke content after degradation at 900° C. (determined by thermogravimetric analysis (TGA)) of the prepared polyepoxide were investigated. The results are shown in Table 2 below.

TABLE 2

| Polyepoxide precursor prepolymer | Tα (° C.) | Char900 (%) |
| --- | --- | --- |
| DiGEDV | 180 | 54 |

The figures in said Table 2 confirm the interest of the compounds of the invention.

Example 3

A3. Synthesis of Compounds of Formula (I) (in a Mixture) from Dimethoxyhydroquinone The different steps of the reaction scheme below have been successively implemented.

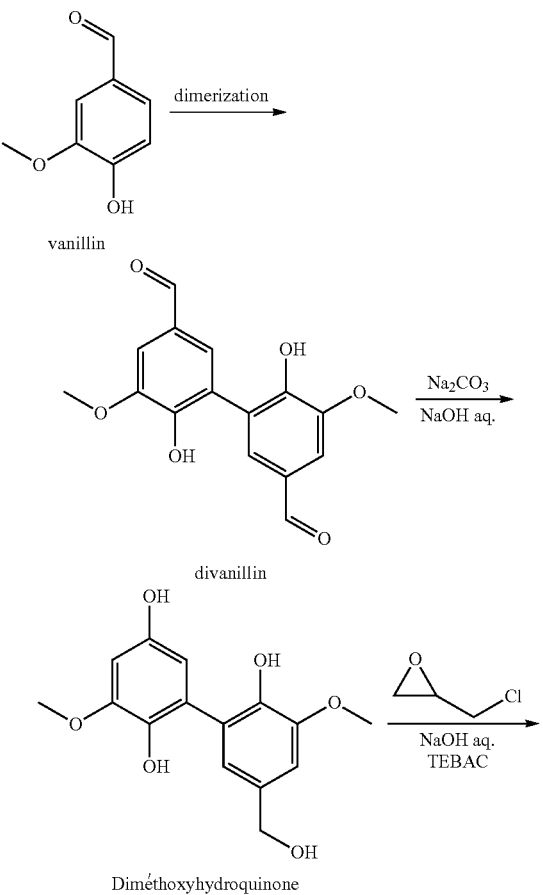

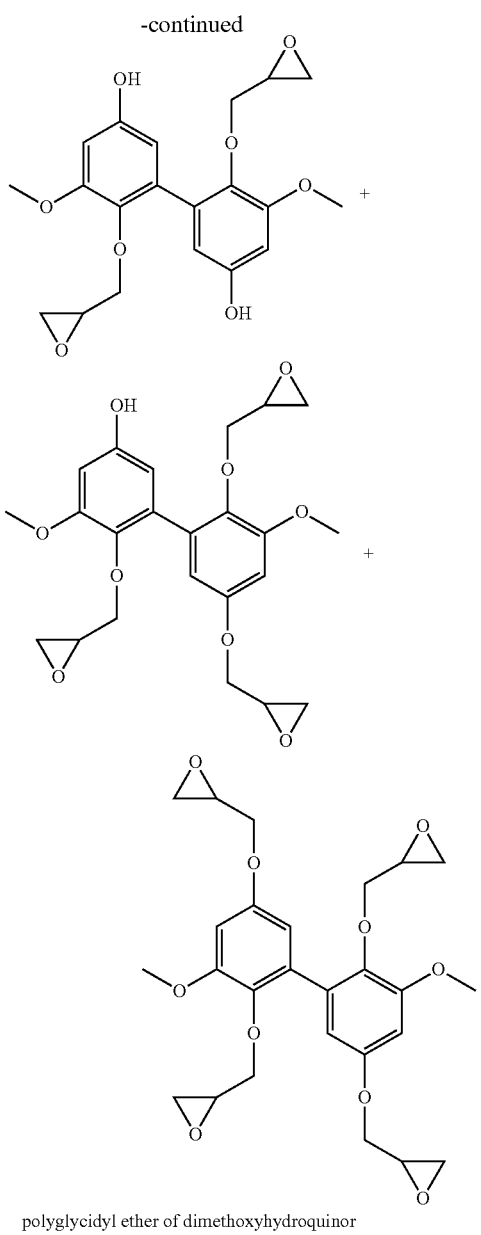

polyglycidyl ether of dimethoxyhydroquinor

Synthesis of Divanillin (DV)

This was done as explained above (according to the protocol in Example 1 of patent application EP 3 002 333).

Synthesis of Dimethoxyhydroquinone (DMHQ)

6 mmol of divanillin (≈1 g) was dissolved in 10 mL of NaOH (0.5 M). 7 mmol of sodium percarbonate were then added slowly. The mixture was then stirred at room temperature for 12 h. After stirring, the solution was acidified with an aqueous solution of HCl (2 M) until pH=3 was reached. The aqueous phase was then extracted with ethyl acetate. The organic phases were collected and washed with water and dried over magnesium sulfate (MgSO$_4$). Ethyl acetate was then removed under vacuum using a rotary evaporator. Further purification was carried out by flash chromatography using a dichloromethane/methanol gradient solvent (from 99/1 to 90/10 (by volume) for 30 minutes). The yield was less than 50%. It should be noted that the synthesis carried out (repeated several times) had not been optimized either for higher yield or for obtaining a pure compound.

The identity of DMHQ was confirmed by NMR spectroscopy:

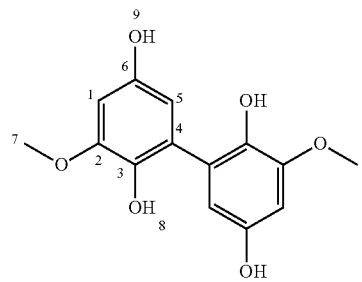

$^1$H NMR (400 MHz, DMSO-d6, δ (ppm)): δ 8.79 (s, H$_8$), 7.76 (s, H$_9$), 6.38 (d, H$_1$), 6.15 (d, H$_5$), 3.75 (s, H$_7$).

$^{13}$C NMR (400 MHz, DMSO-d6, δ (ppm)): δ 149.76 (s, C$_3$), 148.62 (s, C$_2$), 135.77 (s, C$_6$), 126.65 (s, C$_4$), 108.35 (s, C$_5$), 99.35 (s, C$_3$), 55.65 (s, C$_7$).

Synthesis of Compounds of Formula (I) (Multi-Epoxidized Prepolymers): Polyglycidyl Ethers of Dimethoxyhydroquinone 0.5 g of dimethoxyhydroquinone (as prepared above) was dissolved in 10 mL of epichlorohydrin. 0.05 g of tetrabutylammonium bromide (TEBAC) was added and the resulting mixture was stirred at 80° C. for 20 h. 5 mL of a NaOH solution (5 M) (40 mmol) were then added and the resulting new mixture was stirred at room temperature for 24 h. The resulting mixture was extracted with dichloromethane and washed with water. Dichloromethane and epichlorohydrin were removed from the organic phase using a rotary evaporator. The synthesis used was not optimized.

A mixture of polyglycidyl ethers of dimethoxyhydroquinone was thus obtained, said polyglycidyl ethers present in variable proportions, not evaluated. This mixture was analyzed by $^1$H NMR spectroscopy. The spectrum obtained is shown in FIG. 7A. This spectrum certainly confirms the presence of several epoxy functions.

B3. Polyepoxide Obtained from Said Compounds of Formula (I) (Multi-Epoxidized Prepolymers)

For the polymerization of the mixture of compounds of the invention obtained in this example, diaminodiphenyl sulfone (DDS), whose chemical formula has been recalled above, was also used as a hardener.

This hardener was used in a stoichiometric ratio: epoxy/amine=2/1. In this example, the polyepoxide was not successively prepared and then analyzed by DMA (for determination of its Tg). It was generated, in small amounts (a few mg), during the implementation of differential scanning calorimetry (DSC), for determination of its Tg.

The rate of residual coke, after degradation at 900° C., determined by thermogravimetric analysis (TGA), was determined on this small amount generated during the DSC analysis. The results are shown in Table 3 below.

TABLE 3

| Polyepoxide precursor prepolymer | Tg (° C.) | Char900 (%) |
|---|---|---|
| PolyGEDMHQ | 212 | 41 |

Example 4

A4. Synthesis of a Compound of Formula (I) from Methyl Vanillate

The different steps of the reaction scheme below have been successively implemented.

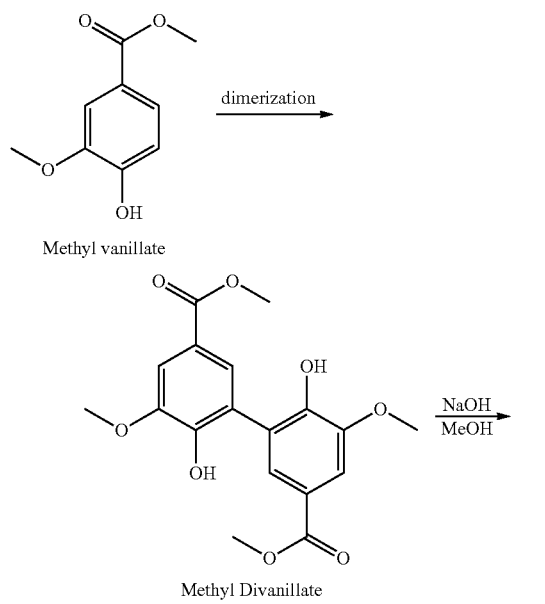

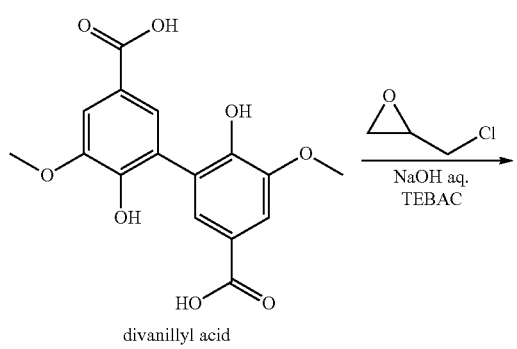

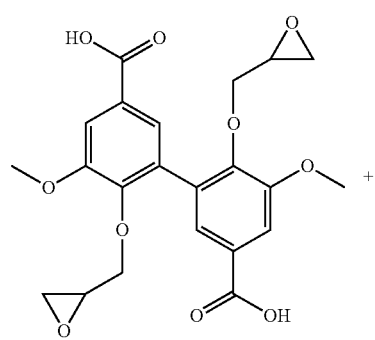

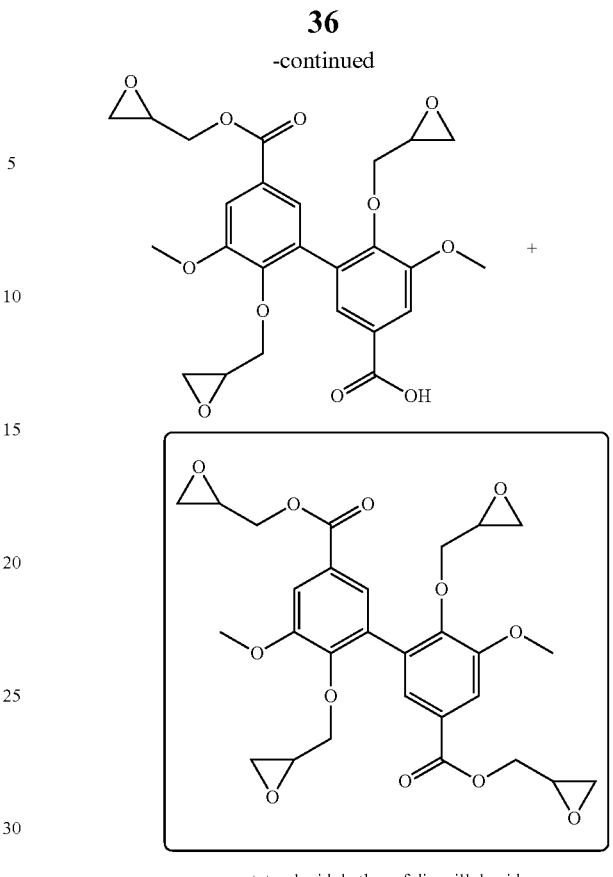

tetraglycidyl ether of divanillyl acid
polyglycidyl ether of divanillyl alcohol

Synthesis of Methyl Divanillate

For the preparation of methyl divanillate, starting from methyl vanillate (marketed by Sigma-Aldrich), a procedure has been followed which is very similar to that described for the preparation of divanillin in point A1 above (i.e. according to the procedure described in Example 4 of patent application EP 3 002 333).

Obtaining methyl divanillate was confirmed by NMR spectroscopy:

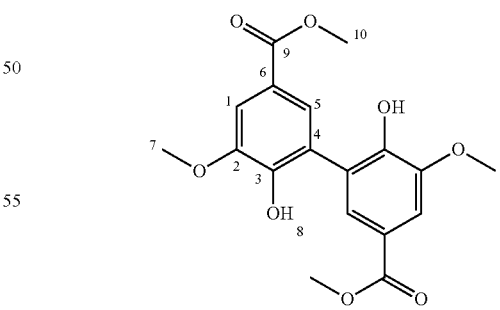

$^1$H NMR (400 MHz, DMSO-d6, δ (ppm)): δ 9.51 (s, $H_8$), 7.46 (d, $H_1$), 7.45 (d, $H_5$), 3.90 (s, $H_7$), 3.80 (s, $H_{10}$).

$^{13}$C NMR (400 MHz, DMSO-d6, δ (ppm)): δ 166.09 (s, $C_9$), 148.88 (s, $C_3$), 147.47 (s, $C_2$), 125.40 (s, $C_5$), 124.36 (s, $C_6$), 119.48 (s, $C_4$), 110.92 (s, $C_1$), 56.01 (s, $C_7$), 51.79 (s, $C_{10}$).

Synthesis of Divanillic Acid (DVAc)

This saponification was carried out according to the procedure described in Example 13 of patent application EP 3 002 333.

Obtaining divanillic acid (DVAc) was confirmed by NMR spectroscopy:

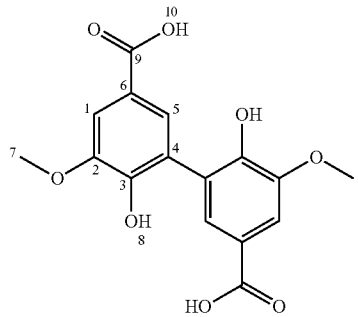

$^1$H NMR (400 MHz, DMSO-d6, δ (ppm): δ 9.39 (s, H$_8$), 7.45 (d, H$_1$), 7.41 (d, H$_5$), 3.89 (s, H$_7$).

$^{13}$C NMR (400 MHz, DMSO-d6, δ (ppm)): δ 167.18 (s, C$_9$), 148.36 (s, C$_3$), 147.22 (s, C$_2$), 125.44 (s, C$_6$), 124.19 (s, C$_4$), 120.44 (s, C$_5$), 111.05 (s, C$_1$), 55.89 (s, C$_7$).

Synthesis of a Compound of Formula (I) (Multi-Epoxidized Prepolymer): Tetraglycidyl Ether of Divanillic Acid (TetraGEDVAc)

0.5 g of divanillic acid was dissolved in 10 mL of epichlorohydrin. 0.05 g of tetrabutylammonium bromide (TEBAC) was added and the resulting mixture was stirred at 80° C. for 2 h. 5 mL of a NaOH solution (5 M) (40 mmol) were then added and the resulting new mixture was stirred at room temperature for 20 h. The product was extracted with dichloromethane and washed with water. Dichloromethane and epichlorohydrin were removed from the organic phase using a rotary evaporator. Tetraglycidyl ether of divanillyl acid was isolated from the reaction mixture by flash chromatography, using a dichloromethane/methanol gradient solvent (from 99/1 to 90/10 (by volume) for 30 minutes). The yield was less than 50%. The implemented synthesis was not optimized.

Obtaining said tetraglycidyl ether of divanillic acid was confirmed by NMR spectroscopy:

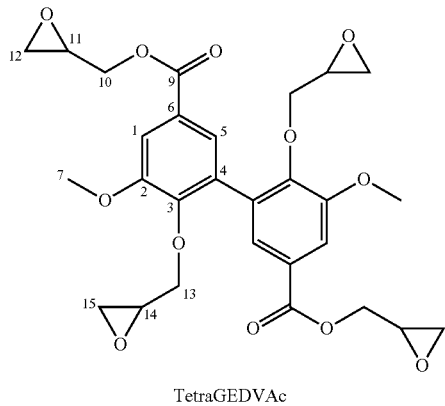 [SMILES: COc1cc(C(=O)OCC2CO2)cc(-c2cc(C(=O)OCC3CO3)cc(OC)c2OCC2CO2)c1OCC1CO1]

TetraGEDVAc $^1$H NMR (400 MHz, DMSO-d6, δ (ppm)): δ 7.63 (d, H$_1$), 7.50 (d, H$_5$), 4.65 (d, H$_{10}$), 4.15 (m, H$_{10b}$), 4.09 (s, H$_{14}$), 3.94 (m, H$_7$), 3.86 (m, H$_{14b}$), 3.35 (m, H$_{11}$), 2.97 (m, H$_{13}$), 2.83 (m, H$_{12}$), 2.73 (m, H$_{15}$), 2.62 (m, H$_{12b}$), 2.38 (m, H$_{15b}$).

$^{13}$C NMR (400 MHz, DMSO-d6, δ (ppm)): δ 164.94 (s, C$_9$), 152.12 (s, C$_3$), 149.56 (s, C$_2$), 131.23 (s, C$_6$), 124.57 (s, C$_4$), 124.18 (s, C$_5$), 112.98 (s, C$_1$), 74.01 (s, C$_{13}$), 56.08 (s, C$_{10}$), 50.24 (s, C$_7$), 49.94 (s, C$_{14}$), 49.04 (s, C$_{11}$), 43.90 (s, C$_{12}$), 43.36 (s, C$_{15}$).

Figure 8A:
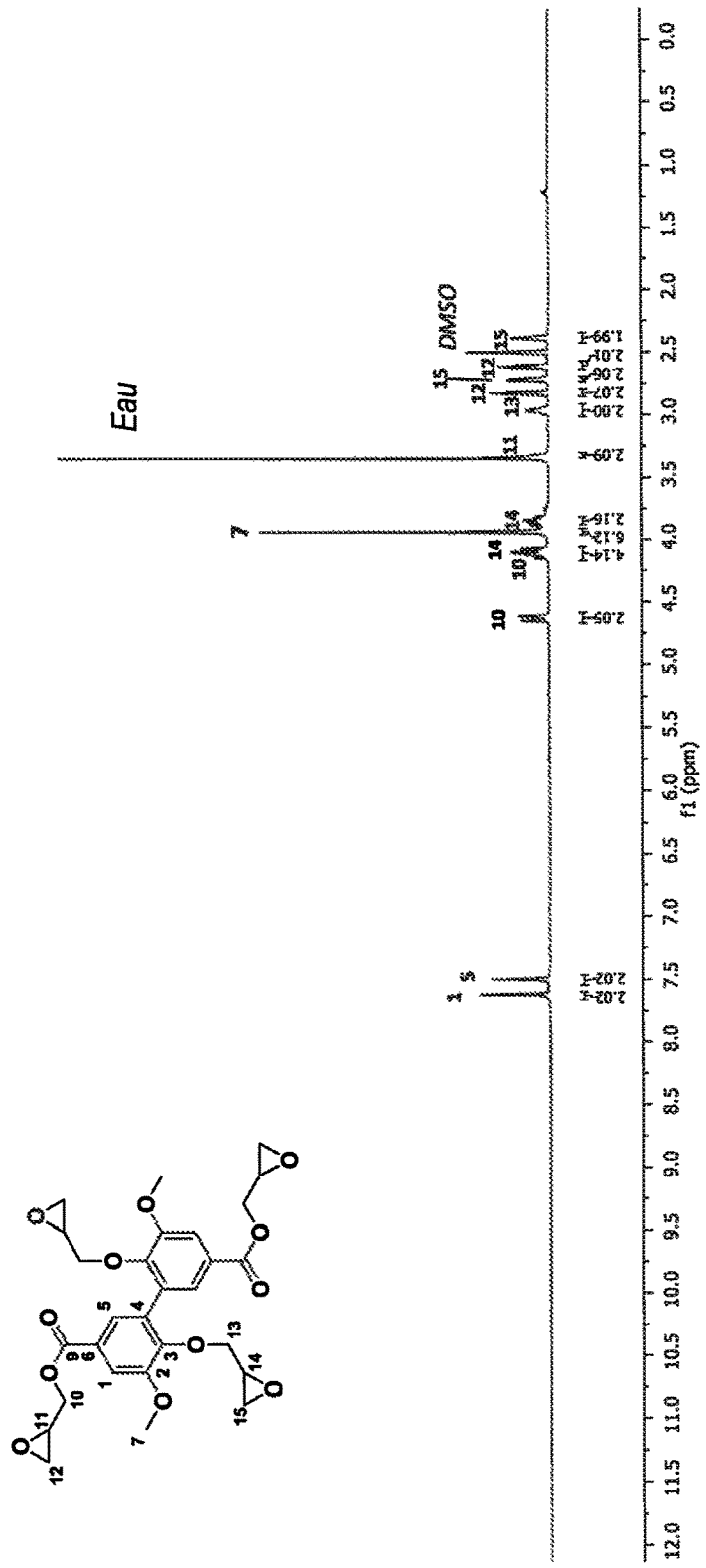
Figure 8B:
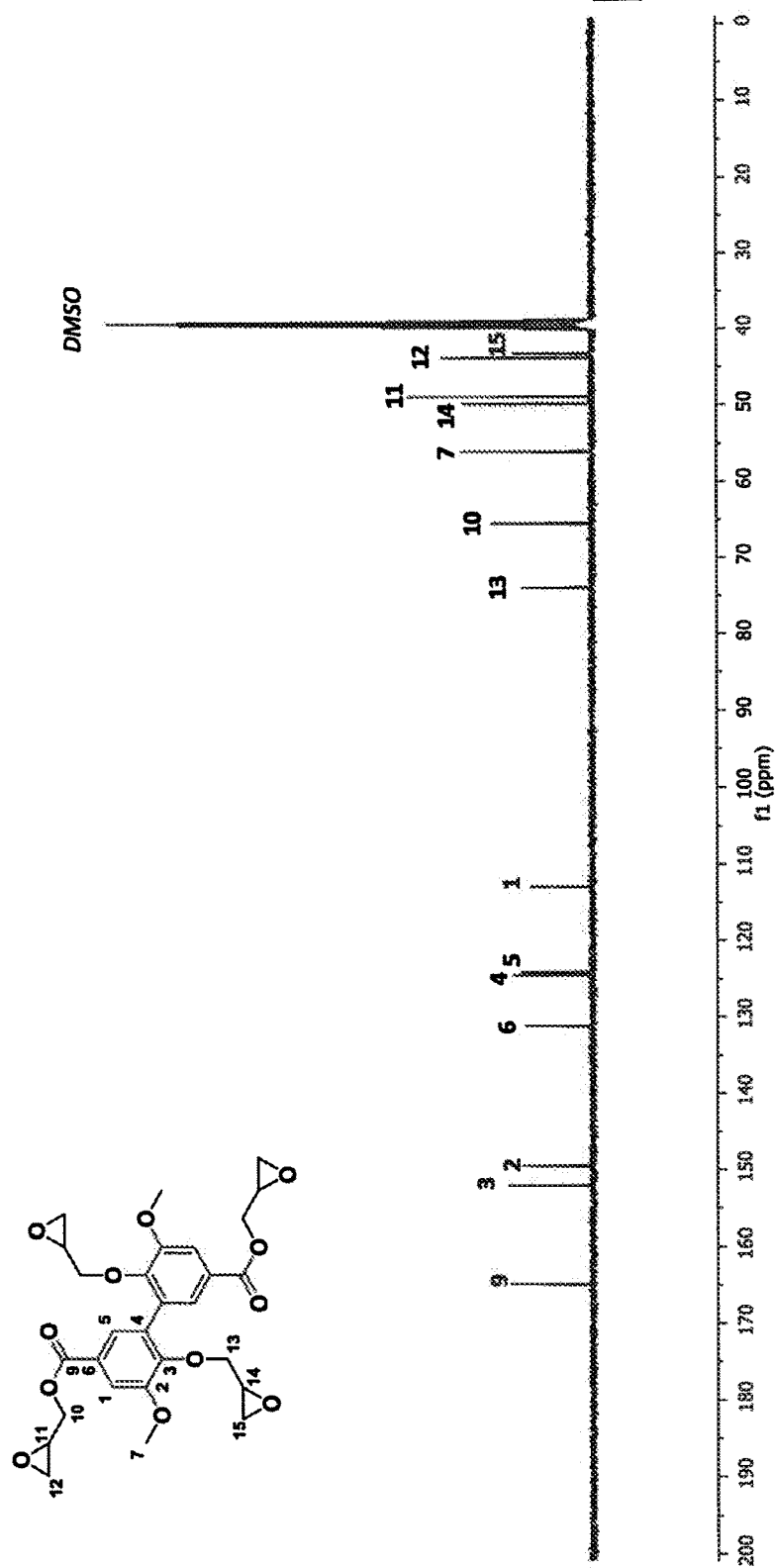

The spectra are shown in FIGS. 8A and 8B respectively.

Example 5

A5. Synthesis of Compounds of Formula (I) from Eugenol

The different steps of the reaction scheme below have been successively implemented.

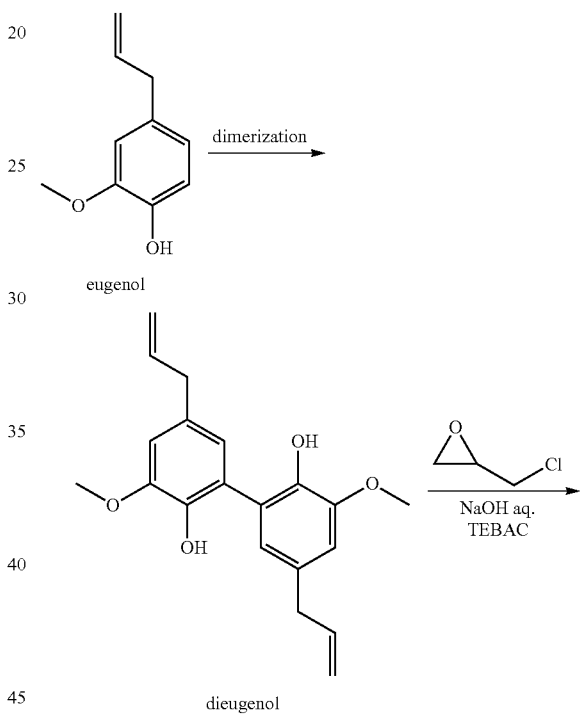

eugenol dieugenol

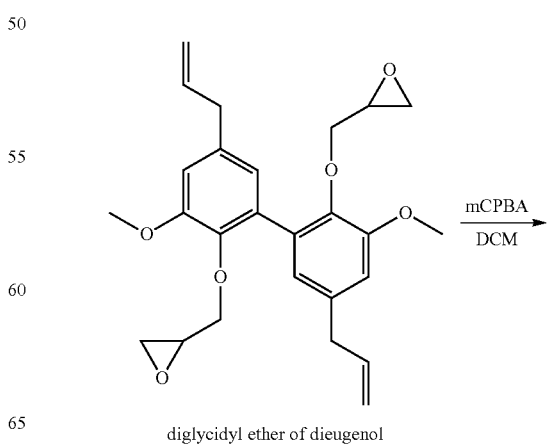

diglycidyl ether of dieugenol

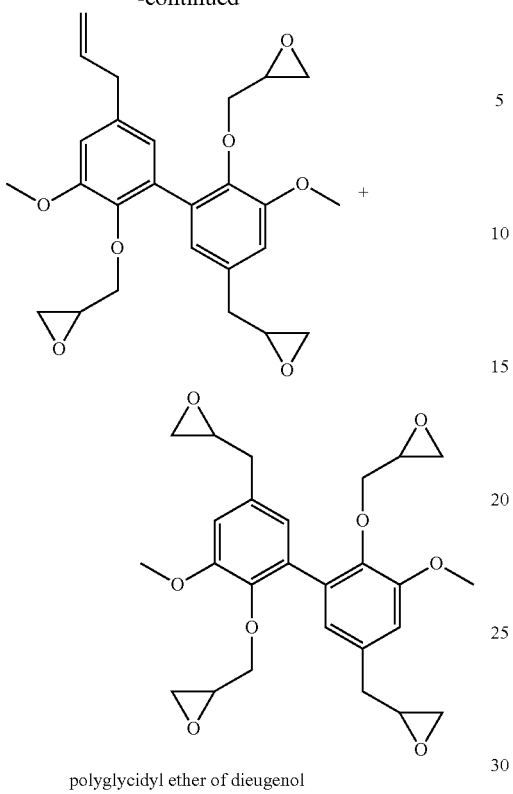

polyglycidyl ether of dieugenol

Synthesis of Dieugenol (DEG)

For the preparation of dieugenol, the procedure is very similar to that described for the preparation of divanillin in point A1 above. This procedure has already been described in Example 7 of patent application EP 3 002 333.

Obtaining dieugenol (DEG) was confirmed by NMR spectroscopy:

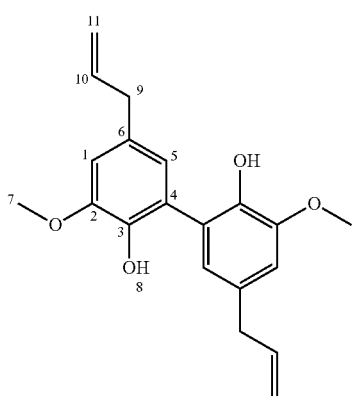

$^1$H NMR (400 MHz, DMSO-d6, δ (ppm)): δ 8.16 (s, H$_8$), 6.73 (d, H$_1$), 6.52 (d, H$_5$), 5.93 (m, H$_{10}$), 5.05 (m, H$_{11}$), 3.79 (s, H$_7$), 3.27 (d, H$_9$).

$^{13}$C NMR (400 MHz, DMSO-d6, δ (ppm)): δ 147.61 (s, C$_2$), 141.79 (s, C$_3$), 138.15 (s, C$_{10}$), 129.60 (s, C$_6$), 125.91 (s, C$_4$), 122.84 (s, C$_5$), 115.39 (s, C$_{11}$), 110.79 (s, C$_1$), 55.82 (s, C$_7$), 39.23 (s, C$_9$).

Synthesis of a Compound of Formula (I) (Multi-Epoxidized Prepolymer):

Diglycidyl Ether of Dieugenol (DiGEDEG)

3 g of dieugenol was dissolved in 15 mL of epichlorohydrin. 0.3 g of tetrabutylammonium bromide (TEBAC) (0.95 mmol) was added and the resulting mixture was stirred at 80° C. for 24 h. 8 mL of a NaOH solution (5 M) (40 mmol) were then added and the new resulting mixture was stirred at room temperature for 24 h. The product was extracted with dichloromethane and washed with water. Dichloromethane and epichlorohydrin were removed from the organic phase using a rotary evaporator. The synthesis used was not optimized: the conversion was not total. The product obtained was not pure.

Obtaining diglycidyl ether of dieugenol (DiGEDEG) was confirmed by NMR spectroscopy:

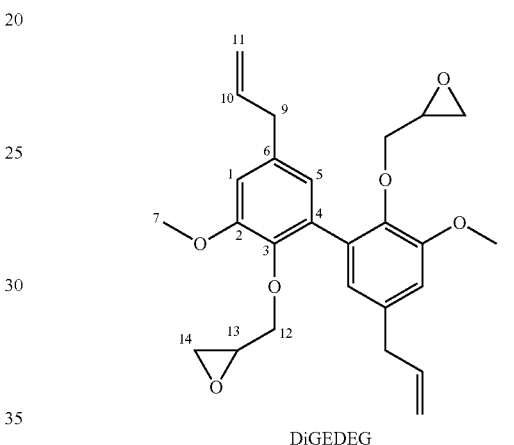

DiGEDEG $^1$H NMR (400 MHz, DMSO-d6, δ (ppm)): δ 6.87 (d, H$_1$), 6.59 (d, H$_5$), 5.96 (m, H$_{10}$), 5.02 (m, H$_{11}$), 3.87 (s, H$_{12}$), 3.81 (s, H$_7$), 3.73 (s, H$_{12b}$), 3.35 (d, H$_9$), 2.93 (d, H$_{13}$), 2.59 (d, H$_{14}$), 2.34 (d, H$_{14b}$).

$^{13}$C NMR (400 MHz, DMSO-d6, δ (ppm)): δ 151.99 (s, C$_2$), 143.47 (s, C$_3$), 137.66 (s, C$_{10}$), 135.03 (s, C$_6$), 132.09 (s, C$_4$), 122.39 (s, C$_5$), 115.79 (s, C$_{11}$), 112.30 (s, C$_1$), 73.72 (s, C$_{12}$), 55.73 (s, C$_7$), 50.04 (s, C$_{13}$), 43.41 (s, C$_{14}$), 39.22 (s, C$_9$).

Figure 9B:
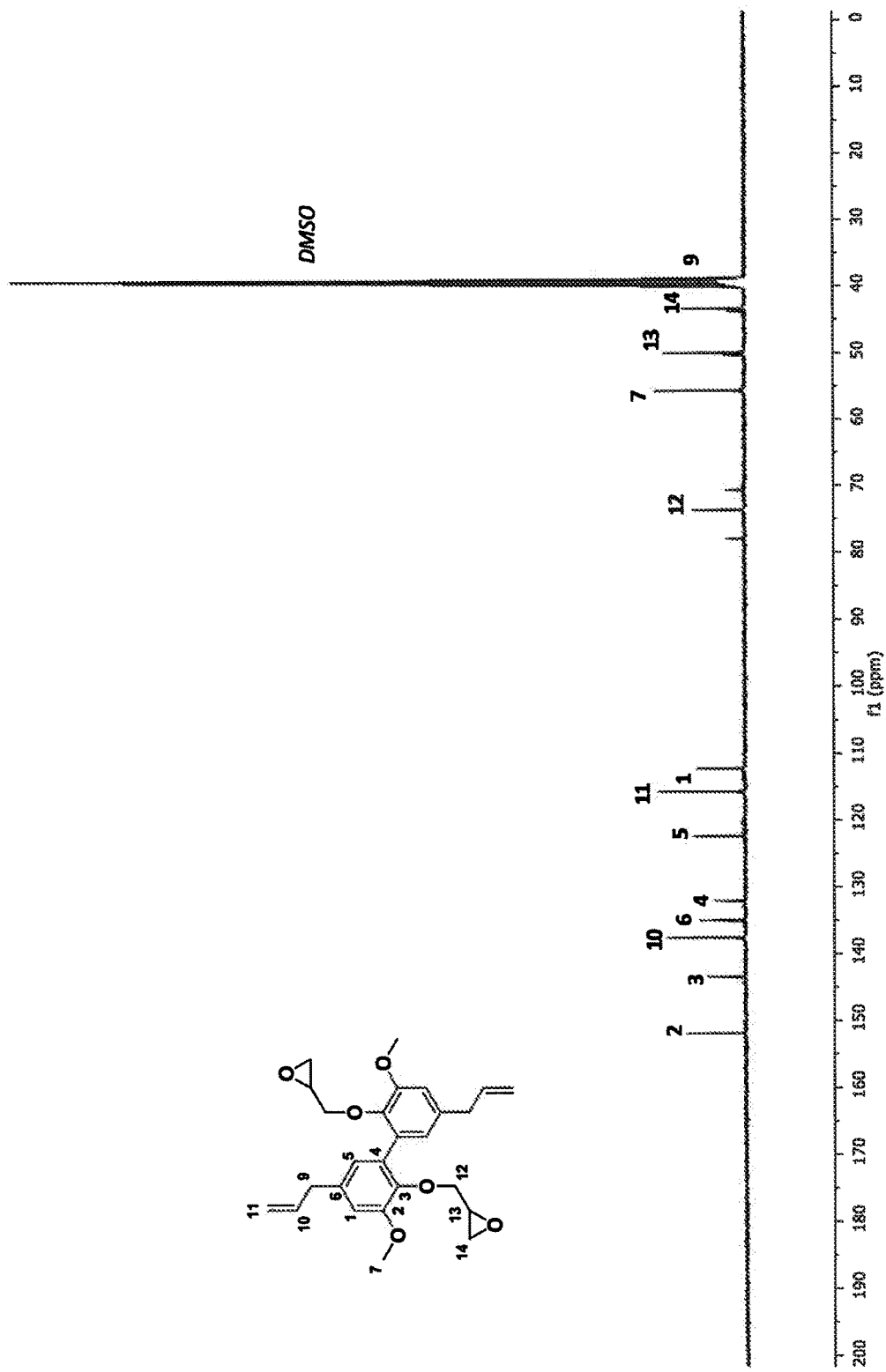

The spectra are shown in FIGS. 9A and 9B respectively.

Synthesis of Another Compound of Formula (I) (Multi-Epoxidized Prepolymer): Tetraglycidyl Ether of Dieugenol (TetraGEDEG)

0.5 g of diglycidyl ether of dieugenol (as obtained above) was dissolved in 7.5 mL of cold DCM. 1 g of mCPBA was solubilized in 7.5 mL of cold DCM and then gradually added to the DiGEDEG solution. The mixture was stirred at room temperature for 24 h. The product was then washed twice with a saturated solution of NaHCO$_3$ and three times with distilled water. Finally, dichloromethane was removed using a rotary evaporator. Further purification was carried out by flash chromatography using a dichloromethane/methanol gradient solvent (from 99/1 to 90/10 (by volume) for 30 minutes). The yield of this non-optimized synthesis was less than 50%. However, only the tetraglycidyl ether of dieugenol was synthesized (in view of the amount of mCPBA used and the reaction time (24 h) with said mCPBA) and isolated.

Obtaining tetraglycidyl ether of dieugenol was confirmed by NMR spectroscopy:

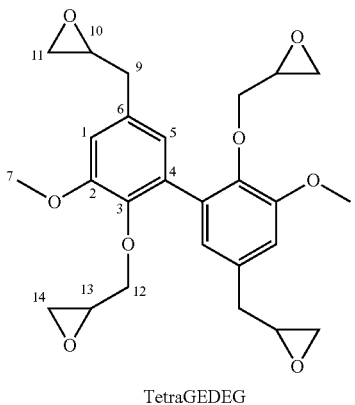

TetraGEDEG $^1$H NMR (400 MHz, DMSO-d6, δ (ppm)): δ 6.98 (d, H$_1$), 6.71 (d, H$_5$), 3.93 (m, H$_{12}$), 3.83 (s, H$_7$), 3.73 (m, H$_{12}$), 3.13 (m, H$_{10}$), 2.94 (m, H$_{13}$), 2.77 (m, H$_9$ H$_{11}$), 2.60 (m, H$_{11b}$ H$_{14}$), 2.36 (m, H$_{14b}$).

$^{13}$C NMR (400 MHz, DMSO-d6, δ (ppm)): δ 151.94 (s, C$_2$), 143.79 (s, C$_3$), 132.84 (s, C$_6$), 131.98 (s, C$_4$), 122.94 (s, C$_5$), 112.86 (s, C$_1$), 73.74 (s, C$_{12}$), 55.75 (s, C$_7$), 51.98 (s, C$_{11}$), 50.03 (s, C$_{10}$), 46.10 (s, C$_{13}$), 43.39 (s, C$_{14}$), 37.5 (s, C$_9$.

Figure 10B:
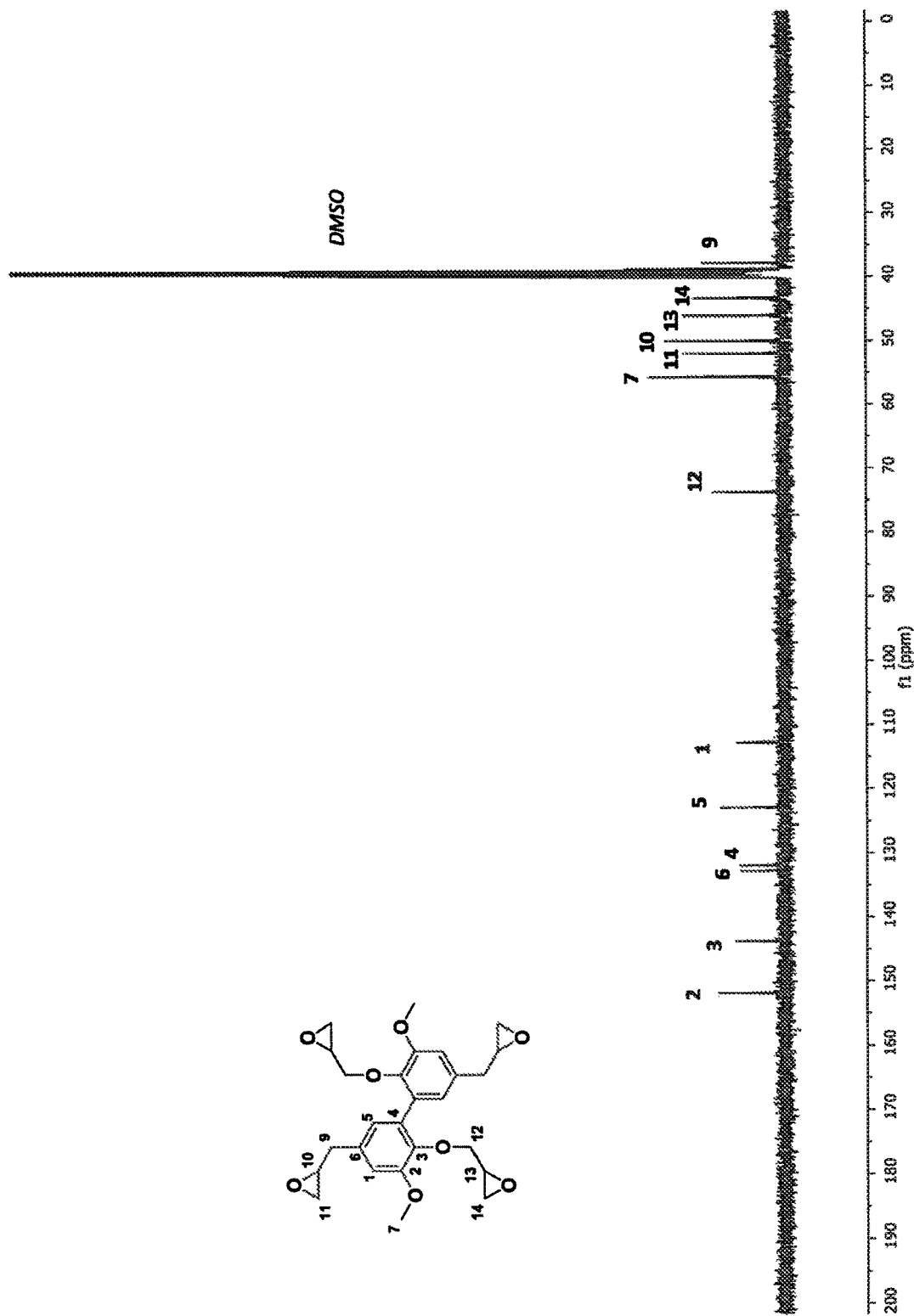

The spectra are shown in FIGS. 10A and 10B respectively.

B5. Polyepoxide Obtained from the Compound of Formula (I): Diglycidyl Ether of Dieugenol (DiGEDEG) (Multi-Epoxidized Prepolymer)

For the polymerization of the di-epoxidized compound of the invention obtained in this example (diglycidyl ether of dieugenol: DiGEDEG), diaminodiphenyl sulfone (DDS), whose chemical formula has been recalled above, was also used as a hardener.

This hardener was used in a stoichiometric ratio: epoxy/amine=2/1. In this example too, the polyepoxide was not successively prepared and then analyzed by DMA (for determination of its Tg). It was generated, in small amounts (a few mg), during the implementation of differential scanning calorimetry (DSC) for determination of its Tg.

The rate of residual coke, after degradation at 900° C., determined by thermogravimetric analysis (TGA), was determined on this small amount generated during the DSC analysis. The results are shown in Table 4 below.

TABLE 4

| Polyepoxide precursor prepolymer | Tg (° C.) | Char900 (%) |
|---|---|---|
| DiGEDEG | 144 | 38 |

The figures in said Table 4 confirm the interest of the compounds of the invention.

II. COMPOUNDS OF FORMULA (I), IN WHICH R$_3$=O—CH$_3$, DERIVED FROM VANILLIN, METHYL VANILLATE OR EUGENOL

Example 6

A6. Synthesis of Compounds of Formula (I) (Multi-Epoxidized Phenolic Compounds) from Methylated Biphenols Etherification under the conditions explained below has been implemented on the biphenols identified below.

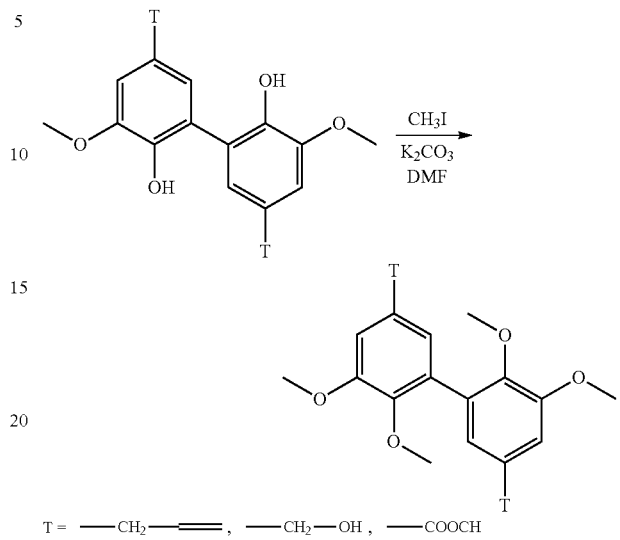

T = —CH$_2$—=, —CH$_2$—OH, —COOCH

Synthesis of Methylated Biphenols 26 mmol of bisphenol (see below) and 15.2 g of potassium carbonate (110 mmol) were dissolved in 120 mL of DMF. 9.6 mL of iodomethane (158 mmol) were then slowly added to the mixture. After 15 h at 80° C., the mixture was filtered and the resulting solution was poured into cold water. The methylated compound precipitated and was recovered by filtration and dried under vacuum. The typical yield was 80%.

Etherification was implemented with successively:
divanillyl alcohol (DVA; T=CH$_2$OH) (as obtained in point A1 of Example 1 above), to obtain methylated divanillyl alcohol (mDVA). Said mDVA was characterized by NMR spectroscopy:

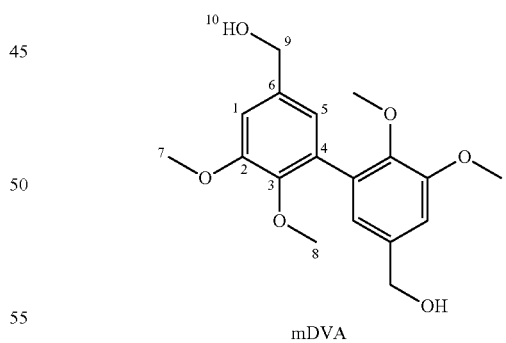

mDVA

1H NMR (400 MHz, DMSO-d6, δ (ppm)): δ 6.99 (d, H$_1$), 6.67 (d, H$_5$), 5.15 (s, H$_{10}$), 4.47 (s, H$_9$), 3.83 (s, H$_7$), 3.50 (s, H$_8$).

$^{13}$C NMR (400 MHz, DMSO-d6, δ (ppm)): δ 152.00 (s, C$_3$), 144.81 (s, C$_2$), 137.64 (s, C$_6$), 132.12 (s, C$_4$), 120.33 (s, C$_5$), 110.18 (s, C$_1$), 62.63 (s, C$_9$), 59.91 (s, C$_8$), 55.52 (C$_7$).

methyl divanillate (MDEV; T=—COOCH$_3$) (as obtained in point A4 of Example 4 above), to obtain methylated methyl divanillate (mDVE). This was characterized by spectroscopy:

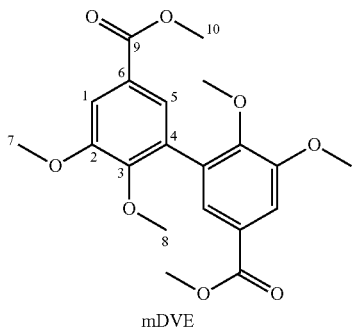

mDVE

1H NMR (400 MHz, DMSO-d6, δ (ppm)): δ 7.59 (d, $H_1$), 7.40 (d, $H_5$), 3.92 (s, $H_7$), 3.83 (s, $H_{10}$), 3.62 (s, $H_8$).

$^{13}$C NMR (400 MHz, DMSO-d6, δ (ppm)): δ 165.67 (s, $C_9$), 152.27 (s, $C_3$), 150.36 (s, $C_2$), 131.28 (s, $C_6$), 124.70 (s, $C_4$), 123.96 (s, $C_5$), 112.76 (s, $C_1$), 60.29 (s, $C_8$), 55.92 (s, $C_7$), 52.18 ($C_{10}$).

Said methylated methyl divanillate was then hydrolyzed under the conditions specified below. 10 mmol of methyl divanillate was solubilized in 30 mL of methanol. 3 g of sodium hydroxide (75 mmol) were added to the mixture, which was then stirred and heated at reflux for 4 h. After cooling to room temperature, an aqueous solution of hydrochloric acid (2 M) was added until pH=3 was reached. The resulting precipitate (methylated divanillic acid (mDVAc)) was then filtered and dried at 80° C. in an oven under reduced pressure. Said methylated divanillic acid (mDVAc) was characterized by NMR spectroscopy:

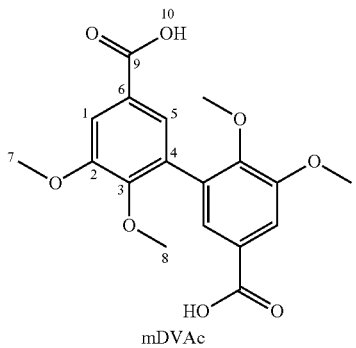

mDVAc $^1$H NMR (400 MHz, DMSO-d6, δ (ppm)): δ 12.94 (s, $H_{10}$), 7.58 (d, $H_1$), 7.39 (d, $H_5$), 3.91 (s, $H_7$), 3.61 (s, $H_8$).

$^{13}$C NMR (400 MHz, DMSO-d6, δ (ppm)): δ 166.83 (s, $C_9$), 152.20 (s, $C_3$), 150.07 (s, $C_2$), 131.34 (s, $C_6$), 125.91 (s, $C_4$), 124.13 (s, $C_5$), 112.93 (s, $C_1$), 60.28 (s, $C_8$), 55.87 (s, $C_7$).

dieugenol (DEG; T=—$CH_2$—CH=$CH_2$) (as obtained in point A5 of Example 5 above), to obtain methylated dieugenol (mDEG). Said mDEG was characterized by NMR spectroscopy:

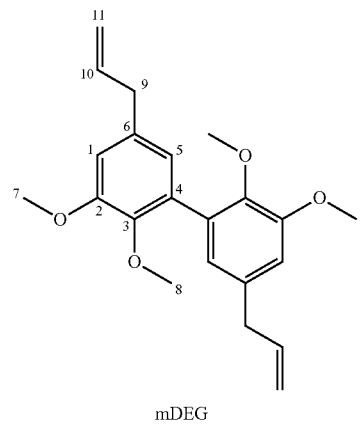

mDEG $^1$H NMR (400 MHz, DMSO-d6, δ (ppm)): δ 6.85 (d, $H_1$), 6.54 (d, $H_5$), 5.96 (m, $H_{10}$), 5.07 (m, $H_{11}$), 3.81 (s, $H_7$), 3.48 (s, $H_8$), 3.34 (d, $H_9$)

$^{13}$C NMR (400 MHz, DMSO-d6, δ (ppm)): δ 152.16 (s, $C_2$), 144.41 (s, $C_3$), 137.67 (s, $C_{10}$), 134.78 (s, $C_6$), 132.29 (s, $C_4$), 122.26 (s, $C_5$), 115.80 (s, $C_{11}$), 112.17 (s, $C_1$), 59.91 (s, $C_7$), 55.58 (s, $C_9$), 39.22 (s, $C_7$), 35.76 (s, $C_7$).

Synthesis of Compounds of Formula (I) (Multi-Epoxidized Prepolymers)

Epoxidation was carried out as described above:
(with epichlorohydrin) to epoxidize the alcohol functions of mDVA. The diglycidyl ether of methylated divanillyl alcohol (DiGEmDVA) was obtained. Said DiGEmDVA was characterized by NMR spectroscopy:

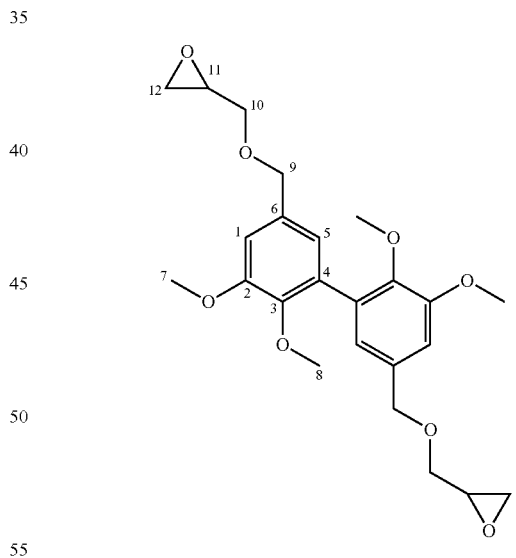

$^1$H NMR (400 MHz, DMSO-d6, δ (ppm)): δ 7.01 (d, $H_1$), 6.72 (d, $H_5$), 4.49 (t, $H_9$), 3.84 (d, $H_7$), 3.77 (m, $H_{10}$), 3.52 (s, $H_8$), 3.31 (m, $H_{10b}$), 3.15 (m, $H_{11}$), 2.73 (t, $H_{12}$), 2.55 (m, $H_{12b}$).

$^{13}$C NMR (400 MHz, DMSO-d6, δ (ppm)): δ 152.20 (s, $C_3$), 145.48 (s, $C_2$), 133.25 (s, $C_6$), 131.98 (s, $C_4$), 121.66 (s, $C_5$), 111.35 (s, $C_1$), 71.90 (s, $C_9$), 70.71 (s, $C_{10}$), 59.90 (s, $C_8$), 55.61 (s, $C_7$), 50.27 (s, $C_{11}$), 43.41 (s, $C_{12}$).

Figure 11A:
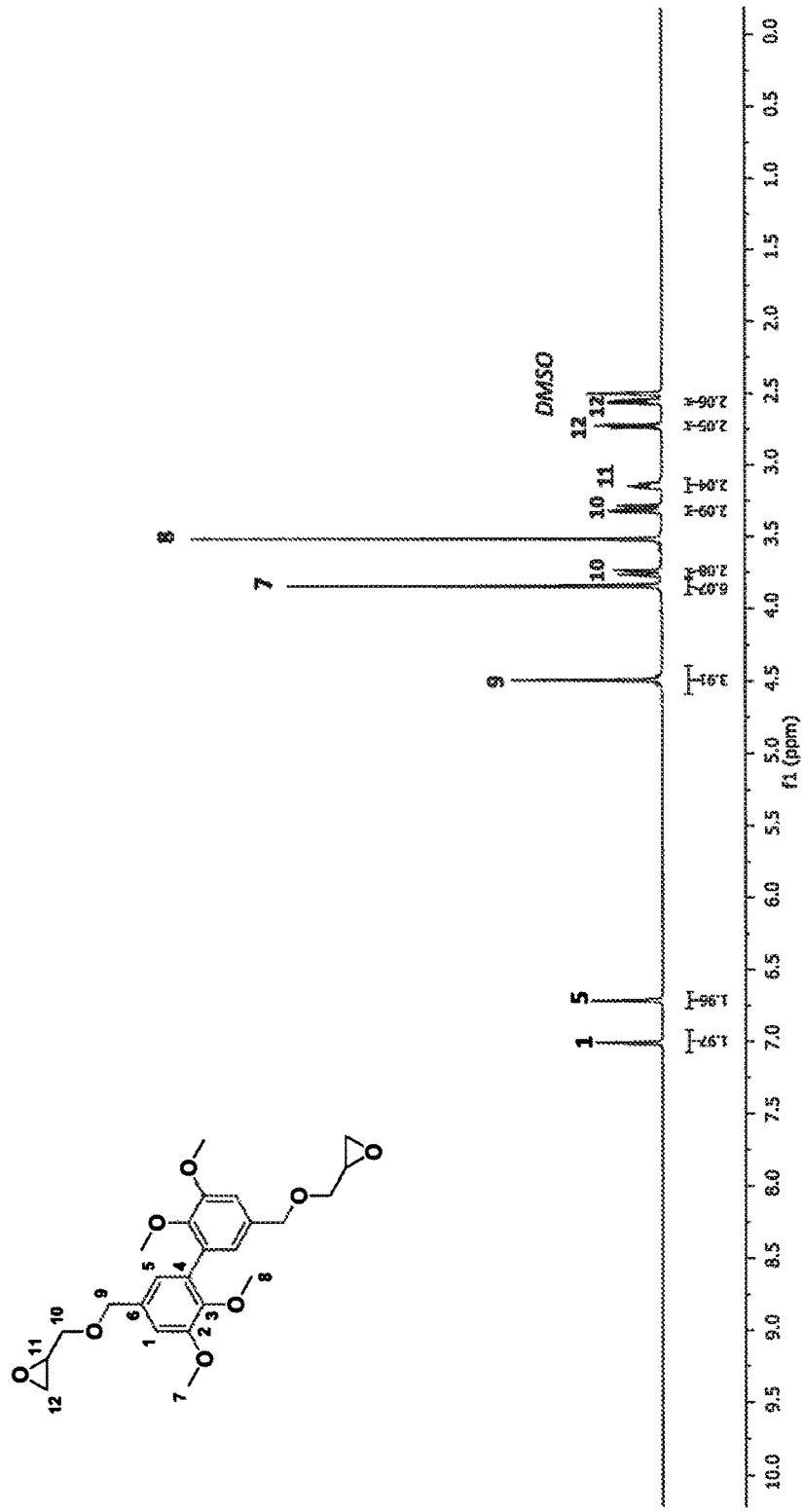
Figure 11B:
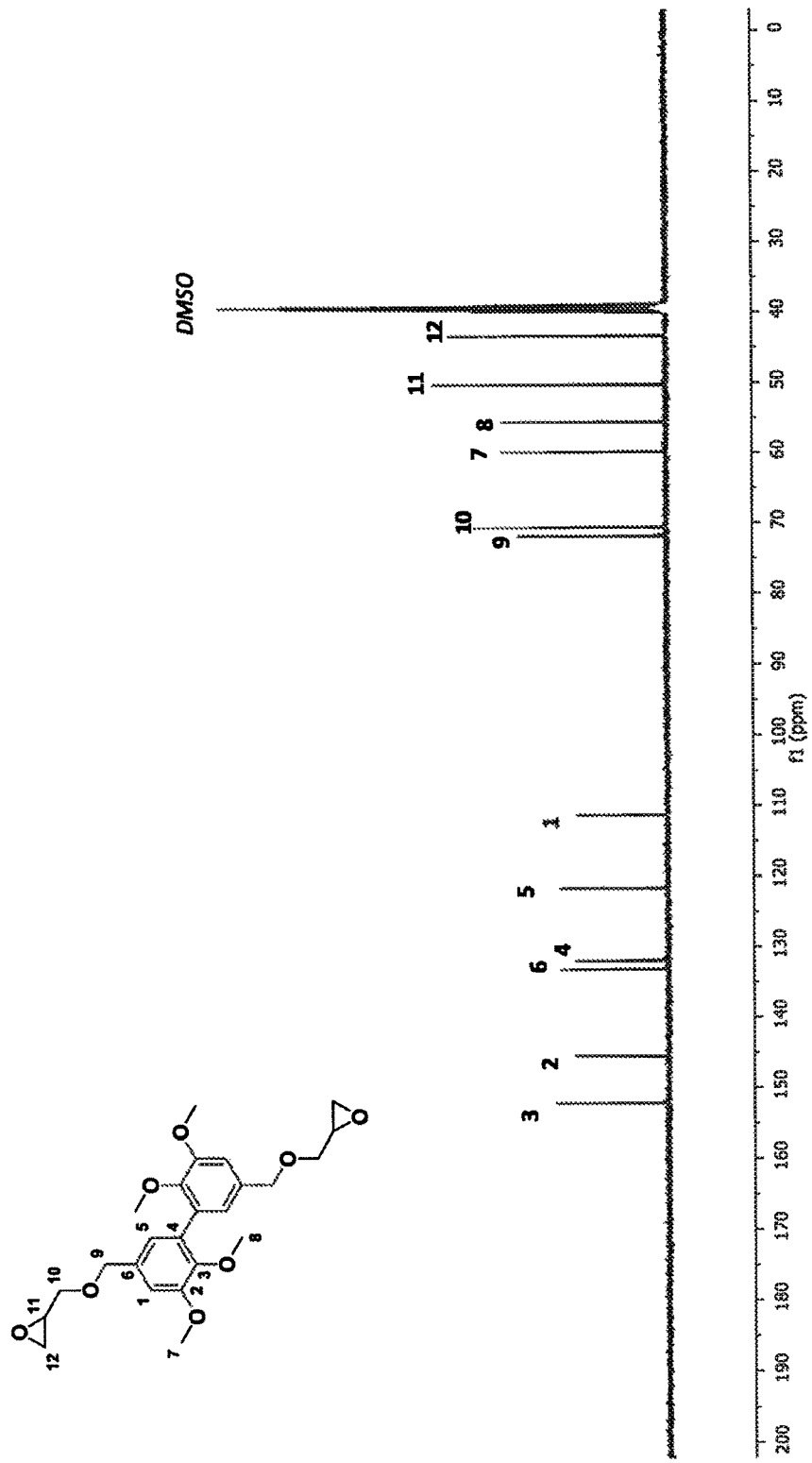

The spectra are shown in FIGS. 11A and 11B respectively.
(with epichlorohydrin) to epoxidize the acid functions of mDVAc. The diglycidyl ether of methylated divanillic acid (DiGEmDVAc) was obtained. Said DiGEmDVAc was characterized by NMR spectroscopy:

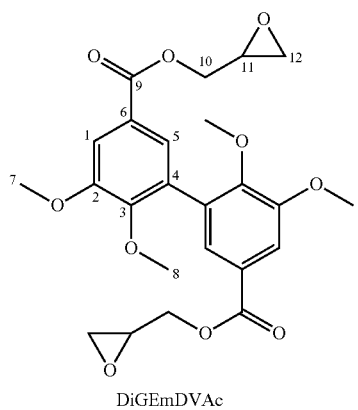

DiGEmDVAc $^1$H NMR (400 MHz, DMSO-d6, δ (ppm)): δ 7.61 (d, H$_1$), 7.45 (d, H$_5$), 4.65 (d, H$_{10}$), 4.08 (q, H$_{10b}$), 3.93 (s, H$_7$), 3.64 (m, H$_8$), 3.34 (m, H$_{11}$), 2.82 (m, H$_{12}$), 2.72 (m, H$_{12b}$).

$^{13}$C NMR (400 MHz, DMSO-d6, δ (ppm)): δ 164.92 (s, C$_9$), 152.34 (s, C$_3$), 150.55 (s, C$_2$), 131.28 (s, C$_6$), 124.41 (s, C$_4$), 124.04 (s, C$_5$), 112.92 (s, C$_1$), 65.58 (s, C$_{10}$), 60.34 (s, C$_8$), 55.97 (s, C$_7$), 49.01 (s, C$_{11}$), 43.90 (s, C$_{12}$).

Figure 12A:
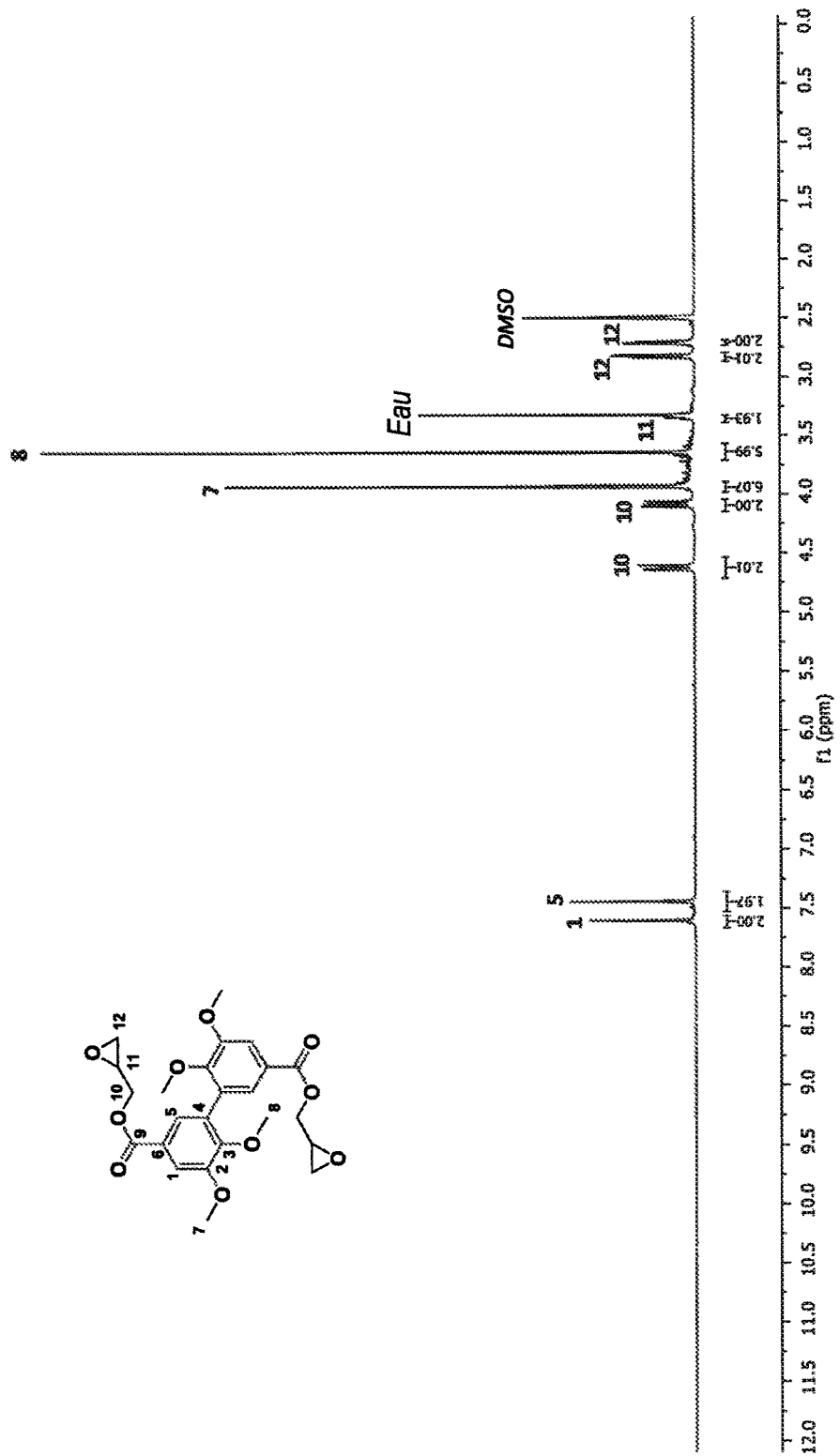

The spectra are shown in FIGS. 12A and 12B respectively. (with the oxidant CPBA) to epoxidize the double bonds of dieugenol. The diglycidyl ether of methylated dieugenol (DiGEmDEG) was obtained. Said DiGEmDEG was characterized by NMR spectroscopy:

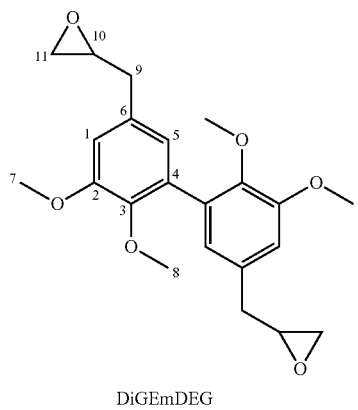

DiGEmDEG $^1$H NMR (400 MHz, DMSO-d6, δ (ppm)): δ 6.95 (d, H$_1$), 6.66 (d, H$_5$), 3.83 (s, H$_7$), 3.51 (s, H$_8$), 3.12 (m, H$_{10}$), 2.74 (m, H$_9$), 2.57 (m, H$_{11}$)

$^{13}$C NMR (400 MHz, DMSO-d6, δ (ppm)): δ 152.15 (s, C$_2$), 144.77 (s, C$_3$), 132.67 (s, C$_6$), 132.24 (s, C$_4$), 122.84 (s, C$_5$), 112.80 (s, C$_1$), 59.95 (s, C$_8$), 55.65 (s, C$_7$), 52.05 (s, C$_{10}$), 46.15 (s, C$_{11}$), 37.90 (s, C$_9$).

Figure 13A:
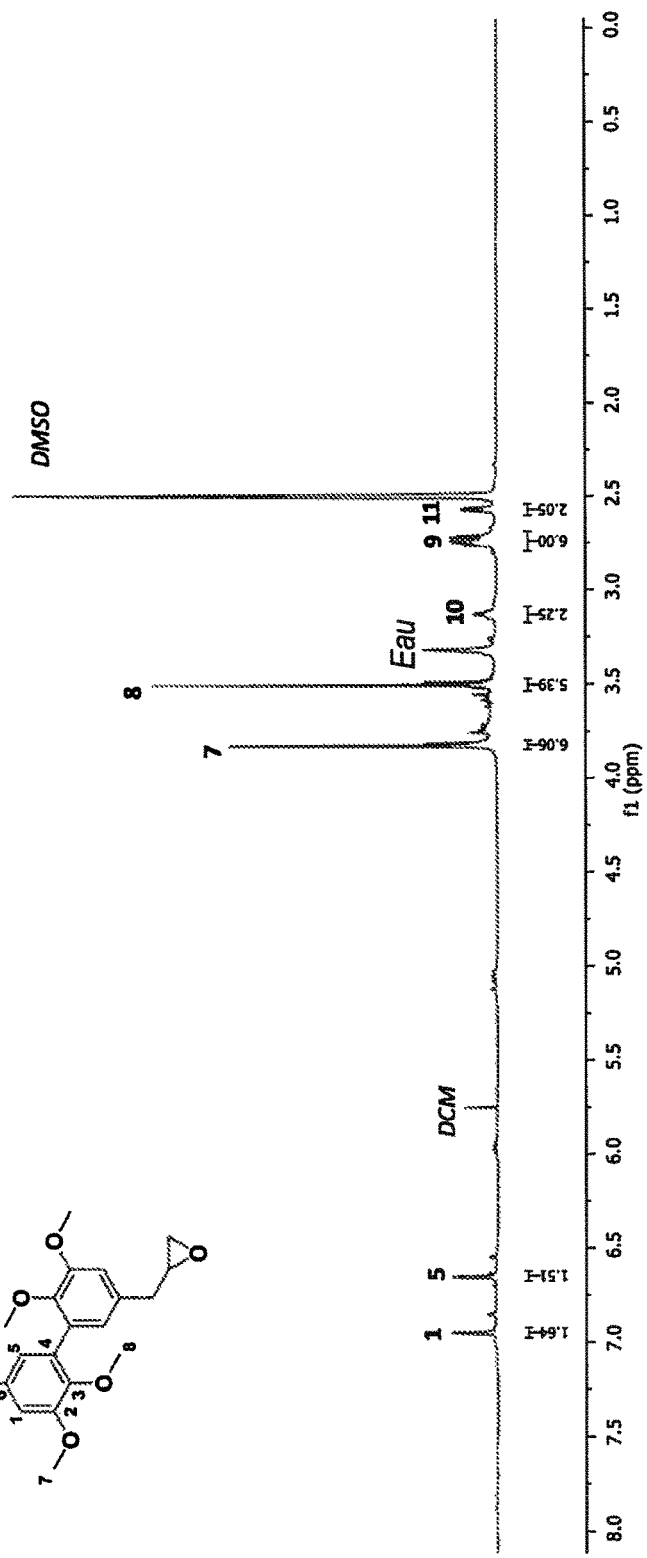
Figure 13B:
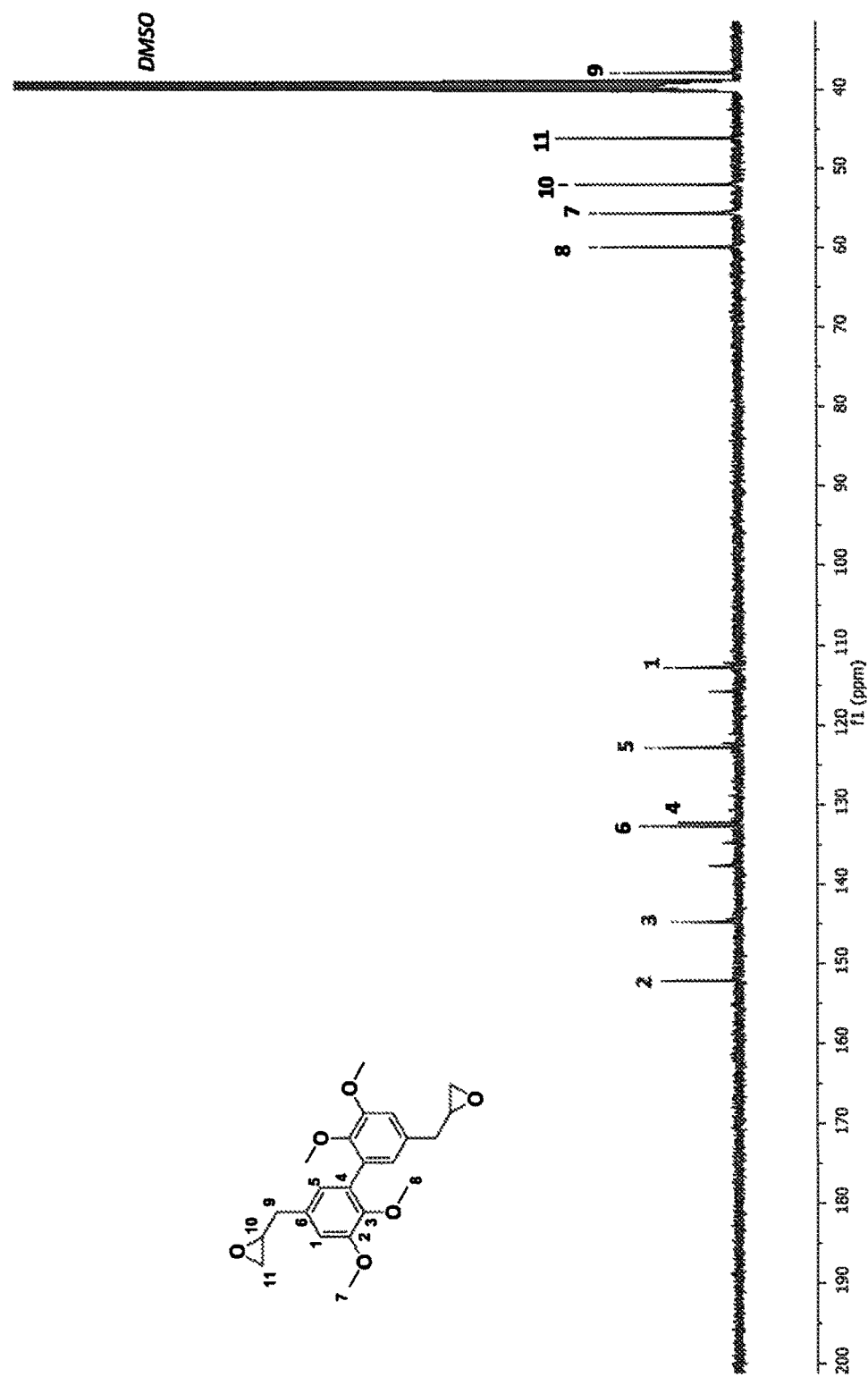

The spectra are shown in FIGS. 13A and 13B respectively.

B6. Polyepoxides Obtained from Said Compounds of Formula (I) (Multi-Epoxidized Prepolymers)

For the polymerization of the compounds of the invention obtained in this example, diaminodiphenyl sulfone (DDS), whose chemical formula has been recalled above, was also used as a hardener.

This hardener was used in a stoichiometric ratio: epoxy/amine=2/1. The polyepoxides were not successively prepared and then analyzed by DMA (for determination of its Tg). They were generated, in small amounts (a few mg), during the implementation of differential scanning calorimetry (DSC), for determination of their Tg.

The rate of residual coke, after degradation at 900° C., determined by thermogravimetric analysis (TGA), was determined on the small amount of DiGEmDVac generated during the DSC analysis. The results are shown in Table 5 below.

TABLE 5

| Polyepoxide precursor prepolymers | Tg (° C.) | Char900 (%) |
|---|---|---|
| DiGEmDVA | 211 | 47 |
| DiGEmDVAc | 175 | 32 |
| DiGEmDEG | 134 | nd* |

*nd = not determined.

The invention claimed is:

1. A compound selected from the group consisting of:
(1) a compound of formula (I):

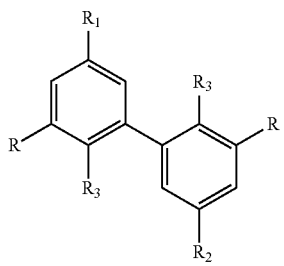

wherein:
R is —O-Alk, where Alk is a linear or branched alkyl group having 1 to 6 carbon atoms,
R$_3$ is —O—Z where Z is a linear or branched alkyl group containing 2 to 8 carbon atoms and containing an epoxy function, or R$_3$ is —O-Alk' where Alk' is a linear or branched alkyl group containing 1 to 6 carbon atoms;
when R$_3$ is —O—Z:
  either R$_1$ and R$_2$, which may be the same or different, are independently selected from —CH$_2$—OH and —CH$_2$—O—Z;
  or R$_1$ and R$_2$, which may be the same or different, are independently selected from —OH and —O—Z;
  or R$_1$ and R$_2$, which may be the same or different, are independently selected from —COOH and —COO—Z,
when R$_3$=—O-Alk':
  R$_1$ and R$_2$ are identical and are selected from the group consisting of:
  —CH$_2$—O—Z, —O—Z, —COO—Z, —CH$_2$-epoxy, and

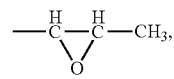

Z being as defined above; and
(2) a mixture of at least two compounds of formula (I).

2. The compound of claim 1, wherein R$_3$ is —O—Z, and Z is a linear alkyl group containing 2 to 8 carbon atoms and an epoxy function.

3. The compound of claim 1, wherein the epoxy function is located at the end of the alkyl chain.

4. The compound of claim 1, wherein $R_3$ is —O—[CH$_2$—]$_n$-epoxy, where n is an integer from 0 to 6.

5. The compound of claim 4, wherein n is an integer from 1 to 6.

6. The compound of claim 4, wherein 1≤n≤4.

7. The compound of claim 1, wherein $R_3$ is —OAlk', and $R_1$ and $R_2$ are identical and are selected from the group consisting of: —CH$_2$—O—Z, —O—Z and —COO—Z, where Z is a linear alkyl group containing 2 to 8 carbon atoms and an epoxy function.

8. The compound of claim 7, wherein the epoxy function is located at the end of the alkyl chain.

9. The compound of claim 7, wherein $R_1$ and $R_2$ are identical and are selected from the group consisting of: —CH$_2$—O—[CH$_2$—]$_n$-epoxy, —O—[CH$_2$—]$_n$-epoxy or —COO—[CH$_2$]$_n$-epoxy, where n is an integer from 0 to 6.

10. The compound of claim 9, wherein $R_1$ and $R_2$ are each —CH$_2$O—CH$_2$-epoxy, —O—CH$_2$-epoxy or —COO—CH$_2$-epoxy.

11. The compound of claim 1, wherein $R_3$ is —O—CH$_3$.

12. A process for preparing a compound of formula (I) as defined in claim 1, the process comprising the steps of:
    a) providing a dimer selected from the group consisting of: (i) divanillin, divanillyl alcohol, dimethoxyhydroquinone, divanillic acid, dieugenol and diisoeugenol, said dimers having at least two phenolic —OH functions and two —O—CH$_3$ functions, and (ii) analogs of said dimers having said at least two phenolic —OH functions and two —O—(C$_2$-C$_6$)alkyl functions,
    b) optionally, alkylating the phenolic —OH functions of the dimer provided in step a) or of an analog thereof, it being understood that the alkylation of divanillin or an analog thereof is followed by oxidation to obtain alkylated di(C$_1$-C$_6$)alkoxyhydroquinone;
    c1) either epoxidizing the phenolic —OH functions of the non-alkylated dimer or analog thereof, or c2) epoxidizing the non-alkylated functions still present on the biphenyl nucleus of the alkylated dimer or analog thereof.

13. The process of claim 12, wherein the epoxidation is carried out:
    by reaction with a compound of formula Cl—Z, wherein Z is a linear or branched alkyl group containing from 2 to 8 carbon atoms and containing an epoxy function, said compound advantageously, or
    by allylation and subsequent oxidative epoxidation of the double bonds introduced, or
    by oxidative epoxidation of at least one double bond present.

14. The process of claim 13 wherein Cl—Z is epichlorohydrin.

15. A thermosetting epoxy resin containing at least one compound of claim 1.

16. A thermoset epoxy resin obtained by heat treatment, in the presence of at least one thermosetting agent, of a thermosetting epoxy resin of claim 15.

17. A compound selected from the group consisting of:

the diglycidyl ether of divanillyl alcohol of formula:

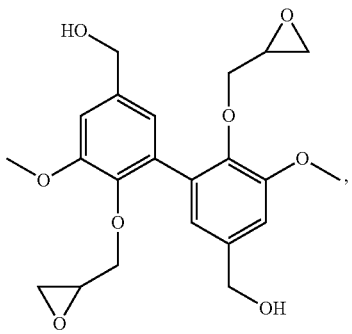

the triglycidyl ether of divanillyl alcohol of formula:

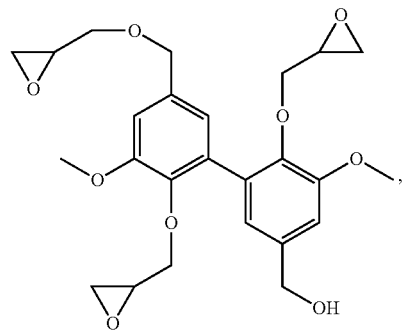 [SMILES: COc1cc(CO)cc(-c2cc(COCC3CO3)cc(OC)c2OCC2CO2)c1OCC1CO1]

the tetraglycidyl ether of divanillyl alcohol of formula:

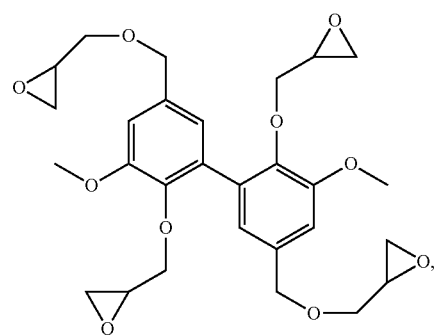 [SMILES: COc1cc(COCC2CO2)cc(-c2cc(COCC3CO3)cc(OC)c2OCC2CO2)c1OCC1CO1]

mixtures of at least two of said glycidyl ethers of divanillyl alcohol, the diglycidyl ether of divanillin of formula:

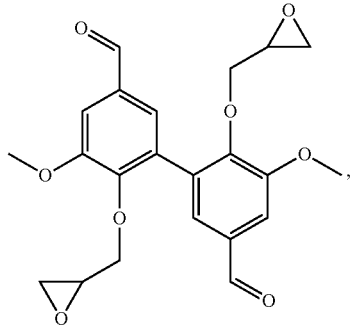

the diglycidyl ether of dimethoxyhydroquinone of formula:

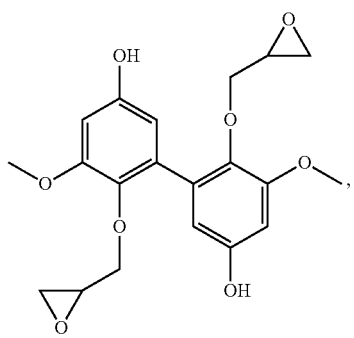

the triglycidyl ether of dimethoxyhydroquinone of formula:

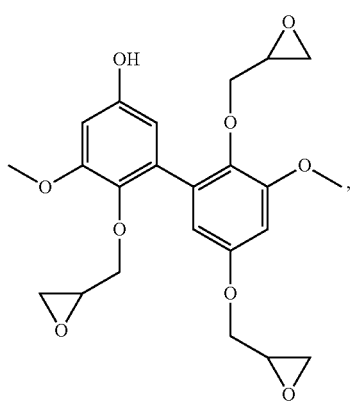

the tetraglycidyl ether of dimethoxyhydroquinone of formula:

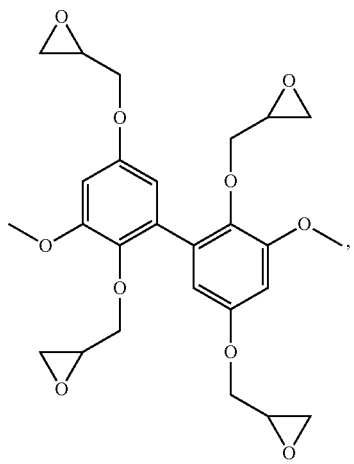

mixtures of at least two of said glycidyl ethers of dimethoxyhydroquinone, the diglycidyl ether of divanillic acid of formula:

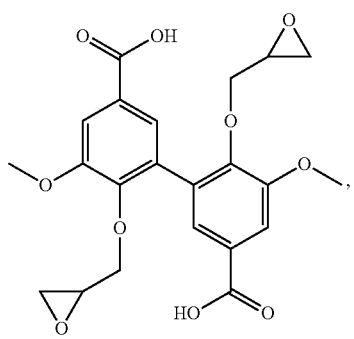

the triglycidyl ether of divanillic acid of formula:

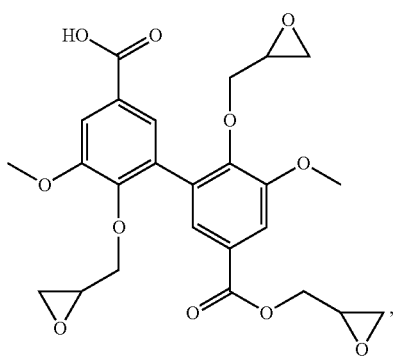 [SMILES: COc1cc(C(=O)O)cc(-c2cc(C(=O)OCC3CO3)cc(OC)c2OCC2CO2)c1OCC1CO1]

51 the tetraglycidyl ether of divanillic acid of formula:

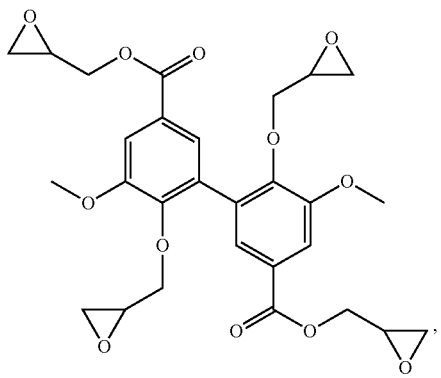 [SMILES: COc1cc(C(=O)OCC2CO2)cc(-c2cc(C(=O)OCC3CO3)cc(OC)c2OCC2CO2)c1OCC1CO1]

mixtures of at least two of said glycidyl ethers of divanillic acid, the diglycidyl ether of dieugenol of formula:

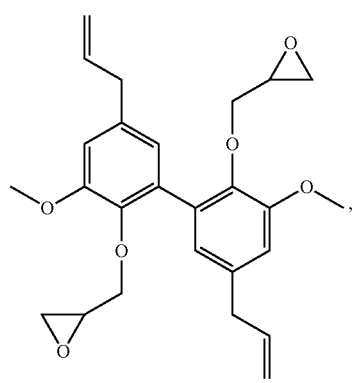

the triglycidyl ether of dieugenol of formula:

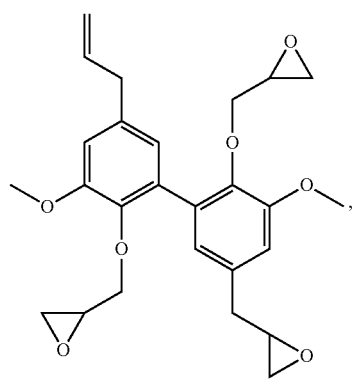

52 the tetraglycidyl ether of dieugenol of formula:

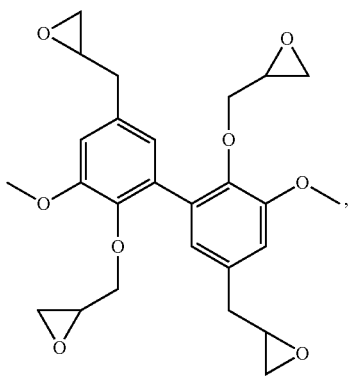

mixtures of at least two of said glycidyl ethers of dieugenol, the diglycidyl ether of diisoeugenol of formula:

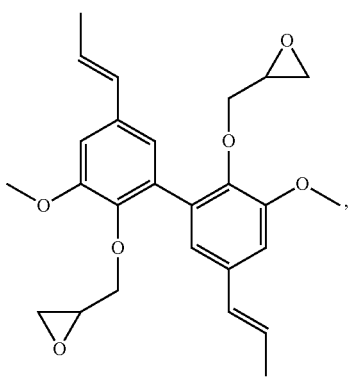

the triglycidyl ether of diisoeugenol of formula:

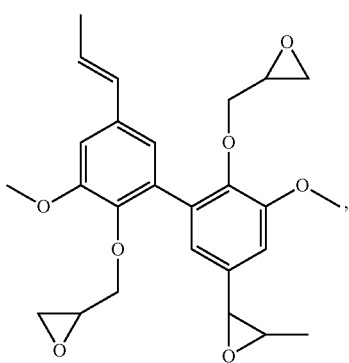

the tetraglycidyl ether of diisoeugenol of formula:

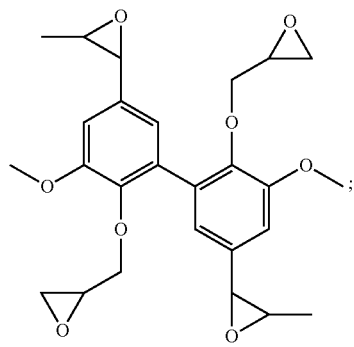

mixtures of at least two of said glycidyl ethers of diisoeugenol, the diglycidyl ether of methylated divanillyl alcohol of formula:

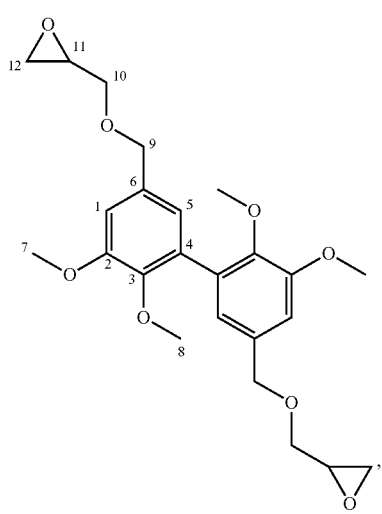 [SMILES: COc1cc(COCC2CO2)cc(-c2cc(COCC3CO3)cc(OC)c2OC)c1OC]

the diglycidyl ether of methylated divanillic acid of formula:

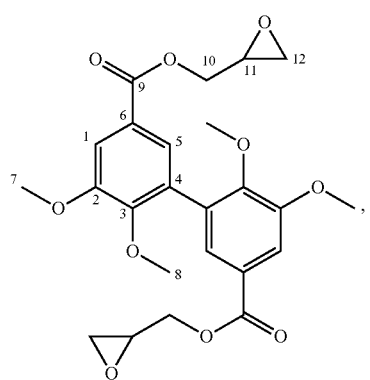

the diglycidyl ether of methylated dimethoxyhydroquinone of formula:

the diglycidyl ether of methylated dieugenol of formula:

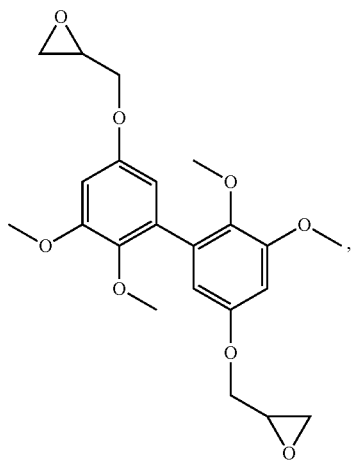

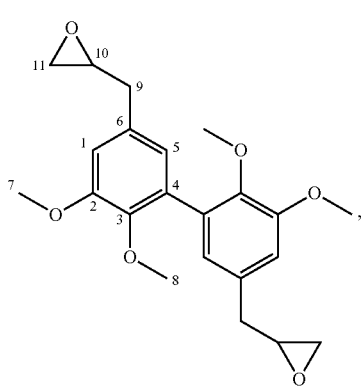

and the diglycidyl ether of methylated diisoeugenol of formula:

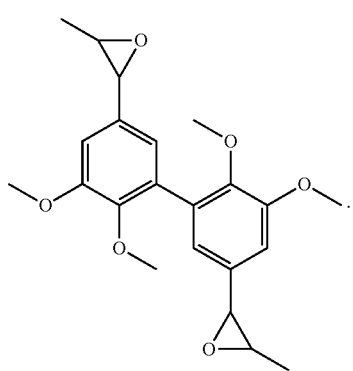

18. The compound of claim 17, which is selected from the group consisting of:

the diglycidyl ether of divanillyl alcohol of formula:

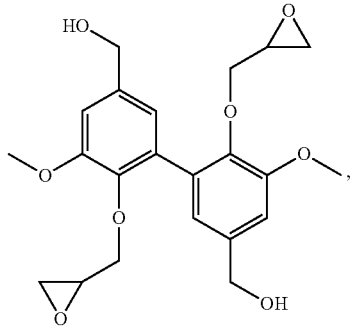

the triglycidyl ether of divanillyl alcohol of formula:

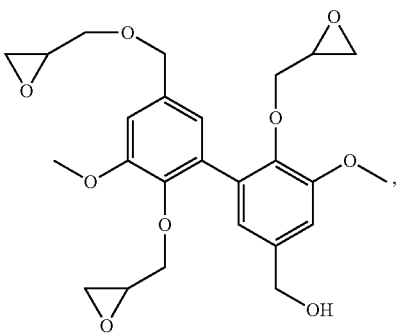

the tetraglycidyl ether of divanillyl alcohol of formula:

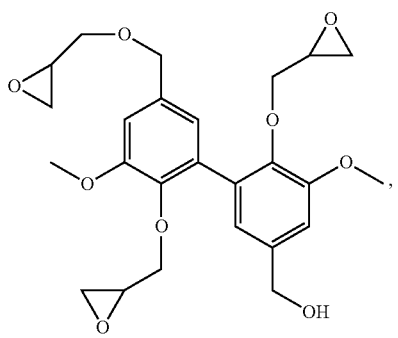 [SMILES: COc1cc(CO)cc(-c2cc(COCC3CO3)cc(OC)c2OCC2CO2)c1OCC1CO1]

and
   mixtures of at least two of said glycidyl ethers of divanillyl alcohol.

19. A thermosetting epoxy resin containing a compound of claim 18.

20. The compound of claim 17, which is the diglycidyl ether of divanillin of formula:

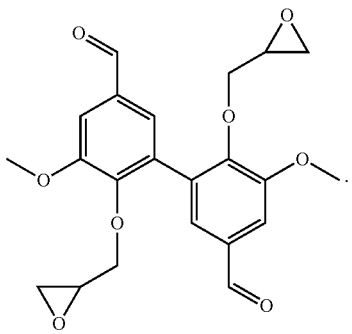

21. A thermosetting epoxy resin containing at least one compound of claim 20.

22. The compound of claim 17, selected from the group consisting of:

the diglycidyl ether of dimethoxyhydroquinone of formula:

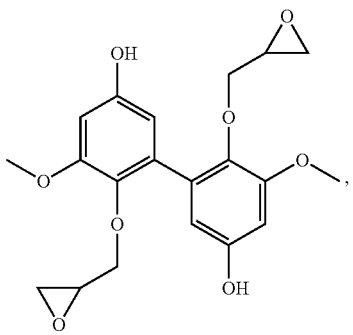

the triglycidyl ether of dimethoxyhydroquinone of formula:

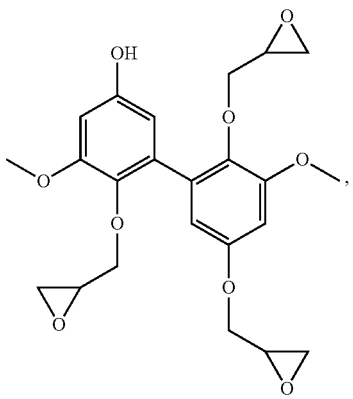

the tetraglycidyl ether of dimethoxyhydroquinone of formula:

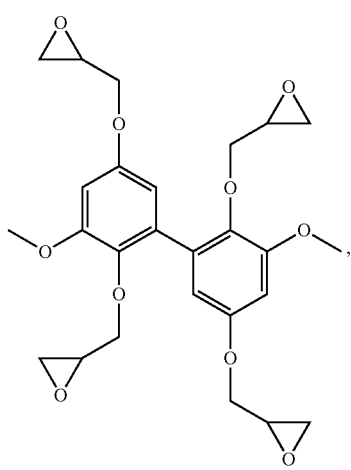

and mixtures of at least two of said glycidyl ethers of dimethoxyhydroquinone.

23. A thermosetting epoxy resin containing at least one compound of claim 22.

24. The compound of claim 17, selected from the group consisting of:

the diglycidyl ether of divanillic acid of formula:

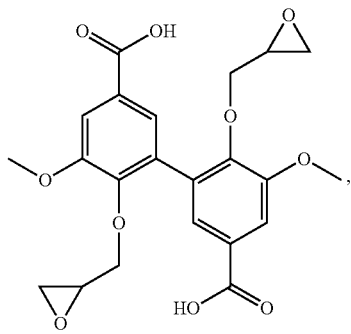

the triglycidyl ether of divanillic acid of formula:

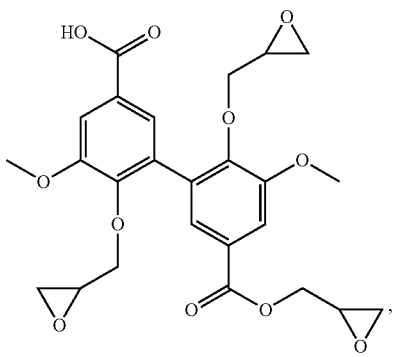 [SMILES: COc1cc(C(=O)O)cc(-c2cc(C(=O)OCC3CO3)cc(OC)c2OCC2CO2)c1OCC1CO1]

the tetraglycidyl ether of divanillic acid of formula:

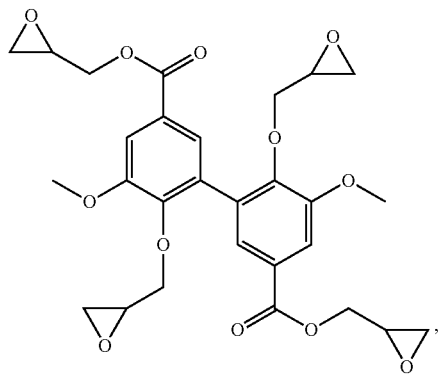 [SMILES: COc1cc(C(=O)OCC2CO2)cc(-c2cc(C(=O)OCC3CO3)cc(OC)c2OCC2CO2)c1OCC1CO1]

and mixtures of at least two of said glycidyl ethers of divanillic acid.

25. A thermosetting epoxy resin containing at least one compound of claim 24.

26. The compound of claim 17, which is selected from the group consisting of:

the diglycidyl ether of dieugenol of formula:

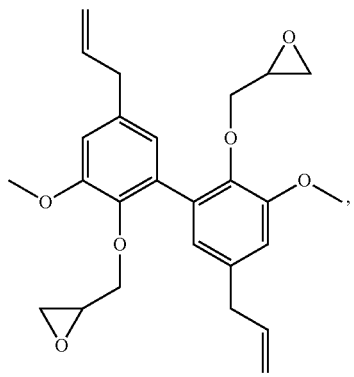

the triglycidyl ether of dieugenol of formula:

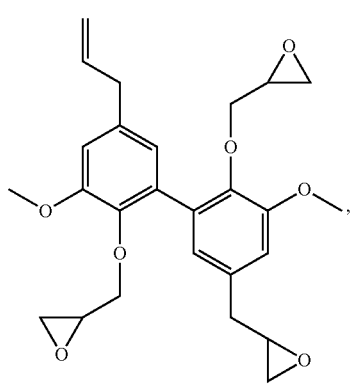

the tetraglycidyl ether of dieugenol of formula:

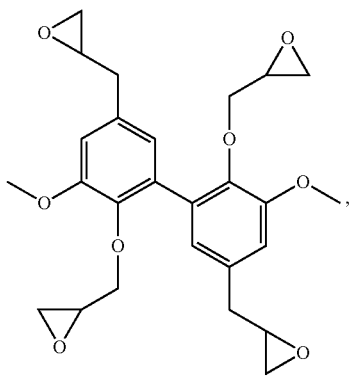

and mixtures of at least two of said glycidyl ethers of dieugenol.

27. A thermosetting epoxy resin containing at least one compound of claim 26.

28. The compound of claim 17, selected from the group consisting of:

the diglycidyl ether of diisoeugenol of formula:

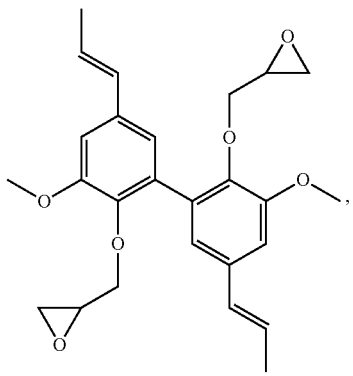

the triglycidyl ether of diisoeugenol of formula:

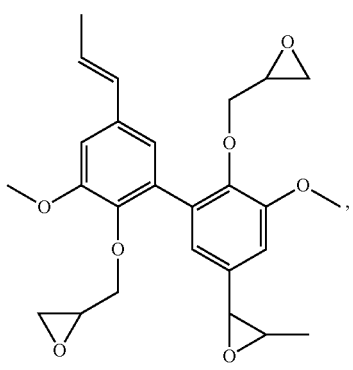

the tetraglycidyl ether of diisoeugenol of formula:

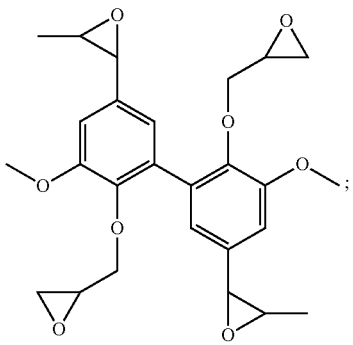

and mixtures of at least two of said glycidyl ethers of diisoeugenol.

29. A thermosetting epoxy resin containing at least one compound of claim 28.

30. The compound of claim 17, selected from the group consisting of:

the diglycidyl ether of methylated divanillyl alcohol of formula:

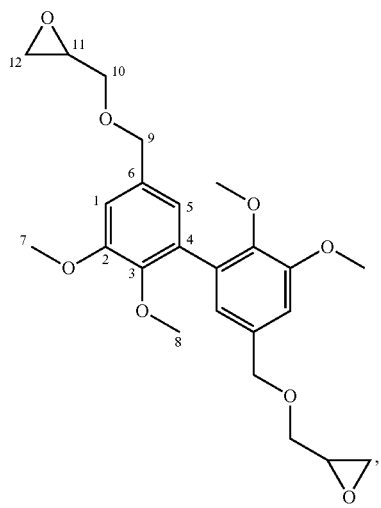 [SMILES: COc1cc(COCC2CO2)cc(-c2cc(COCC3CO3)cc(OC)c2OC)c1OC]

the diglycidyl ether of methylated divanillic acid of formula:

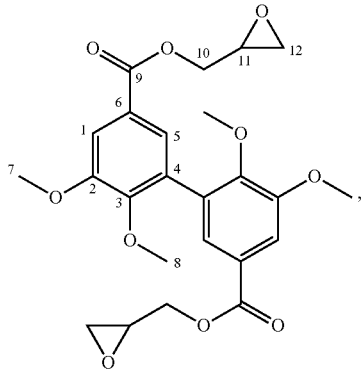

the diglycidyl ether of methylated dimethoxyhydroquinone of formula:
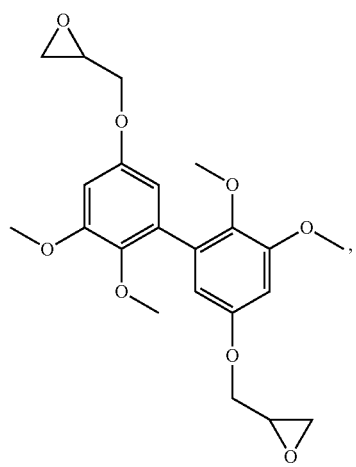
the diglycidyl ether of methylated dieugenol of formula:
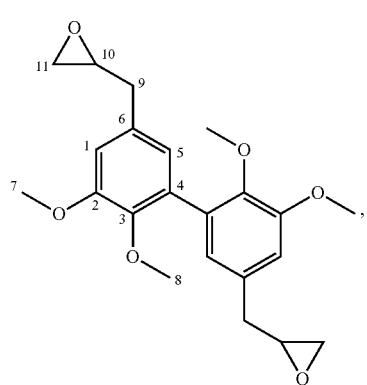
and
the diglycidyl ether of methylated diisoeugenol of formula:
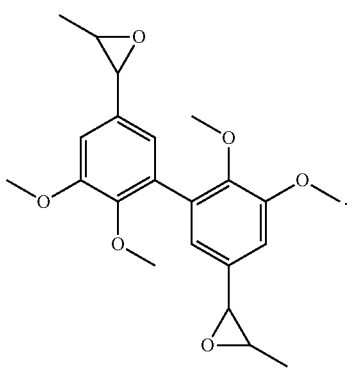
31. A thermosetting epoxy resin containing at least one compound of claim 30.
* * * * *